(12) United States Patent
Lal et al.

(10) Patent No.: US 7,368,270 B2
(45) Date of Patent: May 6, 2008

(54) HUMAN PHOSPHOLIPASES

(75) Inventors: Preeti Lal, Santa Clara, CA (US); Monique G. Yao, Mountain View, CA (US); Henry Yue, Sunnyvale, CA (US); Ameena R. Gandhi, San Francisco, CA (US); Y. Tom Tang, San Jose, CA (US); Farrah A. Khan, Des Plaines, IL (US); Danniel B. Nguyen, San Jose, CA (US); Jennifer L. Policky, San Jose, CA (US); Debopriya Das, Sunnyvale, CA (US); Jennifer L. Hillman, Mountain View, CA (US); Narinder K. Walia, San Leandro, CA (US); April J. A. Hafalia, Santa Clara, CA (US); Catherine M. Tribouley, San Francisco, CA (US)

(73) Assignee: Incyte Corporation, Wilmington, DE (US)

( * ) Notice: Subject to any disclaimer, the term of this patent is extended or adjusted under 35 U.S.C. 154(b) by 48 days.

(21) Appl. No.: 11/275,596

(22) Filed: Jan. 18, 2006

(65) Prior Publication Data

US 2007/0082341 A1 Apr. 12, 2007

Related U.S. Application Data

(62) Division of application No. 10/220,380, filed as application No. PCT/US01/06771 on Feb. 28, 2001, now abandoned.

(60) Provisional application No. 60/198,437, filed on Apr. 19, 2000, provisional application No. 60/190,415, filed on Mar. 17, 2000, provisional application No. 60/186,480, filed on Mar. 2, 2000.

(51) Int. Cl.
*C12N 9/16* (2006.01)
*C12N 5/00* (2006.01)
*C07H 21/04* (2006.01)

(52) U.S. Cl. .................. 435/196; 536/23.2; 435/325; 435/252.3; 435/320.1

(58) Field of Classification Search ............... None
See application file for complete search history.

(56) References Cited

U.S. PATENT DOCUMENTS

| 4,636,195 | A | 1/1987 | Wolinsky |
|---|---|---|---|
| 6,197,324 | B1 | 3/2001 | Crittenden |
| 6,251,418 | B1 | 6/2001 | Ahern et al. |
| 6,394,956 | B1 | 5/2002 | Chandrasekaran et al. |
| 6,800,085 | B2 | 10/2004 | Selmon et al. |
| 2003/0037350 | A1* | 2/2003 | Glucksmann et al. .......... 800/8 |
| 2004/0143321 | A1 | 7/2004 | Litvack et al. |
| 2004/0204672 | A1 | 10/2004 | Palasis et al. |
| 2005/0053548 | A1 | 3/2005 | Strauss |
| 2005/0209559 | A1 | 9/2005 | Thornton et al. |
| 2005/0216044 | A1 | 9/2005 | Hong |
| 2005/0245637 | A1 | 11/2005 | Hossainy et al. |

OTHER PUBLICATIONS

Emanuelli et al., Biochem. Biophys. 298 (1), 29-34 (1992).
Emanuelli et al., J. Biol. Chem. 276 (1), 406-412 (2001), became available on line Oct. 10, 2000.
Schweiger et al., FEBS Lett. 492, 95-100 (2001), published on line Feb. 21, 2001.
Jayaram et al., Cur. Med. Chem. 6, 561-574 (1999).
Emanuelli et al., "Identification and characterization of YLR 328W, the *Saccharomyces cerevisiae* structural gene encoding NMN adenylytransferase. Expression and characterization of the recombinant enzyme", FEBS letters, vol. 455, 1999, (pp. 13-17).
Janben et al., "Human mitochondrial enoyl-CoA hydratase gene (ECHS1): Structural organization and assignment to chromosome 10q26.2-q26.3", Genomics, vol. 40, (1997), pp. 470-475.
Janssen et al., "ECHM Human", EBI/Swissprot, Apr. 1, 1993, No. P30084, XP002186034.
Creighton, T.E.: Encyclopedia of Molecular Biology; vol. 3, pp. 1402-1403 (Hannum Y.A.; Lipid Metabolism), 1999, John Wiley & Sons Inc., NY.
US 6,056,969, 05/2000, Crittenden (withdrawn)

* cited by examiner

*Primary Examiner*—Nashaat T. Nashed
(74) *Attorney, Agent, or Firm*—Foley & Lardner LLP

(57) ABSTRACT

The invention provides human lipid metabolism enzymes (LME) and polynucleotides which identify and encode LME. The invention also provides expression vectors, host cells, antibodies, agonists, and antagonists. The invention also provides methods for diagnosing, treating, or preventing disorders associated with aberrant expression of LME.

5 Claims, No Drawings

```
                          SEQUENCE LISTING

<160> NUMBER OF SEQ ID NOS: 12

<210> SEQ ID NO 1
<211> LENGTH: 303
<212> TYPE: PRT
<213> ORGANISM: Homo sapiens
<220> FEATURE:
<221> NAME/KEY: misc_feature
<223> OTHER INFORMATION: Incyte ID No: 2372651CD1

<400> SEQUENCE: 1

Met Ala Ala Val Ala Val Leu Arg Ala Phe Gly Ala Ser Gly Pro
  1               5                  10                  15

Met Cys Leu Arg Arg Gly Pro Trp Ala Gln Leu Pro Ala Arg Phe
                 20                  25                  30

Cys Ser Arg Asp Pro Ala Gly Ala Gly Arg Arg Glu Ser Glu Pro
                 35                  40                  45

Arg Pro Thr Ser Ala Arg Gln Leu Asp Gly Ile Arg Asn Ile Val
                 50                  55                  60

Leu Ser Asn Pro Lys Lys Arg Asn Thr Leu Ser Leu Ala Met Leu
                 65                  70                  75

Lys Ser Leu Gln Ser Asp Ile Leu His Asp Ala Asp Ser Asn Asp
                 80                  85                  90

Leu Lys Val Ile Ile Ile Ser Ala Glu Gly Pro Val Phe Ser Ser
                 95                 100                 105

Gly His Asp Leu Lys Glu Leu Thr Glu Glu Gln Gly Arg Asp Tyr
                110                 115                 120

His Ala Glu Val Phe Gln Thr Cys Ser Lys Val Met Met His Ile
                125                 130                 135

Arg Asn His Pro Val Pro Val Ile Ala Met Val Asn Gly Leu Ala
                140                 145                 150

Thr Ala Ala Gly Cys Gln Leu Val Ala Ser Cys Asp Ile Ala Val
                155                 160                 165

Ala Ser Asp Lys Ser Ser Phe Ala Thr Pro Gly Val Asn Val Gly
                170                 175                 180

Leu Phe Cys Ser Thr Pro Gly Val Ala Leu Ala Arg Ala Val Pro
                185                 190                 195

Arg Lys Val Ala Leu Glu Met Leu Phe Thr Gly Glu Pro Ile Ser
                200                 205                 210

Ala Gln Glu Ala Leu Leu His Gly Leu Leu Ser Lys Val Val Pro
                215                 220                 225

Glu Ala Glu Leu Gln Glu Glu Thr Met Arg Ile Ala Arg Lys Ile
                230                 235                 240
```

```
Ala Ser Leu Ser Arg Pro Val Val Ser Leu Gly Lys Ala Thr Phe
                245                 250                 255

Tyr Lys Gln Leu Pro Gln Asp Leu Gly Thr Ala Tyr Tyr Leu Thr
                260                 265                 270

Ser Gln Ala Met Val Asp Asn Leu Ala Leu Arg Asp Gly Gln Glu
                275                 280                 285

Gly Ile Thr Ala Phe Leu Gln Lys Arg Lys Pro Val Trp Ser His
                290                 295                 300

Glu Pro Val

<210> SEQ ID NO 2
<211> LENGTH: 515
<212> TYPE: PRT
<213> ORGANISM: Homo sapiens
<220> FEATURE:
<221> NAME/KEY: misc_feature
<223> OTHER INFORMATION: Incyte ID No: 2470792CD1

<400> SEQUENCE: 2

Met Ser Thr Ile Ala Ala Phe Tyr Gly Gly Lys Ser Ile Leu Ile
  1               5                  10                  15

Thr Gly Ala Thr Gly Phe Leu Gly Lys Val Leu Met Glu Lys Leu
                 20                  25                  30

Phe Arg Thr Ser Pro Asp Leu Lys Val Ile Tyr Ile Leu Val Arg
                 35                  40                  45

Pro Lys Ala Gly Gln Thr Leu Gln Gln Arg Val Phe Gln Ile Leu
                 50                  55                  60

Asp Ser Lys Leu Phe Glu Lys Val Lys Glu Val Cys Pro Asn Val
                 65                  70                  75

His Glu Lys Ile Arg Ala Ile Tyr Ala Asp Leu Asn Gln Asn Asp
                 80                  85                  90

Phe Ala Ile Ser Lys Glu Asp Met Gln Glu Leu Leu Ser Cys Thr
                 95                 100                 105

Asn Ile Ile Phe His Cys Ala Ala Thr Val Arg Phe Asp Asp Thr
                110                 115                 120

Leu Arg His Ala Val Gln Leu Asn Val Thr Ala Thr Arg Gln Leu
                125                 130                 135

Leu Leu Met Ala Ser Gln Met Pro Lys Leu Glu Ala Phe Ile His
                140                 145                 150

Ile Ser Thr Ala Tyr Ser Asn Cys Asn Leu Lys His Ile Asp Glu
                155                 160                 165

Val Ile Tyr Pro Cys Pro Val Glu Pro Lys Lys Ile Ile Asp Ser
                170                 175                 180

Leu Glu Trp Leu Asp Asp Ala Ile Ile Asp Glu Ile Thr Pro Lys
                185                 190                 195

Leu Ile Arg Asp Trp Pro Asn Ile Tyr Thr Tyr Thr Lys Ala Leu
                200                 205                 210

Gly Glu Met Val Val Gln Gln Glu Ser Arg Asn Leu Asn Ile Ala
                215                 220                 225

Ile Ile Arg Pro Ser Ile Val Gly Ala Thr Trp Gln Glu Pro Phe
                230                 235                 240

Pro Gly Trp Val Asp Asn Ile Asn Gly Pro Asn Gly Ile Ile Ile
                245                 250                 255

Ala Thr Gly Lys Gly Phe Leu Arg Ala Ile Lys Ala Thr Pro Met
                260                 265                 270
```

```
Ala Val Ala Asp Val Ile Pro Val Asp Thr Val Val Asn Leu Met
            275                 280                 285

Leu Ala Val Gly Trp Tyr Thr Ala Val His Arg Pro Lys Ser Thr
            290                 295                 300

Leu Val Tyr His Ile Thr Ser Gly Asn Met Asn Pro Cys Asn Trp
            305                 310                 315

His Lys Met Gly Val Gln Val Leu Ala Thr Phe Glu Lys Ile Pro
            320                 325                 330

Phe Glu Arg Pro Phe Arg Arg Pro Asn Ala Asn Phe Thr Ser Asn
            335                 340                 345

Ser Phe Thr Ser Gln Tyr Trp Asn Ala Val Ser His Arg Ala Pro
            350                 355                 360

Ala Ile Ile Tyr Asp Cys Tyr Leu Arg Leu Thr Gly Arg Lys Pro
            365                 370                 375

Arg Met Thr Lys Leu Met Asn Arg Leu Leu Arg Thr Val Ser Met
            380                 385                 390

Leu Glu Tyr Phe Ile Asn Arg Ser Trp Glu Trp Ser Thr Tyr Asn
            395                 400                 405

Thr Glu Met Leu Met Ser Glu Leu Ser Pro Glu Asp Gln Arg Val
            410                 415                 420

Phe Asn Phe Asp Val Arg Gln Leu Asn Trp Leu Glu Tyr Ile Glu
            425                 430                 435

Asn Tyr Val Leu Gly Val Lys Lys Tyr Leu Leu Lys Glu Asp Met
            440                 445                 450

Ala Gly Ile Pro Lys Ala Lys Gln Arg Leu Lys Arg Leu Arg Asn
            455                 460                 465

Ile His Tyr Leu Phe Asn Thr Ala Leu Phe Leu Ile Ala Trp Arg
            470                 475                 480

Leu Leu Ile Ala Arg Ser Gln Met Ala Arg Asn Val Trp Phe Phe
            485                 490                 495

Ile Val Ser Phe Cys Tyr Lys Phe Leu Ser Tyr Phe Arg Ala Ser
            500                 505                 510

Ser Thr Leu Lys Val
            515

<210> SEQ ID NO 3
<211> LENGTH: 279
<212> TYPE: PRT
<213> ORGANISM: Homo sapiens
<220> FEATURE:
<221> NAME/KEY: misc_feature
<223> OTHER INFORMATION: Incyte ID No: 1506182CD1

<400> SEQUENCE: 3

Met Glu Asn Ser Glu Lys Thr Glu Val Val Leu Leu Ala Cys Gly
  1               5                  10                  15

Ser Phe Asn Pro Ile Thr Asn Met His Leu Arg Leu Phe Glu Leu
            20                  25                  30

Ala Lys Asp Tyr Met Asn Gly Thr Gly Arg Tyr Thr Val Val Lys
            35                  40                  45

Gly Ile Ile Ser Pro Val Gly Asp Ala Tyr Lys Lys Lys Gly Leu
            50                  55                  60

Ile Pro Ala Tyr His Arg Val Ile Met Ala Glu Leu Ala Thr Lys
            65                  70                  75

Asn Ser Lys Trp Val Glu Val Asp Thr Trp Glu Ser Leu Gln Lys
```

-continued

```
                    80                  85                  90
Glu Trp Lys Glu Thr Leu Lys Val Leu Arg His His Gln Glu Lys
                95                 100                 105

Leu Glu Ala Ser Asp Cys Asp His Gln Gln Asn Ser Pro Thr Leu
            110                 115                 120

Glu Arg Pro Gly Arg Lys Arg Lys Trp Thr Glu Thr Gln Asp Ser
            125                 130                 135

Ser Gln Lys Lys Ser Leu Glu Pro Lys Thr Lys Ala Val Pro Lys
            140                 145                 150

Val Lys Leu Leu Cys Gly Ala Asp Leu Leu Glu Ser Phe Ala Val
            155                 160                 165

Pro Asn Leu Trp Lys Ser Glu Asp Ile Thr Gln Ile Val Ala Asn
            170                 175                 180

Tyr Gly Leu Ile Cys Val Thr Arg Ala Gly Asn Asp Ala Gln Lys
            185                 190                 195

Phe Ile Tyr Glu Ser Asp Val Leu Trp Lys His Arg Ser Asn Ile
            200                 205                 210

His Val Val Asn Glu Trp Ile Ala Asn Asp Ile Ser Ser Thr Lys
            215                 220                 225

Ile Arg Arg Ala Leu Arg Arg Gly Gln Ser Ile Arg Tyr Leu Val
            230                 235                 240

Pro Asp Leu Val Gln Glu Tyr Ile Glu Lys His Asn Leu Tyr Ser
            245                 250                 255

Ser Glu Ser Glu Asp Arg Asn Ala Gly Val Ile Leu Ala Pro Leu
            260                 265                 270

Gln Arg Asn Thr Ala Glu Ala Lys Thr
            275

<210> SEQ ID NO 4
<211> LENGTH: 432
<212> TYPE: PRT
<213> ORGANISM: Homo sapiens
<220> FEATURE:
<221> NAME/KEY: misc_feature
<223> OTHER INFORMATION: Incyte ID No: 2690842CD1

<400> SEQUENCE: 4

Met Arg Thr Met Trp Phe Ala Gly Gly Phe His Arg Val Ala Val
  1               5                  10                  15

Lys Gly Arg Gln Ala Leu Pro Thr Glu Ala Ala Ile Leu Thr Leu
             20                  25                  30

Ala Pro His Ser Ser Tyr Phe Asp Ala Ile Pro Val Thr Met Thr
             35                  40                  45

Met Ser Ser Ile Val Met Lys Ala Glu Ser Arg Asp Ile Pro Ile
             50                  55                  60

Trp Gly Thr Leu Ile Gln Tyr Ile Arg Pro Val Phe Val Ser Arg
             65                  70                  75

Ser Asp Gln Asp Ser Arg Arg Lys Thr Val Glu Glu Ile Lys Arg
             80                  85                  90

Arg Ala Gln Ser Asn Gly Lys Trp Pro Gln Ile Met Ile Phe Pro
             95                 100                 105

Glu Gly Thr Cys Thr Asn Arg Thr Cys Leu Ile Thr Phe Lys Pro
            110                 115                 120

Gly Ala Phe Ile Pro Gly Ala Pro Val Gln Pro Val Val Leu Arg
            125                 130                 135
```

```
Tyr Pro Asn Lys Leu Asp Thr Ile Thr Trp Thr Trp Gln Gly Pro
            140                 145                 150

Gly Ala Leu Glu Ile Leu Trp Leu Thr Leu Cys Gln Phe His Asn
            155                 160                 165

Gln Val Glu Ile Glu Phe Leu Pro Val Tyr Ser Pro Ser Glu Glu
            170                 175                 180

Glu Lys Arg Asn Pro Ala Leu Tyr Ala Ser Asn Val Arg Arg Val
            185                 190                 195

Met Ala Glu Ala Leu Gly Val Ser Val Thr Asp Tyr Thr Phe Glu
            200                 205                 210

Asp Cys Gln Leu Ala Leu Ala Glu Gly Gln Leu Arg Leu Pro Ala
            215                 220                 225

Asp Thr Cys Leu Leu Glu Phe Ala Arg Leu Val Arg Gly Leu Gly
            230                 235                 240

Leu Lys Pro Glu Lys Leu Glu Lys Asp Leu Asp Arg Tyr Ser Glu
            245                 250                 255

Arg Ala Arg Met Lys Gly Gly Glu Lys Ile Gly Ile Ala Glu Phe
            260                 265                 270

Ala Ala Ser Leu Glu Val Pro Val Ser Asp Leu Leu Glu Asp Met
            275                 280                 285

Phe Ser Leu Phe Asp Glu Ser Gly Ser Gly Glu Val Asp Leu Arg
            290                 295                 300

Glu Cys Val Val Ala Leu Ser Val Val Cys Arg Pro Ala Arg Thr
            305                 310                 315

Leu Asp Thr Ile Gln Leu Ala Phe Lys Thr Tyr Gly Ala Gln Glu
            320                 325                 330

Asp Gly Ser Val Gly Glu Gly Asp Leu Ser Cys Ile Leu Lys Thr
            335                 340                 345

Ala Leu Gly Val Ala Glu Leu Thr Val Thr Asp Leu Phe Arg Ala
            350                 355                 360

Ile Asp Gln Glu Glu Lys Gly Lys Ile Thr Phe Ala Asp Phe His
            365                 370                 375

Arg Phe Ala Glu Met Tyr Pro Ala Phe Ala Glu Glu Tyr Leu Tyr
            380                 385                 390

Pro Asp Gln Thr His Phe Glu Ser Cys Ala Glu Thr Ser Pro Ala
            395                 400                 405

Pro Ile Pro Asn Gly Phe Cys Ala Asp Phe Ser Pro Glu Asn Ser
            410                 415                 420

Asp Ala Gly Arg Lys Pro Val Arg Lys Lys Leu Asp
            425                 430

<210> SEQ ID NO 5
<211> LENGTH: 451
<212> TYPE: PRT
<213> ORGANISM: Homo sapiens
<220> FEATURE:
<221> NAME/KEY: misc_feature
<223> OTHER INFORMATION: Incyte ID No: 5027764CD1

<400> SEQUENCE: 5

Met Leu Arg Phe Tyr Leu Phe Ile Ser Leu Leu Cys Leu Ser Arg
  1               5                  10                  15

Ser Asp Ala Glu Glu Thr Cys Pro Ser Phe Thr Arg Leu Ser Phe
            20                  25                  30

His Ser Ala Val Val Gly Thr Gly Leu Asn Val Arg Leu Met Leu
            35                  40                  45
```

-continued

Tyr Thr Arg Lys Asn Leu Thr Cys Ala Gln Thr Ile Asn Ser Ser
            50                  55                  60

Ala Phe Gly Asn Leu Asn Val Thr Lys Thr Thr Phe Ile Val
        65                  70                      75

His Gly Phe Arg Pro Thr Gly Ser Pro Val Trp Met Asp Asp
            80                  85                  90

Leu Val Lys Gly Leu Leu Ser Val Glu Asp Met Asn Val Val
            95                 100                 105

Val Asp Trp Asn Arg Gly Ala Thr Thr Leu Ile Tyr Thr His Ala
                110                 115                 120

Ser Ser Lys Thr Arg Lys Val Ala Met Val Leu Lys Glu Phe Ile
                125                 130                 135

Asp Gln Met Leu Ala Glu Gly Ala Ser Leu Asp Asp Ile Tyr Met
                140                 145                 150

Ile Gly Val Ser Leu Gly Ala His Ile Ser Gly Phe Val Gly Glu
                155                 160                 165

Met Tyr Asp Gly Trp Leu Gly Arg Ile Thr Gly Leu Asp Pro Ala
                170                 175                 180

Gly Pro Leu Phe Asn Gly Lys Pro His Gln Asp Arg Leu Asp Pro
                185                 190                 195

Ser Asp Ala Gln Phe Val Asp Val Ile His Ser Asp Thr Asp Ala
                200                 205                 210

Leu Gly Tyr Lys Glu Pro Leu Gly Asn Ile Asp Phe Tyr Pro Asn
                215                 220                 225

Gly Gly Leu Asp Gln Pro Gly Cys Pro Lys Thr Ile Leu Gly Gly
                230                 235                 240

Phe Gln Tyr Phe Lys Cys Asp His Gln Arg Ser Val Tyr Leu Tyr
                245                 250                 255

Leu Ser Ser Leu Arg Glu Ser Cys Thr Ile Thr Ala Tyr Pro Cys
                260                 265                 270

Asp Ser Tyr Gln Asp Tyr Arg Asn Gly Lys Cys Val Ser Cys Gly
                275                 280                 285

Thr Ser Gln Lys Glu Ser Cys Pro Leu Leu Gly Tyr Tyr Ala Asp
                290                 295                 300

Asn Trp Lys Asp His Leu Arg Gly Lys Asp Pro Pro Met Thr Lys
                305                 310                 315

Ala Phe Phe Asp Thr Ala Glu Glu Ser Pro Phe Cys Met Tyr His
                320                 325                 330

Tyr Phe Val Asp Ile Ile Thr Trp Asn Lys Asn Val Arg Arg Gly
                335                 340                 345

Asp Ile Thr Ile Lys Leu Arg Asp Lys Ala Gly Asn Thr Thr Glu
                350                 355                 360

Ser Lys Ile Asn His Glu Pro Thr Thr Phe Gln Lys Tyr His Gln
                365                 370                 375

Val Ser Leu Leu Ala Arg Phe Asn Gln Asp Leu Asp Lys Val Ala
                380                 385                 390

Ala Ile Ser Leu Met Phe Ser Thr Gly Ser Leu Ile Gly Pro Arg
                395                 400                 405

Tyr Lys Leu Arg Ile Leu Arg Met Lys Leu Arg Ser Leu Ala His
                410                 415                 420

Pro Glu Arg Pro Gln Leu Cys Arg Tyr Asp Leu Val Leu Met Glu
                425                 430                 435

-continued

```
Asn Val Glu Thr Val Phe Gln Pro Ile Leu Cys Pro Glu Leu Gln
                440                 445                 450

Leu

<210> SEQ ID NO 6
<211> LENGTH: 312
<212> TYPE: PRT
<213> ORGANISM: Homo sapiens
<220> FEATURE:
<221> NAME/KEY: misc_feature
<223> OTHER INFORMATION: Incyte ID No: 2488174CD1

<400> SEQUENCE: 6

Met Pro Gly Thr Leu Trp Cys Gly Val Gly Asp Ser Ala Gly Asn
  1               5                  10                  15

Ser Ser Glu Leu Gly Val Phe Gln Gly Pro Asp Leu Cys Cys Arg
                 20                  25                  30

Glu His Asp Arg Cys Pro Gln Asn Ile Ser Pro Leu Gln Tyr Asn
                 35                  40                  45

Tyr Gly Ile Arg Asn Tyr Arg Phe His Thr Ile Ser His Cys Asp
                 50                  55                  60

Cys Asp Thr Arg Cys Arg Met Tyr Gly Thr Val Pro Leu Ala Arg
                 65                  70                  75

Leu Gln Pro Arg Thr Phe Tyr Asn Ala Ser Trp Ser Ser Arg Ala
                 80                  85                  90

Thr Ser Pro Thr Pro Ser Ser Arg Ser Pro Ala Pro Pro Lys Pro
                 95                 100                 105

Arg Gln Lys Gln His Leu Arg Lys Gly Pro Pro His Gln Lys Gly
                110                 115                 120

Ser Lys Arg Pro Ser Lys Ala Asn Thr Thr Ala Leu Gln Asp Pro
                125                 130                 135

Met Val Ser Pro Arg Leu Asp Val Ala Pro Thr Gly Leu Gln Gly
                140                 145                 150

Pro Gln Gly Gly Leu Lys Pro Gln Gly Ala Arg Trp Val Cys Arg
                155                 160                 165

Ser Phe Arg Arg His Leu Asp Gln Cys Glu His Gln Ile Gly Pro
                170                 175                 180

Arg Glu Ile Glu Phe Gln Leu Leu Asn Ser Ala Gln Glu Pro Leu
                185                 190                 195

Phe His Cys Asn Cys Thr Arg Arg Leu Ala Arg Phe Leu Arg Leu
                200                 205                 210

His Ser Pro Pro Glu Val Thr Asn Met Leu Trp Glu Leu Leu Gly
                215                 220                 225

Thr Thr Cys Phe Lys Leu Ala Pro Pro Leu Asp Cys Val Glu Gly
                230                 235                 240

Lys Asn Cys Ser Arg Asp Pro Arg Ala Ile Arg Val Ser Ala Arg
                245                 250                 255

His Leu Arg Arg Leu Gln Gln Arg Arg His Gln Leu Gln Asp Lys
                260                 265                 270

Gly Thr Asp Glu Arg Gln Pro Trp Pro Ser Glu Pro Leu Arg Gly
                275                 280                 285

Pro Met Ser Phe Tyr Asn Gln Cys Leu Gln Leu Thr Gln Ala Ala
                290                 295                 300

Arg Arg Pro Asp Arg Gln Gln Lys Ser Trp Ser Gln
                305                 310
```

<210> SEQ ID NO 7
<211> LENGTH: 1667
<212> TYPE: DNA
<213> ORGANISM: Homo sapiens
<220> FEATURE:
<221> NAME/KEY: misc_feature
<223> OTHER INFORMATION: Incyte ID No: 2372651CB1

<400> SEQUENCE: 7

| | | | | | |
|---|---|---|---|---|---|
| cgcctggcct | ggggcgtctc | cgcgaacctg | ggcctgtcag | gcggttccgt | ccgggtctcg | 60 |
| gccaccgtcg | agttccgtcg | agttccgtcc | cggccctgct | cacagcagcg | ccctcggagc | 120 |
| gcccagcacc | tgcggccggc | caggcagcgc | gatcctgcgg | cgtctggcca | tcccgaatgc | 180 |
| tatggccgcc | gtcgccgtct | tgcgggcctt | cggggcaagt | gggcccatgt | gtctccggcg | 240 |
| cggcccctgg | gccagctcc | ccgcccgctt | ctgcagccgg | gaccccggccg | gggcggggcg | 300 |
| gcgggagtcg | gagccgcggc | ccaccagcgc | gcggcagctg | gacggcataa | ggaacatcgt | 360 |
| cttgagcaat | cccaagaaga | ggaacacgtt | gtcacttgca | atgctgaaat | ctctccaaag | 420 |
| tgacattctt | catgacgctg | acagcaacga | tctgaaagtc | attatcatct | cggctgaggg | 480 |
| gcctgtgttt | tcttctgggc | atgacttaaa | ggagctgaca | gaggagcaag | gccgtgatta | 540 |
| ccatgccgaa | gtatttcaga | cctgttccaa | ggtcatgatg | cacatccgga | accaccccgt | 600 |
| ccccgtcatt | gccatggtca | atggcctggc | cacggctgcc | ggctgtcaac | tggttgccag | 660 |
| ctgcgacatt | gccgtggcga | gcgacaagtc | ctcttttgcc | actcctgggg | tgaacgtcgg | 720 |
| gctcttctgt | tctacccctg | gggttgcctt | ggcaagagca | gtgcctagaa | aggtggcctt | 780 |
| ggagatgctc | tttactggtg | agcccatttc | tgcccaggag | gccctgctcc | acgggctgct | 840 |
| tagcaaggtg | gtgccagagg | cggagctgca | ggaggagacc | atgcggatcg | ctaggaagat | 900 |
| cgcatcgctg | agccgtccgg | tggtgtccct | gggcaaagcc | accttctaca | gcagctgcc | 960 |
| ccaggacctg | ggacggcttt | actacctcac | ctcccaggcc | atggtggaca | acctggccct | 1020 |
| gcgggacggg | caggagggca | tcacggcctt | cctccagaag | agaaaacctg | tctggtcaca | 1080 |
| cgagccagtg | tgagtggagg | cagaggagtg | aggcccacgg | gcagcgccca | ggagcccacc | 1140 |
| ttcccctctg | gccagccac | cactgcctct | cagcttcaac | aggtgacagg | ctgctttcgt | 1200 |
| gacttgatat | tggtgtcata | gcatttggcc | tacattaaaa | gccacaattt | catgggaaa | 1260 |
| ggacaaaatg | gagagtgact | gaggtgctga | cctcagtgca | aggctggtga | accctgcagc | 1320 |
| gggccagcta | tggtgggaag | cctggcatt | ggggtgctcc | ttgcaacgtc | ttaagcaagc | 1380 |
| gaccccctg | acatagcaaa | aggtggcaac | ccatggaggc | agaagaagg | acgccagcct | 1440 |
| gacccttatc | tgaaacgtcc | taagcagagt | taatcctggc | tgctcaggag | aggcgacaca | 1500 |
| tttcaaatct | ccacgagata | ttctccacac | agaaaatctt | cttgattcta | tagagactta | 1560 |
| atcatgccta | tggctttgaa | taatcttatg | tgatttaaat | aaattaaatc | tttatagaga | 1620 |
| aaaaaaaaa | aaaaaaaaa | aaaaaaaaa | aaaaaaaaa | aaaaaa | | 1667 |

<210> SEQ ID NO 8
<211> LENGTH: 2124
<212> TYPE: DNA
<213> ORGANISM: Homo sapiens
<220> FEATURE:
<221> NAME/KEY: misc_feature
<223> OTHER INFORMATION: Incyte ID No: 2470792CB1

<400> SEQUENCE: 8

| | | | | | |
|---|---|---|---|---|---|
| cggagccggt | gaaggtcgga | gggagggtgg | tttcctcccg | ccccacaccc | agtctccgag | 60 |

```
ccggatatat agagtgtcac gtttgggagc cgaaagactg gagccgtttc cttgtggctg      120
gagcgcttcc cgtagcctcg gggaaggagc aggatttaga ggaccactag ttggacccca      180
tcctcgtgct ggaggaacag gaacctcttt caggagctat aaaagaaagg gaggaatcat      240
gtccacaatt gcagctttct atggcggcaa gtccattctc atcacggggg ccacaggctt      300
tctgggcaaa gtgctgatgg agaagctgtt tcgcaccagc ccagacctga aagtcattta      360
catccttgtg aggcccaagg ctggccagac actgcagcag agggttttcc agatcctaga      420
cagtaagcta tttgagaaag tcaaagaagt ttgtccaaat gtgcatgaga agatcagagc      480
tatttatgca gatctcaatc agaatgactt tgccatcagc aaagaggaca tgcaggagct      540
tctctcctgt acaaacataa tatttcactg tgcagccact gtacgctttg acgacactct      600
cagacatgct gtgcaactta acgtcactgc caccgggcag ctcttgctta tggctagtca      660
gatgccaaag ctggaagcct ttatacatat ctctactgcc tattcaaatt gtaacctgaa      720
gcacatcgat gaagttatct atccgtgccc tgtggagcca aaaaaaatca ttgattccct      780
tgagtggtta gacgatgcta ttattgacga gattacaccc aagctgatca gagattggcc      840
caatatttat acctacacca aggccttggg agaaatggtg gtgcagcaag agagcaggaa      900
cctgaacatt gccatcataa ggccctccat tgtgggagca acttggcagg agcctttccc      960
aggttgggtt gataatataa atggacctaa tggaatcatt attgcgactg ggaaagggtt     1020
tcttcgggcc ataaaagcta ctccaatggc tgtggcagac gtaattccag ttgatacagt     1080
cgtcaatctc atgctagctg taggatggta tactgcagtt cacagaccta agtcaacatt     1140
agtctaccac attacatctg gtaacatgaa tccctgcaat tggcacaaaa tgggagtcca     1200
agtcttggca acctttgaaa aaatcccatt tgagagacct tcaggaggc caaatgctaa     1260 ttttaccagc aacagcttca catcacagta ctggaatgcg gtcagccacc gggcccctgc     1320
cattatctat gactgctatc tgcggctcac tggaaggaag cccaggatga caaagctcat     1380
gaatcggctt ttaagaactg tttccatgtt ggagtatttc atcaaccgga gttgggaatg     1440
gagcacgtac aatacagaaa tgctgatgtc tgagctgagt cctgaagacc agagagtatt     1500
caactttgac gtgcgccagt tgaactggtt ggaatacatt gaaaattatg ttttgggagt     1560
taaaaaatac ttattgaaag aggatatggc tgggatccca aaagcaaagc aacgcttaaa     1620
aaggctccga aatattcact acctctttaa tactgccctc ttccttatcg cctggcgcct     1680
tctcattgca agatctcaga tggctcggaa tgtctggttc ttcattgtaa gcttctgtta     1740
taaattcctc tcctacttta gagcatccag cacgctcaaa gtttaagagc atttagccat     1800
cgccttttat ctggaacctc tcagatacct ctaaaacagc aaactgtgat tctcaagatt     1860
agaaagtaac aaggaatatg cccaaactgt caaatgtcac ctgttatgta ttcgtcccta     1920
ttccttaact atgtattttt atttcagtga gagaaggaaa gttgtaaact agcccatagt     1980
cacctatatt ttagggaaaa aaatccaaat tgtttcctaa cattctattt tatgcccttg     2040
cgtattaaac gtgaaagtac tcccactttt ctatatttag ttttcttttt ctctctgaga     2100
tgattcattt aaactcagta aata                                            2124
```

<210> SEQ ID NO 9
<211> LENGTH: 2955
<212> TYPE: DNA
<213> ORGANISM: Homo sapiens
<220> FEATURE:
<221> NAME/KEY: misc_feature
<223> OTHER INFORMATION: Incyte ID No: 1506182CB1

<400> SEQUENCE: 9

```
ccgggccgct ggtgatctcc ggtagcactc gggccggcgg acagtgaggg cgcgacaaca      60
agggaggtgt cacagttttc catttagatc aacaacttca agttcttacc atggaaaatt     120
ccgagaagac tgaagtggtt ctccttgctt gtggttcatt caatcccatc accaacatgc     180
acctcaggtt gtttgagctg gccaaggact acatgaatgg aacaggaagg tacacagttg     240
tcaaaggcat catctctcct gttggtgatg cctacaagaa gaaggactc attcctgcct      300
atcaccgggg catcatggca gaacttgcta ccaagaattc taaatgggtg aagttgata      360
catgggaaag tcttcagaag gagtggaaag agactctgaa ggtgctaaga caccatcaag     420
agaaattgga ggctagtgac tgtgatcacc agcagaactc acctactcta gaaaggcctg     480
gaaggaagag gaagtggact gaaacacaag attctagtca aaagaaatcc ctagagccaa     540
aaacaaaagc tgtgccaaag gtcaagctgc tgtgtggggc agatttattg gagtcctttg     600
ctgttcccaa tttgtggaag agtgaagaca tcacccaaat cgtggccaac tatgggctca     660
tatgtgttac tcgggctgga aatgatgctc agaagtttat ctatgaatcg gatgtgctgt     720
ggaaacaccg gagcaacatt cacgtggtga atgaatggat cgctaatgac atctcatcca     780
caaaaatccg gagagccctc agaaggggcc agagcattcg ctacttggta ccagatcttg     840
tccaagaata cattgaaaag cataatttgt acagctctga gagtgaagac aggaatgctg     900
gggtcatcct ggccccttg cagagaaaca ctgcagaagc taagacatag gaattctaca     960
gcatgatatt tcagacttcc catttgggga tctgaaacaa tctggagtt aataactggg     1020
gaaagaagtt gtgatctgtt gcctaaacta aagcttaaaa gtttagtaaa atcgtctgg     1080
gcacagtggc tcacgcctgt aatcccagca ctttgggagg ctgaggcagg tggatcacgg    1140
ggtcaggaga tcgagaccat cctggccaat atggtgagac cccatctcta ctaaaaatac    1200
aaaaattagc tgtgtgtggt ggcacgtgcc tgtggtctca gcatgctgag tggctgggat    1260
tacaggcacc cactaccatg tccggctaat tctgtatttt tagtagagat ggggtttcgc    1320
catgttagac aggctggtct tgaactcctg acctcaggtg atctgcccac ctcggccttc    1380
caaagtgctg ggattacagg catgagccac tgcacccagc ctgatcctat tgttgcacta    1440
tttatggagc aacaactttg tacaaagaac aagctttgta cagagaacaa gcttggcttt    1500
ttctcccaac gccgaggatg ctgttgatgc tgccacgtaa tagcataatt ttgggtgtcc    1560
tcaaggacag aacttccact ttgaataatg gaagttagaa caatgaattt cacaggggaa    1620
taaatattaa tgactgacgt gaagaaaata tgccattgtt tattccctcc tgcatcattt    1680
ccataatttg cttttgtact gtcaatttag aggaaatgtg tgatgctggt gttttgtttg    1740
gcctgtttgt ttgatgctgg gggttttatg tgttgtaccc tttaccccctt acattgtgta    1800
atttgaaagt ggcaaacaaa cctgcagtaa aagtccttga ttggcatctt cattcggatg    1860
atggagagcc tttgtggtag tgtttgctta tgtgaacagc aggcctttca gataagagaa    1920
gtggcttttc cttggtgatg aagggggtaga gattgagcca tggggatggt ttaggttaaa    1980
gaatgctttt tttttggcca tcatgaggat ctaacaacag agtagaagga aggatgccct    2040
aggtcagcac gcagggtggt gggagggctt tcatcttcct tacccaagcc tctcttttca    2100
cttttctaga agttcggaag ttgttatatg atgaaatagc ctcctttaac gtttatttct    2160
gggtgccaag ggaggcccat tcctctaaca ttctgataat tcttctcaaa ggcctatgat    2220
ctaaacattt caccatggca tccacttagc tgtggggctg catacacagt ctccacctct    2280
```

-continued

| | |
|---|---|
| gaaatctgaa cttcatttac cagtggtgct gtttgaactt cataatgcca gcacttcctg | 2340 |
| aacacttact gtgtgcctgg cttgtgttcc tgagtgccta atatcacaag gaaacggcaa | 2400 |
| aatcagggga ctggtataag tggtgaagct gggcttgaat ctaagctttg tcttcagagc | 2460 |
| cagtacccct aacctctctt tctgtaaaac attactttc aaagaatgaa gttgtagcca | 2520 |
| aatcttgaaa ttttcattt accctaagtg agaacaaata agtttcagc aaaataataa | 2580 |
| taataataat aatccactat agcttttggt tctctaggcc aaagaaagct ttcacaatca | 2640 |
| ttttttctgt tctttggtct cctggaaagc tttcagtgga agcgatgttt gggacctgga | 2700 |
| gtatgacata gtgggataaa ttcaagttaa acttgaatct gaagcccaac ttgcctcagt | 2760 |
| ttcctcacca ataaattaag ggtcataaga gtatgtgcct catgaaaccg ttgggaaatc | 2820 |
| taaacttgac catctacaaa gtggctggca cagaaacaag tgctcaacac atagacatta | 2880 |
| cagtgatcca ggccacatcc aaccaatgca gagaccaaca gagcctcttc aggatcggga | 2940 |
| acatccagtt aaaat | 2955 |

<210> SEQ ID NO 10
<211> LENGTH: 1579
<212> TYPE: DNA
<213> ORGANISM: Homo sapiens
<220> FEATURE:
<221> NAME/KEY: misc_feature
<223> OTHER INFORMATION: Incyte ID No: 2690842CB1

<400> SEQUENCE: 10

| | |
|---|---|
| tttcaagcca agaaagcttt ccttccccaa agaaagaaat gggtccagta gtgctgacac | 60 |
| actcaagaac ccgcagaaac ccagctaagt tcccagttga gataaaccag tggccctcat | 120 |
| gacactgacg ctcttcccgg tccggctcct ggttgccgct gccatgatgc tgctggcctg | 180 |
| gccctcgca cttgtcgcat cctgggctct gcggagaagg aacccgagca gcccccggcc | 240 |
| ctgtggagga aggttgtgga cttcctgctg aaggccatca tgcgcaccat gtggttcgcc | 300 |
| ggcggcttcc accgggtggc cgtgaagggg cggcaggcgc tgcccaccga ggcggccatc | 360 |
| ctcacgctcg cgcctcactc gtcctacttc gacgccatcc ctgtgaccat gacgatgtcc | 420 |
| tccatcgtga tgaaggcaga gagcagagac atcccgatct ggggaactct gatccagtat | 480 |
| atacggcctg tgttcgtgtc ccggtcagac caggattctc gcaggaaaac agtagaagaa | 540 |
| atcaagagac gggcgcagtc caacggaaag tggccacaga taatgatttt tccagaagga | 600 |
| acttgtacaa acaggacctg cctaattacc ttcaaacctg gtgcattcat ccctggagcg | 660 |
| cccgtccagc ctgtggtttt acgatatcca aataaactgg acaccatcac atggacgtgg | 720 |
| caaggacctg gagcgctgga aatcctgtgg ctcacgctgt gtcagtttca caaccaagtg | 780 |
| gaaatcgagt tccttcctgt gtacagccct tctgaggagg agaagaggaa ccccgcgctg | 840 |
| tatgccagca acgtgcggcg agtcatggcc gaggccttgg gtgtctccgt gactgactac | 900 |
| acgttcgagg actgccagct ggccctggcg gaaggacagc tccgtctccc cgctgacact | 960 |
| tgccttttag aatttgccag gctcgtgcgg ggcctcgggc taaaaccaga aaagcttgaa | 1020 |
| aaagatctgg acagatactc agaaagagcc aggatgaagg gaggagagaa gataggtatt | 1080 |
| gcggagtttg ccgcctccct ggaagtcccc gtttctgact tgctggaaga catgttttca | 1140 |
| ctgttcgacg agagcggcag cggcgaggtg gacctgcgag agtgtgtggt tgccctgtct | 1200 |
| gtcgtctgcc ggccggcccg gaccctggac accatccagc tggctttcaa gacgtacgga | 1260 |
| gcgcaagagg acggcagcgt cggcgaaggt gacctgtcct gcatcctcaa gacggccctg | 1320 |

-continued

| | |
|---|---|
| ggggtggcag agctcaccgt gaccgaccta ttccgagcca ttgaccaaga ggagaagggg | 1380 |
| aagatcacat tcgctgactt ccacaggttt gcagaaatgt accctgcctt cgcagaggaa | 1440 |
| tacctgtacc cggatcagac acatttcgaa agctgtgcag agacctcacc tgcgccaatc | 1500 |
| ccaaacggct tctgtgccga tttcagcccg gaaaactcag acgctgggcg aagcctgtt | 1560 |
| cgcaagaagc tggattagg | 1579 |

<210> SEQ ID NO 11
<211> LENGTH: 3170
<212> TYPE: DNA
<213> ORGANISM: Homo sapiens
<220> FEATURE:
<221> NAME/KEY: misc_feature
<223> OTHER INFORMATION: Incyte ID No: 5027764CB1

<400> SEQUENCE: 11

| | |
|---|---|
| aaaatcccac agtggaaact cttaagcctc tgcgaagtaa atcattcttg tgaatgtgac | 60 |
| acacgatctc tccagtttcc atatgttgag attctactta ttcatcagtt tgttgtgctt | 120 |
| gtcaagatca gacgcagaag aaacatgtcc ttcattcacc aggctgagct ttcacagtgc | 180 |
| agtggttggt acgggactaa atgtgaggct gatgctctac acaaggaaaa acctgacctg | 240 |
| cgcacaaacc atcaactcct cagcttttgg gaacttgaat gtgaccaaga aaaccacctt | 300 |
| cattgtccat ggattcaggc caacaggctc ccctcctgtt tggatggatg acttagtaaa | 360 |
| gggtttgctc tctgttgaag acatgaacgt agttgttgtt gattggaatc gaggagctac | 420 |
| aactttaata tacccatg cctctagtaa gaccagaaaa gtagccatgg tcttgaagga | 480 |
| atttattgac cagatgttgg cagaaggagc ttctcttgat gacatttaca tgatcggagt | 540 |
| aagtctagga gcccacatat ctgggtttgt tggagagatg tacgatggat ggctggggag | 600 |
| aattacaggc ctcgaccctg caggcccttt attcaacggg aaacctcacc aagacagatt | 660 |
| agatcccagt gatgcgcagt tgttgatgt catccattcc gacactgatg cactgggcta | 720 |
| caaggagcca ttaggaaaca tagacttcta cccaaatgga ggattggatc aacctggctg | 780 |
| ccccaaaaca atattgggag gatttcagta ttttaaatgt gaccaccaga ggtctgtata | 840 |
| cctgtacctg tcttccctga gagagagctg caccatcact gcgtatccct gtgactccta | 900 |
| ccaggattat aggaatggca gtgtgtcag ctgcggcacg tcacaaaaag agtcctgtcc | 960 |
| ccttctgggc tattatgctg ataattggaa agaccatcta agggggaaag atcctccaat | 1020 |
| gacgaaggca ttctttgaca cagctgagga gagcccattc tgcatgtatc attactttgt | 1080 |
| ggatattata acatggaaca gaatgtaag aagaggggac attaccatca aattgagaga | 1140 |
| caaagctgga aacaccacag aatccaaaat caatcatgaa cccaccacat ttcagaagta | 1200 |
| tcaccaagtg agtctacttg caagatttaa tcaagatctg gataaagtgg ctgcaatttc | 1260 |
| cttgatgttc tctacaggat ctctaatagg cccaaggtac aagctcagga ttctccgaat | 1320 |
| gaagttaagg tcccttgccc atccggagag gcctcagctg tgtcggtatg atcttgtcct | 1380 |
| gatggaaaac gttgaaacag tcttccaacc tattctttgc ccagagttgc agttgtaact | 1440 |
| gttgccagga cacatggcca taaataatag aaagaaagct acaaccacag gctgtttgaa | 1500 |
| agcttcacct caccttttctg caaggcagaa aaagtatgaa aaaaaccaag ctttttttca | 1560 |
| gtagcgtcct atggatgtca cattgtacat caaacaacct tgtgattata aaacgatccc | 1620 |
| gggaaggagc ccctaactag ggcaagtcag aaatagccag gctcgcagca gcgcagcgct | 1680 |
| gtgtctgctg tgtcctgggg cctcccttgt tccgacctgt caattctgct gcctgtcacg | 1740 |

| | |
|---|---|
| cgggtggttc tgcccatcgc ggctgcgggt caagcatctt caagggaagg acggactgga | 1800 |
| ggcctcaccg tggactcaac tctgcattct ccgtgccaca ttcctccagt tcccacacgt | 1860 |
| agaagggaac gaaactgacg tctacctcat ggggctgctg tgtgggtttg ggaggcaaaa | 1920 |
| atctatgaag ggttttttga atcccatag gtgccacatc tatgagatgt ttgataaatg | 1980 |
| tgaatatgct tttacatttg gcttatcta atttgcaata agagagcctc tctctatcaa | 2040 |
| caccagcttc tctctcgggc tgtttgctca gggaaggcaa aaagccacg tgctggccct | 2100 |
| ctgccttctc taaagtgctg ttggagcatg gaggagctgg aggagatggg gatggactga | 2160 |
| cagctaagag ggcggctgct gggactagat agtggatgaa gaaagaagga cgaggaagcc | 2220 |
| gtggggcagc ctcttcacat ggggacaggg gatggagcat gaggcaaggg aaggaaaagc | 2280 |
| agagcttatt tttcacctaa ggtggagaag gatcactta caggcaacgc tcattttaag | 2340 |
| caacccttaa gaaatgttta tgtttcttta ttaccaatgt aatctatgat tattgaagga | 2400 |
| aatttagaaa atgcgtagat acaaaattaa aaaaaaatac tgtccacgat cctattagag | 2460 |
| gtaattaatg ttagccttt ggaacaaggc tgtcacctat tttgccaaca cgtgaattca | 2520 |
| aaacatgaac cggtttgctt ttggagaatc tgaagactcc agtttgagga atcctttgct | 2580 |
| tccctggagg tagatgctgt ctgcaaatct agaatgacag caggagtcca gtcaagaggt | 2640 |
| cctgtcaggc caaggccaga agaaggag acaatccct ggggcagat gcccagtgtg | 2700 |
| aggggaggca tgatctgtcc catggctgtg gccactgcag gaaggtctgt gaaaaggagg | 2760 |
| tgacaggccc agtcacctcc tcttcaccca agtgattgct ccttcaactg ctatctgtga | 2820 |
| aaatagcctt tgttatgaag aaattgactc tctctctttt tttttttttg gagttgccta | 2880 |
| ggctggagtg caatggtacg atctcagctc actgcaacct ccacctccca ggttcaattg | 2940 |
| attctcctgc ctcagcctcc tgagtagctg ggattacagg catgtgccac cacacccggc | 3000 |
| taattttgt atttttatta gagacagggt ttcaccacgt tagccaggct cgtctcgaac | 3060 |
| tcctgtcctc aggtgactac ccgtctcggc ctcccaaagt gctgggatta caggcatgag | 3120 |
| ccaccacacc cggccaaaaa tggattctct atgtcataaa ttaaaggagt | 3170 |

```
<210> SEQ ID NO 12
<211> LENGTH: 1900
<212> TYPE: DNA
<213> ORGANISM: Homo sapiens
<220> FEATURE:
<221> NAME/KEY: misc_feature
<223> OTHER INFORMATION: Incyte ID No: 2488174CB1

<400> SEQUENCE: 12
```

| | |
|---|---|
| gcgagagaag agaggatgga ccatgcctgg cacactgtgg tgtggagttg gagattctgc | 60 |
| tgggaactcc tcggagctgg gggtcttcca gggacctgat ctctgttgcc gggaacatga | 120 |
| ccgctgccca cagaacatct caccccttgca gtacaactat ggcatccgaa actaccgatt | 180 |
| ccacaccatc tcccactgtg actgtgacac caggtgtagg atgtacggca cagtgcccct | 240 |
| cgctcgcctg cagcccagga ccttctacaa tgcctcctgg agctcccggg ccacctcccc | 300 |
| aactcccagc tcccggagcc cagcccctcc caagcctcga cagaagcagc accttcggaa | 360 |
| ggggccacca catcagaaag ggtccaagcg cccccagcaaa gccaacacca cagccctcca | 420 |
| ggaccctatg gtctctccca ggcttgatgt ggccccaca ggcctccagg gcccacaggg | 480 |
| tggcctaaaa cctcagggtg cccgctgggt ctgccgcagc ttccgccgcc acctggacca | 540 |
| gtgtgagcac cagattgggc cccgggaaat cgagttccag ctgctcaaca gcgcccaaga | 600 |

```
                                                                -continued gccctcttc cactgcaact gcacgcgccg tctggcacgc ttcctgaggc tccacagccc         660
acccgaggtt accaacatgc tttgggagct gctgggcaca acctgcttca agctggcccc        720
tccactggac tgtgtggaag gcaaaaactg ttccagagac cctagggcca tcagggtgtc        780
agcccggcac ttgcggaggc ttcagcagag gcgacaccag ctccaggata aaggcacaga       840
tgagaggcag ccatggcctt cagagcccct gagaggcccc atgtcattct acaaccagtg       900
cctgcagcta acccaggcag ccaggagacc cgacaggcag cagaagtcct ggagccagtg       960
acctcagttt cagctttcct gggcaccagc ctggaccttg cccatggcta tgccaagcct      1020
tgggaatctc agcctcccct ccgtaggtta gactgaagca tggcagaggc tgttgtggac      1080
aatcaagagg atgaatgggg ggatctcaag gcccaaatgc tggaccacat ctcctgctgt      1140
tctgggtaac cttgagctat gtatgacaca actcttctat gcctggatgt ggtgttcagg      1200
aagctcattc tgatgccctg ggctttggcc ttgccaggga acttcacata cagatgagaa      1260
tggggaaagg gtaacttatt gcagcagccc caggcagtac caggaggagg tacatgtatg      1320
tccgtgttgc aaaaataata catgcctcaa aaacctgcct aggggagccc tagtgcctgg      1380
gtgctgtggc ctgaggtagc aggtgggaag ttagggatgt cacagaaatg tctgtgtctg      1440
aatccaggat tggggtgggt gttggagagg gctttcagct cccctcctcc cagggggggcc    1500 tcttttttta acggctgcca tgcccttcct ggcccagccc taaacctaaa ttcaaatctc      1560
ctccatgcct ttgcgcaaag gacctccctc ttgcactcta agccttagtt tcctcctcta      1620
aaaaaagggg gtctctaaac aggagctacc tcatagggtt gttgaggatt aagtgaacca     1680
atacatatac agtgcttagc acttaataag tactccccc tgcgacacct agctgaacta       1740
tggtttggtg tctgatcttg agaggttgat gtaacctttt aaaggcctca gttcgctcac      1800
ctgtgaaatg ggtctaagaa tagcactgat ctcacagggt tgtgatgcag attaaaggag      1860
atggcatgtg taatgtaaaa aaaaaaaaaa aaaaaaaaa                              1900
```

HUMAN PHOSPHOLIPASES

TECHNICAL FIELD

This invention relates to nucleic acid and amino acid sequences of lipid metabolism enzymes and to the use of these sequences in the diagnosis, treatment, and prevention of cancer, neurological disorders, autoimmune/inflammatory disorders, gastrointestinal disorders, and cardiovascular disorders, and in the assessment of the effects of exogenous compounds on the expression of nucleic acid and amino acid sequences of lipid metabolism enzymes.

BACKGROUND OF THE INVENTION

Lipids are water-insoluble, oily or greasy substances that are soluble in nonpolar solvents such as chloroform or ether. Neutral fats (triacylglycerols) serve as major fuels and energy stores. Polar lipids, such as phospholipids, sphingolipids, glycolipids, and cholesterol, are key structural components of cell membranes. (Lipid metabolism is reviewed in Stryer, L. (1995) Biochemistry, W. H. Freeman and Company, New York N.Y.; Lehninger, A. (1982) Principles of Biochemistry, Worth Publishers, Inc. New York N.Y.; and ExPASy "Biochemical Pathways" index of Boehringer Mannheim online publication.)

Fatty acids are long-chain organic acids with a single carboxyl group and a long non-polar hydrocarbon tail. Long-chain fatty acids are essential components of glycolipids, phospholipids, and cholesterol, which are building blocks for biological membranes, and of triglycerides, which are biological fuel molecules. Long-chain fatty acids are also substrates for eicosanoid production, and are important in the functional modification of certain complex carbohydrates and proteins. 16-carbon and 18-carbon fatty acids are the most common. Fatty acid synthesis occurs in the cytoplasm. In the first step, acetyl-Coenzyme A (CoA) carboxylase (ACC) synthesizes malonyl-CoA from acetyl-CoA and bicarbonate. The enzymes which catalyze the remaining reactions are covalently linked into a single polypeptide chain, referred to as the multifunctional enzyme fatty acid synthase (FAS). FAS catalyzes the synthesis of palmitate from acetyl-CoA and malonyl-CoA FAS contains acetyl transferase, malonyl transferase, β-ketoacetyl synthase, acyl carrier protein, β-ketoacyl reductase, dehydratase, enoyl reductase, and thioesterase activities. The final product of the FAS reaction is the 16-carbon fatty acid palmitate. Further elongation, as well as unsaturation, of palmitate by accessory enzymes of the ER produces the variety of long chain fatty acids required by the individual cell. These enzymes include a NADH-cytochrome $b_5$ reductase, cytochrome $b_5$, and a desaturase.

Triacylglycerols, also known as triglycerides and neutral fats, are major energy stores in animals. Triacylglycerols are esters of glycerol with three fatty acid chains. Glycerol-3-phosphate is produced from dihydroxyacetone phosphate by the enzyme glycerol phosphate dehydrogenase or from glycerol by glycerol kinase. Fatty acid-CoA's are produced from fatty acids by fatty acyl-CoA synthetases. Glyercol-3-phosphate is acylated with two fatty acyl-CoA's by the enzyme glycerol phosphate acyltransferase to give phosphatidate. Phosphatidate phosphatase converts phosphatidate to diacylglycerol, which is subsequently acylated to a triacylglyercol by the enzyme diglyceride acyltransferase. Phosphatidate phosphatase and diglyceride acyltransferase form a triacylglyerol synthetase complex bound to the ER membrane.

A major class of phospholipids are the phosphoglycerides, which are composed of a glycerol backbone, two fatty acid chains, and a phosphorylated alcohol. Phosphoglycerides are components of cell membranes. Principal phosphoglycerides are phosphatidyl choline, phosphatidyl ethanolamine, phosphatidyl serine, phosphatidyl inositol, and diphosphatidyl glycerol. Many enzymes involved in phosphoglyceride synthesis are associated with membranes (Meyers, R. A. (1995) Molecular Biology and Biotechnology, VCH Publishers Inc., New York N.Y., pp. 494-501). Phosphatidate is converted to CDP-diacylglycerol by the enzyme phosphatidate cytidylyltransferase (ExPASy ENZYME EC 2.7.7.41). Transfer of the diacylglycerol group from CDP-diacylglycerol to serine to yield phosphatidyl serine, or to inositol to yield phosphatidyl inositol, is catalyzed by the enzymes CDP-diacylglycerol-serine O-phosphatidyltransferase and CDP-diacylglycerol-inositol 3-phosphatidyltransferase, respectively (ExPASy ENZYME EC 2.7.8.8; ExPASy ENZYME EC 2.7.8.11). The enzyme phosphatidyl serine decarboxylase catalyzes the conversion of phosphatidyl serine to phosphatidyl ethanolamine, using a pyruvate cofactor (Voelker, D. R. (1997) Biochim. Biophys. Acta 1348: 236-244). Phosphatidyl choline is formed using diet-derived choline by the reaction of CDP-choline with 1,2-diacylglycerol, catalyzed by diacylglycerol cholinephosphotransferase (ExPASy ENZYME 2.7.8.2).

Cholesterol, composed of four fused hydrocarbon rings with an alcohol at one end, moderates the fluidity of membranes in which it is incorporated. In addition, cholesterol is used in the synthesis of steroid hormones such as cortisol, progesterone, estrogen, and testosterone. Bile salts derived from cholesterol facilitate the digestion of lipids. Cholesterol in the skin forms a barrier that prevents excess water evaporation from the body. Farnesyl and geranylgeranyl groups, which are derived from cholesterol biosynthesis intermediates, are post-translationally added to signal transduction proteins such as Ras and protein-targeting proteins such as Rab. These modifications are important for the activities of these proteins (Guyton, A. C. (1991) Textbook of Medical Physiology, W. B. Saunders Company, Philadelphia Pa., pp. 760-763; Stryer, supra, pp. 279-280, 691-702, 934). Mammals obtain cholesterol derived from both de novo biosynthesis and the diet.

Sphingolipids are an important class of membrane lipids that contain sphingosine, a long chain amino alcohol. They are composed of one long-chain fatty acid, one polar head alcohol, and sphingosine or sphingosine derivatives. The three classes of sphingolipids are sphingomyelins, cerebrosides, and gangliosides. Sphingomyelins, which contain phosphocholine or phosphoethanolamine as their head group, are abundant in the myelin sheath surrounding nerve cells. Galactocerebrosides, which contain a glucose or galactose head group, are characteristic of the brain. Other cerebrosides are found in non-neural tissues. Gangliosides, whose head groups contain multiple sugar units, are abundant in the brain, but are also found in non-neural tissues.

Eicosanoids, including prostaglandins, prostacyclin, thromboxanes, and leukotrienes, are 20-carbon molecules derived from fatty acids. Eicosanoids are signaling molecules which have roles in pain, fever, and inflammation. The precursor of all eicosanoids is arachidonate, which is generated from phospholipids by phospholipase $A_2$ and from diacylglycerols by diacylglycerol lipase. Leukotrienes are produced from arachidonate by the action of lipoxygenases.

Within cells, fatty acids are transported by cytoplasmic fatty acid binding proteins (Online Mendelian Inheritance in Man (OMIM) *134650 Fatty Acid-Binding Protein 1, Liver;

FABP1). Diazepam binding inhibitor (DBI), also known as endozepine and acyl CoA-binding proteins is an endogenous γ-aminobutyric acid (GABA) receptor ligand which is thought to down-regulate the effects of GABA. DBI binds medium- and long-chain acyl-CoA esters with very high affinity and may function as an intracellular carrier of acyl-CoA esters (OMIM *25950 Diazepam Binding Inhibitor; DBI; PROSITE PDOC00686 Acyl-CoA-binding protein signature).

Fat stored in liver and adipose triglycerides may be released by hydrolysis and transported in the blood. Free fatty acids are transported in the blood by albumin. Triacylglycerols and cholesterol esters in the blood are transported in lipoprotein particles. The particles consist of a core of hydrophobic lipids surrounded by a shell of polar lipids and apolipoproteins. The protein components serve in the solubilization of hydrophobic lipids and also contain cell-targeting signals. Lipoproteins include chylomicrons, chylomicron remnants, very-low-density lipoproteins (VLDL), intermediate-density lipoproteins (IDL), low-density lipoproteins (LDL), and high-density lipoproteins (HDL). There is a strong inverse correlation between the levels of plasma HDL and risk of premature coronary heart disease.

Mitochondrial and peroxisomal beta-oxidation enzymes degrade saturated and unsaturated fatty acids by sequential removal of two-carbon units from CoA-activated fatty acids. The main beta-oxidation pathway degrades both saturated and unsaturated fatty acids while the auxiliary pathway performs additional steps reed for the degradation of unsaturated fatty acids. The pathways of mitochondrial and peroxisomal beta-oxidation use similar enzymes, but have different substrate specificities and functions. Mitochondria oxidize short-, medium-, and long-chain fatty acids to produce energy for cells. Mitochondrial beta-oxidation is a major energy source for cardiac and skeletal muscle. In liver, it provides ketone bodies to the peripheral circulation when glucose levels are low as in starvation, endurance exercise, and diabetes (Eaton, S. et al. (1996) Biochem. J. 320:345-357). Peroxisomes oxidize medium-, long-, and very-long-chain fatty acids, dicarboxylic fatty acids, branched fatty acids, prostaglandins, xenobiotics, and bile acid intermediates. The chief roles of peroxisomal beta-oxidation are to shorten toxic lipophilic carboxylic acids to facilitate their excretion and to shorten very-long-chain fatty acids prior to mitochondrial beta-oxidation (Mannaerts, G. P. and P. P. Van Veldhoven (1993) Biochimie 75:147-158). Enzymes involved in beta-oxidation include acyl CoA synthetase, carnitine acyltransferase, acyl CoA dehydrogenases, enoyl CoA hydratases, L-3-hydroxyacyl CoA dehydrogenase, β-ketothiolase, 2,4-dienoyl CoA reductase, and isomerase.

Three classes of lipid metabolism enzymes are discussed in further detail. The three classes are lipases, phospholipases and lipoxygenases.

Lipases

Triglycerides are hydrolyzed to fatty acids and glycerol by lipases. Adipocytes contain lipases that break down stored triacylglycerols, releasing fatty adds for export to other tissues where they are required as fuel. Lipases are widely distributed in animals, plants, and prokaryotes. Triglyceride lipases (ExPASy ENZYME EC 3.1.1.3), also known as triacylglycerol lipases and tributyrases, hydrolyze the ester bond of triglycerides. In higher vertebrates there are at least three tissue-specific isozymes including gastric, hepatic, and pancreatic lipases. These three types of lipases are structurally closely related to each other as well as to lipoprotein lipase. The most conserved region in gastric, hepatic, and pancreatic lipases is centered around a serine residue which is also present in lipases of prokaryotic origin. Mutation in the serine residue renders the enzymes inactive. Gastric, hepatic, and pancreatic lipases hydrolyze lipoprotein triglycerides and phospholipids. Gastric lipases in the intestine aid in the digestion and absorption of dietary fats. Hepatic lipases are bound to and act at the endothelial surfaces of hepatic tissues. Hepatic lipases also play a major role in the regulation of plasma lipids. Pancreatic lipase requires a small protein cofactor, colipase, for efficient dietary lipid hydrolysis. Colipase binds to the C-terminal, non-catalytic domain of lipase, thereby stabilizing an active conformation and considerably increasing the overall hydrophobic binding site. Deficiencies of these enzymes have been identified in man, and all are associated with pathologic levels of circulating lipoprotein particles (Gargouri, Y. et al. (1989) Biochim. Biophys. Acta 1006:255-271; Connelly, P. W. (1999) Clin. Chim. Acta 286:243-255; van Tilbeurgh, H. et al. (1999) Biochim Biophys Acta 1441:173-184).

Lipoprotein lipases (ExPASy ENZYME EC 3.1.1.34), also known as clearing factor lipases, diglyceride lipases, or diacylglycerol lipases, hydrolyze triglycerides and phospholipids present in circulating plasma lipoproteins, including chylomicrons, very low and intermediate density lipoproteins, and high-density lipoproteins (HDL). Together with pancreatic and hepatic lipases, lipoprotein lipases (LPL) share a high degree of primary sequence homology. Both lipoprotein lipases and hepatic lipases are anchored to the capillary endothelium via glycosaminoglycans and can be released by intravenous administration of heparin. LPLs are primarily synthesized by adipocytes, muscle cells, and macrophages. Catalytic activities of LPLs are activated by apolipoprotein C-II and are inhibited by high ionic strength conditions such as 1 M NaCl. LPL deficiencies in humans contribute to metabolic diseases such as hypertriglyceridemia, HDL2 deficiency, and obesity (Jackson, R. L. (1983) in *The Enzymes* (Boyer, P. D., ed.) Vol. XVI, pp. 141-186, Academic Press, New York N.Y.; Eckel, R. H. (1989) New Engl. J. Med. 320:1060-1068).

Phospholipases

Phospholipases, a group of enzymes that catalyze the hydrolysis of membrane phospholipids, are classified according to the bond cleaved in a phospholipid. They are classified into PLA1, PLA2, PLB, PLC, and PLD families. Phospholipases are involved in many inflammatory reactions by making arachidonate available for eicosanoid biosynthesis. More specifically, arachidonic acid is processed into bioactive lipid mediators of inflammation such as lyso-platelet-activating factor and eicosanoids. The synthesis of arachidonic acid from membrane phospholipids is the rate-limiting step in the biosynthesis of the four major classes of eicosanoids (prostaglandins, prostacyclins, thromboxanes and leukotrienes) which are involved in pain, fever, and inflammation (Kaiser, E. et al. (1990) Clin. Biochem. 23:349-370). Furthermore, leukotriene-B4 is known to function in a feedback loop which further increases PLA2 activity (Wijkander, J. et al. (1995) J. Biol. Chem. 270:26543-26549).

The secretory phospholipase $A_2$ (PLA2) superfamily comprises a number of heterogeneous enzymes whose common feature is to hydrolyze the sn-2 fatty acid acyl ester bond of phosphoglycerides. Hydrolysis of the glycerophospholipids releases free fatty acids and lysophospholipids. PLA2 activity generates precursors for the biosynthesis of biologically active lipids, hydroxy fatty acids, and platelet-activating factor. PLA2s were first described as components of snake venoms, and were later characterized in numerous species, PLA2s have traditionally been classified into several major groups and subgroups based on their amino acid sequences, divalent cation requirements, and location of disulfide bonds. The PLA2s of Groups I, II, and III consist of low molecular weight, secreted, $Ca^{2+}$-dependent proteins. Group IV PLA2s are primarily 85-kDa, $Ca^{2+}$-dependent cytosolic phospholipases. Finally, a number of $Ca^{2+}$-independent PLA2s have been described, which comprise Group V (Davidson, F. F. and E. A. Dennis (1990) J. Mol. Evol. 31:228-238; and Dennis, E. F. (1994) J. Biol Chem. 269: 13057-13060).

The first PLA2s to be extensively characterized were the Group I, II, and III PLA2s found in snake and bee venoms. These venom PLA2s share many features with mammalian PLA2s including a common catalytic mechanism, the same $Ca^{2+}$ requirement, and conserved primary and tertiary structures. In addition to their role in the digestion of prey, the venom PLA2s display neurotoxic, myotoxic, anticoagulant, and proinflammatory effects in mammalian tissues. This diversity of pathophysiological effects is due to the presence of specific, high affinity receptors for these enzymes on various cells and tissues (Lambeau, G. et al. (1995) J. Biol. Chem. 270:5534-5540).

PLA2s from Groups I, IIA, IIC, and V have been described in mammalian and avian cells, and were originally characterized by tissue distribution, although the distinction is no longer absolute. Thus, Group I PLA2s were found in the pancreas, Group IIA and IIC were derived from inflammation-associated tissues (e.g., the synovium), and Group V were from cardiac tissue. The pancreatic PLA2s function in the digestion of dietary lipids and have been proposed to play a role in cell proliferation, smooth muscle contraction, and acute lung injury. The Group II inflammatory PLA2s are potent mediators of inflammatory processes and are highly expressed in serum and synovial fluids of patients with inflammatory disorders. These Group II PLA2s are found in most human ca types assayed and are expressed in diverse pathological processes such as septic shock, intestinal cancers, rheumatoid arthritis, and epidermal hyperplasia. A Group V PLA2 has been cloned from brain tissue and is strongly expressed in heart tissue. A human PLA2 was recently cloned from fetal lung, and based on its structural properties, appears to be the first member of a new group of mammalian PLA2s, referred to as Group X. Other PLA2s have been cloned from various human tissues and cell lies, suggest a large diversity of PLA2s (Chen, J. et al. (1994) J. Biol. Chem. 269:2365-2368; Kennedy, B. P. et al. (1995) J. Biol. Chem. 270: 22378-22385; Komada, M. et al. (1990) Biochem. Biophys. Res. Common 168:1059-1065; Cupillard, L. et al. (1997) J. Biol. Chem. 272:15745-15752; and Nalefski, E. A. et al. (1994) J. Biol. Chem. 269:18239-18249).

Phospholipases B (PLB) (ExPASy ENZYME EC 3.1.1.5), also known as lysophospholipase, lecithinase B, or lysolecithinase are widely distributed enzymes that metabolize intracellular lipids, and occur in numerous isoforms. Small isoforms, approximately 15-30 kD, function as hydrolases; large isoforms, those exceeding 60 kD, function both as hydrolases and transacylases. A particular substrate for PLBs, lysophosphatidylcholine, causes lysis of cell membranes when it is formed or imported into a cell. PLBs are regulated by lipid factors including acylcarnitine, arachidonic acid, and phosphatidic acid. These lipid factors are signaling molecules important in numerous pathways, including the inflammatory response (Anderson, R. et al. (1994) Toxicol. Appl. Pharmacol. 125:176-183; Selle, H. et al. (1993); Eur. J. Biochem. 212:4411-16).

Phospholipase C (PLC) (ExPASy ENZYME EC 3.1.4.10) plays an important role in transmembrane signal transduction. Many extracellular signaling molecules including hormones, growth factors, neurotransmitters, and immunoglobulins bind to their respective cell surface receptors and activate PLCs. The role of an activated PLC is to catalyze the hydrolysis of phosphatidyl-inositol-4,5-bisphosphate (PIP2), a minor component of the plasma membrane, to produce diacylglycerol and inositol 1,4,5-trisphosphate (IP3). In their respective biochemical pathways, IP3 and diacylglycerol serve as second messengers and trigger a series of intracellular responses. IP3 induces the release of $Ca^{2+}$ from internal cellular storage, and diacylglycerol activates protein kinase C (PKC). Both pathways are part of transmembrane signal transduction mechanisms which regulate cellular processes which include secretion, neural activity, metabolism, and proliferation.

Several distinct isoforms of PLC have been identified and are categorized as PLC-beta, PLC-gamma, and PLC-delta. Subtypes are designated by adding Arabic numbers after the Greek letters, eg. PLC-$\beta$-1. PLCs have a molecular mass of 62-68 kDa, and their amino acid sequences show two regions of significant similarity. The first region designated X has about 170 amino acids, and the second or Y region contains about 260 amino acids.

The catalytic activities of the three isoforms of PLC are dependent upon $Ca^{2+}$. It has been suggested that the binding sites for $Ca^{2+}$ in the PLCs are located in the Y-region, one of two conserved regions. The hydrolysis of common inositol-containing phospholipids, such as phosphatidylinositol (PI), phosphatidylinositol 4-monophosphate (PIP), and phosphatidylinositol 4,5-bisphosphate (PIP2), by any of the isoforms yields cyclic and noncyclic inositol phosphates (Rhee, S. G. and Y. S. Bae (1997) J. Biol. Chem. 272:15045-15048).

All mammalian PLCs contain a pleckstrin homology (PH) domain which is about 100 amino acids in length and is composed of two antiparallel beta sheets flanked by an amphipatic alpha helix. PH domains target PLCs to the membrane surface by interacting with either the beta/gamma subunits of G proteins or PIP2 (PROSITE PDOC50003).

Phospholipase D (PLD) (ExPASy ENZYME EC 3.1.4.4), also known as lecithinase D, lipophosphodiesterase II, and choline phosphatase catalyzes the hydrolysis of phosphatidylcholine and other phospholipids to generate phosphatidic add. PLD plays an important role in membrane vesicle trafficking, cytoskeletal dynamics, and transmembrane signal transduction. In addition, the activation of PLD is involved in cell differentiation and growth (reviewed in Liscovitch, M. (2000) Biochem. J. 345:401-415).

PLD is activated in mammalian cells in response to diverse stimuli that include hormones, neurotransmitters, growth factors, cytokines, activators of protein kinase C, and agonists binding to G-protein-coupled receptors. At least two forms of mammalian PLD, PLD1 and PLD2, have been identified PLD1 is activated by protein kinase C alpha and by the small GTPases ARF and RhoA. (Houle, M. G. and S. Bourgoin (1999) Biochim. Biophys. Acta 1439:135-149). PLD2 can be selectively activated by unsaturated fatty acids such as oleate (Kim J. H. (1999) FEBS Lett. 454:42-46).

Lipoxygenases

Lipoxygenases (ExPASy ENZYME EC 1.13.11.12) are non-heme iron-containing enzymes that catalyze the dioxygenation of certain polyunsaturated fatty acids such as lipoproteins. Lipoxygenases are found widely in plants, fungi, and animals. Several different lipoxygenase enzymes are known, each having a characteristic oxidation action. In animals, there are specific lipoxygenases that catalyze the dioxygenation of arachidonic acid at the carbon-3, 5, 8, 11, 12, and 15 positions. These enzymes are named after the position of arachidonic acid that they dioxygenate. Lipoxygenases have a single polypeptide chain with a molecular mass of ~75-80 kDa in animals. The proteins have an N-terminal-barrel domain and a larger catalytic domain containing a single atom of non-heme iron. Oxidation of the ferric enzyme to an active form is required for catalysis (Yamamoto, S. (1992) Biochim. Biophys. Acta 1128:117-131; Brash, A. R. (1999) J. Biol. Chem. 274:23679-23682). A variety of lipoxygenase inhibitors exist and are classified into five major categories according to their mechanism of inhibition. These include antioxidants, iron chelators, substrate analogues, lipoxygenase-activating protein inhibitors, and, finally, epidermal growth factor-receptor inhibitors.

3-Lipoxygenase, also known as e-LOX-3 or Aloxe3 has recently been cloned from murine epidermis. Aloxe3 resides on mouse chromosome 11, and the deduced amino acid sequence for Aloxe3 is 54% identical to the 12-lipoxygenase sequences (Kinzig, A. (1999) Genomics 58:158-164).

5-Lipoxygenase (5-LOX, ExPASy ENZYME EC 1.13.11.34), also known as arachidonate:oxygen 5-oxidoreductase, is found primarily in white blood cells, macrophages, and mast cells. 5-LOX converts arachidonic acid first to 5-hydroperoxyeicosatetraenoic acid (5-HPETE) and then to leukotriene (LTA4 (5,6-oxido-7,9,11,14-eicosatetraenoic acid)). Subsequent conversion of leukotriene A4 by leukotriene A4 hydrolase yields the potent neutrophil chemoattractant leukotriene B4. Alternatively, conjugation of LTA4 with glutathione by leukotriene C4 synthase plus downstream metabolism leads to the cysteinyl leukotrienes that influence airway reactivity and mucus secretion, especially in asthmatics. Most lipoxygenases require no other cofactors or proteins for activity. In contrast, the mammalian 5-LOX requires calcium and ATP, and is activated in the presence of a 5-LOX activating protein (FLAP). FLAP itself binds to arachidonic acid and supplies 5-LOX with substrate (Lewis, R. A. et al. (1990) New Engl. J. Med. 323:645-655). The expression levels of 5-LOX and FLAP are found to be increased in the lungs of patients with plexogenic (primary) pulmonary hypertension (Wright, L. et al. (1998) Am. J. Respir. Crit. Care Med. 157:219-229).

12-Lipoxygenase (12-LOX, ExPASy ENZYME: EC 1.13.11.31) oxygenates arachidonic acid to form 12-hydroperoxyeicosatetraenoic acid (12-HPETE). Mammalian 12-lipoxygenases are named after the prototypical tissues of their occurrence (hence, the leukocyte, platelet, or epidermal types). Platelet-type 12-LOX has been found to be the predominant isoform in epidermal skin specimens and epidermoid cells. Leukocyte 12-LOX was first characterized extensively from porcine leukocytes and was found to have a rather broad distribution in mammalian tissues by immunochemical assays. Besides tissue distribution, the leukocyte 12-LOX is distinguished from the platelet-type enzyme by its ability to form 15-HPETE, in addition to 12-HPETE from arachidonic acid substrate. Leukocyte 12-LOX is highly related to 15-lipoxygenase (15-LOX) in that both are dual specificity lipoxygenases, and they are about 85% identical in primary structure in higher mammals. Leukocyte 12-LOX is found in tracheal epithelium, leukocytes, and macrophages (Conrad, D. J. (1999) Clin. Rev. Allergy Immunol. 17:71-89).

15-Lipoxygenase (15-LOX; ExPASy ENZYME: EC 1.13.11.33) is found inhuman reticulocytes, airway epithelium, and eosinophils. 15-LOX has been detected in atherosclerotic lesions in mammals, specifically rabbit and man. The enzyme, in addition to its role in oxidative modification of lipoproteins, is important in the inflammatory reaction in atherosclerotic lesions. 15-LOX has been shown to be induced in human monocytes by the cytokine IL-4, which is known to be implicated in the inflammatory process (Kuhn, H. and S. Borngraber (1999) Adv. Exp. Med. Biol. 447:5-28).

Disease Correlation

Lipid metabolism is involved in human diseases and disorders. In the arterial disease atherosclerosis, fatty lesions form on the inside of the atrial wall. These lesions promote the loss of arterial flexibility and the formation of blood clots (Guyton, supra). In Tay-Sachs disease, the $GM_2$ ganglioside (a sphingolipid) accumulates in lysosomes of the central nervous system due to a lack of the enzyme N-acetylhexosaminidase. Patients suffer nervous system degeneration leading to early death (Fauci, A. S. et al. (1998) *Harrison's Principles of Internal Medicine*, McGraw-Hill, New York N.Y., p. 2171). The Niemann-Pick diseases are caused by defects in lipid metabolism. Niemann-Pick diseases types A and B are caused by accumulation of sphingomyelin (a sphingolipid) and or lipids in the central nervous system due to a defect in the enzyme sphingomyelinase, leading to neurodegeneration and lung disease. Niemann-Pick disease type C results from a defect in cholesterol transport, leading to the accumulation of sphingomyelin and cholesterol in lysosomes and a secondary reduction in sphingomyelinase activity. Neurological symptoms such as grand mal seizures, ataxia, and loss of previously learned speech, manifest 1-2 years after birth. A mutation in the NPC protein, which contains a putative cholesterol-sensing domain, was found in a mouse model of Niemann-Pick disease type C (Fauci, supra, p. 2175; Loftus, S. K. et al. (1997) Science 277:232-235).

PLAs are implicated in a variety of disease processes. For example, PLAs are found in the pancreas, in cardiac tissue, and in inflammation-associated tissues. Pancreatic PLAs function in the digestion of dietary lipids and have been propose to play a role in cell proliferation, smooth muscle contraction, and acute lung injury. Inflammatory PLAs are potent mediators of inflammatory processes and are highly expressed in serum and synovial fluids of patients with inflammatory disorders. Additionally, inflammatory PLAs are found in most human cell types and are expressed in diverse pathological processes such as septic shock, intestinal cancers, rheumatoid arthritis, and epidermal hyperplasia.

The role of PLBs in human tissues has been investigated in various research studies. Hydrolysis of lysophosphatidylcholine by PLBs causes lysis in erythrocyte membranes (Selle, supra). Similarly, Endresen, M. J. et al. (1993; Scand. J. Clin. Invest. 53:733-739) reported that the increased hydrolysis of lysophosphatidylcholine by PLB in pre-eclamptic women causes release of free fatty acids into the sera. In renal studies, PLB was shown to protect $Na^+,K^+$-ATPase from the cytotoxic and cytolytic effects of cyclosporin A (Anderson, supra).

Lipases, phospholipases, and lipoxygenases are thought to contribute to complex diseases, such as atherosclerosis, obesity, arthritis, asthma, and cancer, as well as to single gene defects, such as Wolman's disease and Type I hyperlipoproteinemia.

The discovery of new lipid metabolism enzymes and the polynucleotides encoding them satisfies a need in the art by providing new compositions which are useful in the diagnosis, prevention, and treatment of cancer, neurological disorders, autoimmune/inflammatory disorders, gastrointestinal disorders, and cardiovascular disorders, and in the assessment of the effects of exogenous compounds on the expression of nucleic acid and amino acid sequences of lipid metabolism enzymes.

SUMMARY OF THE INVENTION

The invention features purified polypeptides, lipid metabolism enzymes, referred to collectively as "LME" and individually as "LME-1," "LME-2," "LME-3," "LME-4," "LME-5," and "LME-6." In one aspect, the invention provides an isolated polypeptide comprising an amino acid sequence selected from the group consisting of a) an amino acid sequence selected from the group consisting of SEQ ID NO:1-6, b) a naturally occurring amino acid sequence having at least 90% sequence identity to an amino acid sequence selected from the group consisting of SEQ ID NO:1-6, c) a biologically active fragment of an amino acid sequence selected from the group consisting of SEQ ID NO:1-6, and d) an immunogenic fragment of an amino acid sequence selected from the group consisting of SEQ ID NO:1-6. In one alternative, the invention provides an isolated polypeptide comprising the amino acid sequence of SEQ ID NO:1-6.

The invention further provides an isolated polynucleotide encoding a polypeptide comprising an amino acid sequence selected from the group consisting of a) an amino acid sequence selected from the group consisting of SEQ ID NO:1-6, b) a naturally occurring amino acid sequence having at least 90% sequence identity to an amino acid sequence selected from the group consisting of SEQ ID NO:1-6, c) a biologically active fragment of amino acid sequence selected from the group consisting of SEQ ID NO:1-6, and d) an immunogenic fragment of an amino acid sequence selected from the group consisting of SEQ ID NO:1-6. In one alternative, the polynucleotide encodes a polypeptide selected from the group consisting of SEQ ID NO:1-6. In another alternative, the polynucleotide is selected from the group consisting of SEQ ID NO:7-12.

Additionally, the invention provides a recombinant polynucleotide comprising a promoter sequence operably linked to a polynucleotide encoding a polypeptide comprising an amino acid sequence selected from the group consisting of a) an amino acid sequence selected from the group consisting of SEQ ID NO:1-6, b) a naturally occurring amino acid sequence having at least 90% sequence identity to an amino acid sequence selected from the group consisting of SEQ ID NO:1-6, c) a biologically active fragment of an amino acid sequence selected from the group consisting of SEQ ID NO:1-6, and d) an immunogenic fragment of an amino acid sequence selected from the group consisting of SEQ ID NO:1-6. In one alternative, the invention provides a cell transformed with the recombinant polynucleotide. In another alternative, the invention provides a transgenic organism comprising the recombinant polynucleotide.

The invention also provides a method for producing a polypeptide comprising an amino acid sequence selected from the group consisting of a) an amino acid sequence selected from the group consisting of SEQ ID NO:1-6, b) a naturally occurring amino acid sequence having at least 90% sequence identity to an amino acid sequence selected from the group consisting of SEQ ID NO:1-6, c) a biologically active fragment of an amino acid sequence selected from the group consisting of SEQ ID NO:1-6, and d) an immunogenic fragment of an amino acid sequence selected from the group consisting of SEQ ID NO:1-6. The method comprises a) culturing a cell under conditions suitable for expression of the polypeptide, wherein said cell is transformed with a recombinant polynucleotide comprising a promoter sequence operably linked to a polynucleotide encoding the polypeptide, and b) recovering the polypeptide so expressed.

Additionally, the invention provides an isolated antibody which specifically binds to a polypeptide comprising an amino acid sequence selected from the group consisting of a) an amino acid sequence selected from the group consisting of SEQ ID NO:1-6, b) a naturally occurring amino acid sequence having at least 90% sequence identity to a amino acid sequence selected from the group consisting of SEQ ID NO:1-6, c) a biologically active fragment of an amino acid sequence selected from the group consisting of SEQ ID NO:1-6, and d) an immunogenic fragment of an amino acid sequence selected from the group consisting of SEQ ID NO:1-6.

The invention further provides an isolated polynucleotide comprising a polynucleotide sequence selected from the group consisting of a) a polynucleotide sequence selected from the group consisting of SEQ ID NO:7-12, b) a naturally occurring polynucleotide sequence having at least 90% sequence identity to a polynucleotide sequence selected from the group consisting of SEQ ID NO:7-12, c) a polynucleotide sequence complementary to a), d) a polynucleotide sequence complementary to b), and e) an RNA equivalent of a)-d). In one alternative, the polynucleotide comprises at least 60 contiguous nucleotides.

Additionally, the invention provides a method for detecting a target polynucleotide in a sample, said target polynucleotide having a sequence of a polynucleotide comprising a polynucleotide sequence selected from the group consisting of a) a polynucleotide sequence selected from the group consisting of SEQ ID NO:7-12, b) a naturally occurring polynucleotide sequence having at least 90% sequence identity to a polynucleotide sequence selected from the group consisting of SEQ ID NO:7-12, c) a polynucleotide sequence complementary to a), d) a polynucleotide sequence complementary to b), and e) an RNA equivalent of a)-d). The method comprises a) hybridizing the sample with a probe comprising at least 20 contiguous nucleotides comprising a sequence complementary to said target polynucleotide in the sample, and which probe specifically hybridizes to said target polynucleotide, under conditions whereby a hybridization complex is formed between said probe and said target polynucleotide or fragments thereof, and b) detecting the presence or absence of said hybridization complex, and optionally, if present, the amount thereof. In one alternative, the probe comprises at least 60 contiguous nucleotides.

The invention further provides a method for detecting a target polynucleotide in a sample, said target polynucleotide having a sequence of a polynucleotide comprising a polynucleotide sequence selected from the group consisting of a) a polynucleotide sequence selected from the group consisting of SEQ ID NO:7-12, b) a naturally occurring polynucleotide sequence having at least 90% sequence identity to a polynucleotide sequence selected from the group consisting of SEQ ID NO:7-12, c) a polynucleotide sequence complementary to a), d) a polynucleotide sequence complementary to b), and e) an RNA equivalent of a)-d). The method comprises a) amplifying said target polynucleotide or fragment thereof using polymerase chain reaction amplification, and b) detecting the presence or absence of said amplified target polynucleotide or fragment thereof, and, optionally, if present, the amount thereof.

The invention further provides a composition comprising an effective amount of a polypeptide comprising an amino acid sequence selected from the group consisting of a) an amino acid sequence selected from the group consisting of SEQ ID NO:1-6, b) a naturally occurring amino acid sequence having at least 90% sequence identity to an amino acid sequence selected from the group consisting of SEQ ID NO:1-6, c) a biologically active fragment of an amino acid sequence selected from the group consisting of SEQ ID NO:1-6, and d) an immunogenic fragment of an amino acid sequence selected from the group consisting of SEQ ID NO:1-6, and a pharmaceutically acceptable excipient. In one embodiment, the composition comprises an amino acid sequence selected from the group consisting of SEQ ID NO:1-6. The invention additionally provides a method of treating a disease or condition associated with decreased expression of functional LME, comprising administering to a patient in need of such treatment the composition.

The invention also provides a method for screening a compound for effectiveness as an agonist of a polypeptide comprising an amino acid sequence selected from the group consisting of a) an amino acid sequence selected from the group consisting of SEQ ID NO:1-6, b) a naturally occurring amino acid sequence having at least 90% sequence identity to an amino acid sequence selected from the group consisting of SEQ ID NO:1-6, c) a biologically active fragment of an amino acid sequence selected from the group consisting of SEQ ID NO:1-6, and d) an immunogenic fragment of an amino acid sequence selected from the group consisting of SEQ ID NO:1-6. The method comprises a) exposing a sample comprising the polypeptide to a compound, and b) detecting agonist activity in the sample. In one alternative, the invention provides a composition comprising an agonist compound identified by the method and a pharmaceutically acceptable excipient. In another alternative, the invention provides a method of treating a disease or condition associated with decreased expression of functional LME, comprising administering to a patient in need of such treatment the composition.

Additionally, the invention provides a method for screening a compound for effectiveness as an antagonist of a polypeptide comprising an amino acid sequence selected from the group consisting of a) an amino acid sequence selected from the group consisting of SEQ ID NO:1-6, b) a naturally occurring amino acid sequence having at least 90% sequence identity to an amino acid sequence selected from the group consisting of SEQ ID NO:1-6, c) a biologically active fragment of an amino acid sequence selected from the group consisting of SEQ ID NO:1-6, and d) an immunogenic fragment of an amino acid sequence selected from the group consisting of SEQ ID NO:1-6. The method comprises a) exposing a sample comprising the polypeptide to a compound, and b) detecting antagonist activity in the sample. In one alternative, the invention provides a composition comprising an antagonist compound identified by the method and a pharmaceutically acceptable excipient. In another alternative, the invention provides a method of treating a disease or condition associated with overexpression of functional LME, comprising administering to a patient in need of such treatment the composition.

The invention further provides a method of screening for a compound that specifically binds to a polypeptide comprising an amino acid sequence selected from the group consisting of a) an amino acid sequence selected from the group consisting of SEQ ID NO:1-6, b) a naturally occurring amino acid sequence having at least 90% sequence identity to an amino acid sequence selected from the group consisting of SEQ ID NO:1-6, c) a biologically active fragment of an ammo acid sequence selected from the group consisting of SEQ ID NO:1-6, and d) an immunogenic fragment of an amino acid sequence selected from the group consisting of SEQ ID NO:1-6. The method comprises a) combining the polypeptide with at least one test compound under suitable conditions, and b) detecting binding of the polypeptide to the test compound, thereby identifying a compound that specifically binds to the polypeptide.

The invention further provides a method of screening for a compound that modulates the activity of a polypeptide comprising an amino acid sequence selected from the group consisting of a) an amino acid sequence selected from the group consisting of SEQ ID NO:1-6, b) a naturally occurring amino acid sequence having at least 90% sequence identity to an amino acid sequence selected from the group consisting of SEQ ID NO:1-6, c) a biologically active fragment of an amino acid sequence selected from the group consisting of SEQ ID NO:1-6, and d) an immunogenic fragment of an amino acid sequence selected from the group consisting of SEQ ID NO:1-6. The method comprises a) combining the polypeptide with at least one test compound under conditions permissive for the activity of the polypeptide, b) assessing the activity of the polypeptide in the presence of the test compound, and c) comparing the activity of the polypeptide in the presence of the test compound with the activity of the polypeptide in the absence of the test compound, wherein a change in the activity of the polypeptide in the presence of the test compound is indicative of a compound that modulates the activity of the polypeptide.

The invention further provides a method for screening a compound for effectiveness in altering expression of a target polynucleotide, wherein said target polynucleotide comprises a sequence selected from the group consisting of SEQ ID NO:7-12, the method comprising a) exposing a sample comprising the target polynucleotide to a compound, and b) detecting altered expression of the target polynucleotide.

The invention further provides a method for assessing toxicity of a test compound, said method comprising a) treating a biological sample containing nucleic acids with the test compound; b) hybridizing the nucleic acids of the treated biological sample with a probe comprising at least 20 contiguous nucleotides of a polynucleotide comprising a polynucleotide sequence selected from the group consisting of i) a polynucleotide sequence selected from the group consisting of SEQ ID NO:7-12, ii) a naturally occurring polynucleotide sequence having at least 90% sequence identity to a polynucleotide sequence selected from the group consisting of SEQ ID NO:7-12, iii) a polynucleotide sequence complementary to i), iv) a polynucleotide sequence complementary to ii), and v) an RNA equivalent of i)-iv). Hybridization occurs under conditions whereby a specific hybridization complex is formed between said probe and a target polynucleotide in the biological sample, said target polynucleotide comprising a polynucleotide sequence selected from the group consisting of i) a polynucleotide sequence selected from the group consisting of SEQ ID NO:7-12, ii) a naturally occurring polynucleotide sequence having at least 90% sequence identity to a polynucleotide sequence selected from the group consisting of SEQ ID NO:7-12, ii) a polynucleotide sequence complementary to i), iv) a polynucleotide sequence complementary to ii), and v) an RNA equivalent of i)-iv). Alternatively, the target polynucleotide comprises a fragment of a polynucleotide sequence selected from the group consisting of i)-v) above; c) quantifying the amount of hybridization complex; and d) comparing the amount of hybridization complex in the treated biological sample with the amount of hybridization complex in an untreated biological sample, wherein a difference in the amount of hybridization complex in the treated biological sample is indicative of toxicity of the test compound.

BRIEF DESCRIPTION OF THE TABLES

Table 1 summarizes the nomenclature for the full length polynucleotide and polypeptide sequences of the present invention.

Table 2 shows the GenBank identification number and annotation of the nearest GenBank homolog for polypeptides of the invention. The probability score for the match between each polypeptide and its GenBank homolog is also shown.

Table 3 shows structural features of polypeptide sequences of the invention, including predicted motifs and domains, along with the methods, algorithms, and searchable databases used for analysis of the polypeptides.

Table 4 lists the cDNA fragments which were used to assemble polynucleotide sequences of the invention, along with selected fragments of the polynucleotide sequences.

Table 5 shows the representative cDNA library for polynucleotides of the invention.

Table 6 provides an appendix which describes the tissues and vectors used for construction of the cDNA libraries shown in Table 5.

Table 7 shows the tools, programs, and algorithms used to analyze the polynucleotides and polypeptides of the invention, along with applicable descriptions, references, and threshold parameters.

DESCRIPTION OF THE INVENTION

Before the present proteins, nucleotide sequences, and methods are described, it is understood that this invention is not limited to the particular machines, materials and methods described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any machines, materials, and methods similar or equivalent to those described herein can be used to practice or test the present invention, the preferred machines, materials and methods are now described. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

Definitions

"LME" refers to the amino acid sequences of substantially purified LME obtained from any species, particularly a mammalian species, including bovine, ovine, porcine, murine, equine, and human, and from any source, whether natural, synthetic, semi-synthetic, or recombinant.

The term "agonist" refers to a molecule which intensifies or mimics the biological activity of LME. Agonists may include proteins, nucleic acids, carbohydrates, small molecules, or any other compound or composition which modulates the activity of LME either by directly interacting with LME or by acting on components of the biological pathway in which LME participates.

A "allelic variant" is an alternative form of the gene encoding LME. Allelic variants may result from at least one mutation in the nucleic acid sequence and may result in altered mRNAs or in polypeptides whose structure or function may or may not be altered. A gene may have none, one, or many allelic variants of its naturally occurring form. Common mutational changes which give rise to allelic variants are generally ascribed to natural deletions, additions, or substitutions of nucleotides. Each of these types of changes may occur alone, or in combination with others, one or more times in a given sequence.

"Altered" nucleic acid sequences encoding LME include those sequences with deletions, insertions, or substitutions of different nucleotides, resulting in a polypeptide the same as LME or a polypeptide with at least one functional characteristic of LME. Included with this definition are polymorphisms which may or may not be readily detectable using a particular of oligonucleotide probe of the polynucleotide encoding LME, and improper or unexpected hybridization to allelic variants, with a locus other than the normal chromosomal locus for the polynucleotide sequence encoding LME. The encoded protein may also be "altered," and may contain deletions, insertions, or substitutions of amino acid residues which produce a silent change and result in a functionally equivalent LME. Deliberate amino acid substitutions may be made on the basis of similarity in polarity, charge, solubility, hydrophobicity, hydrophilicity, and/or the amphipathic nature of the residues, as long as the biological or immunological activity of LME is retained. For example, negatively charged amino acids may include aspartic acid and glutamic acid, and positively charged amino acids may include lysine and arginine. Amino acids with uncharged polar side chains having similar hydrophilicity values may include: asparagine and glutamine; and serine and threonine. Amino acids with uncharged side chains having similar hydrophilicity values may include: leucine, isoleucine, and valine; glycine and alanine; and phenylalanine and tyrosine.

The terms "amino acid" and "amino acid sequence" refer to an oligopeptide, peptide, polypeptide, or protein sequence, or a fragment of any of these, and to naturally occurring or synthetic molecules. Where "amino acid sequence" is recited to refer to a sequence of a naturally occurring protein molecule, "amino acid sequence" and like terms are not mean to limit the amino acid sequence to the complete native amino acid sequence associated with the recited protein molecule.

"Amplification" relates to the production of additional copies of a nucleic acid sequence. Amplification is generally carried out using polymerase chain reaction (PCR) technologies well known in the art.

The term "antagonist" refers to a molecule which inhibits or attenuates the biological activity of LME. Antagonists may include proteins such as antibodies, nucleic acids, carbohydrates, small molecules, or any other compound or composition which modulates the activity of LME either by directly interacting with LME or by acting on components of the biological pathway in which LME participates.

The term "antibody" refers to intact immunoglobulin molecules as well as to fragments thereof, such as Fab, F(ab')$_2$, and Fv fragments, which are capable of binding an epitopic determinant. Antibodies that bind LME polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant" refers to that region of a molecule (i.e., an epitope) that makes contact with a particular antibody. When a protein or a fragment of a protein is used to immunize a host animal, numerous regions of the protein may induce the production of antibodies which bind specifically to antigenic determinants (particular regions or three-dimensional structures on the protein). An antigenic determinant may compete wt the intact antigen (i.e., the immunogen used to elicit the immune response) for binding to an antibody.

The term "antisense" refers to any composition capable of base-paring with we "sense" (coding) stand of a specific nucleic acid sequence. Antisense compositions may include DNA; RNA; peptide nucleic acid (PNA); oligonucleotides having modified backbone linkages such as phosphorothioates, methylphosphonates, or benzylphosphonates; oligonucleotides having modified sugar groups such as 2'-methoxyethyl sugars or 2'-methoxyethoxy sugars; or oligonucleotides having modified bases such as 5-methyl cytosine, 2'-deoxyuracil, or 7-deaza-2'-deoxyguanosine. Antisense molecules may be produced by any method including chemical synthesis or transcription. Once introduced into a cell, the complementary antisense molecule base-pairs with a naturally occurring nucleic acid sequence produced by the cell to form duplexes which block either transcription or translation. The designation "negative" or "minus" can refer to the antisense strand, and the designation "positive" or "plus" can refer to the sense strand of a reference DNA molecule.

The term "biologically active" refers to a protein having structural, regulatory, or biochemical functions of a naturally occurring molecule. Likewise, "immunologically active" or "immunogenic" refers to the capability of the natural, recombinant, or synthetic LME, or of any oligopeptide thereof, to induce a specific immune response in appropriate animals or cells and to bind with specific antibodies.

"Complementary" describes the relationship between two single-stranded nucleic acid sequences that anneal by base-pairing. For example, 5'-AGT-3' pairs with its complement, 3'-TCA-5'.

A "composition comprising a given polynucleotide sequence" and a "composition comprising a given amino acid sequence" refer broadly to any composition containing the given polynucleotide or amino acid sequence. The composition may comprise a dry formulation or an aqueous solution. Compositions comprising polynucleotide sequences encoding LME or fragments of LME may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., sodium dodecyl sulfate, SDS), and other components (e.g., Denhardt's solution, dry milk salmon sperm DNA, etc.).

"Consensus sequence" refers to a nucleic acid sequence which has been subjected to repeated DNA sequence analysis to resolve uncalled bases, extended using the XL-PCR kit (Applied Biosystems, Foster City Calif.) in the 5' and/or the 3' direction, and resequenced, or which has been assembled from one or more overlapping cDNA, EST, or genomic DNA fragments using a computer program for fragment assembly, such as the GEL VIEW fragment assembly system (GCG, Madison Wis.) or Phrap (University of Washington, Seattle Wash.). Some sequences have been both extended and assembled to produce the consensus sequence.

"Conservative amino acid substitutions" are those substitutions that are predict to least interfere with the properties of the original protein i.e., the structure and especially the function of the protein is conserved and not significantly changed by such substitutions. The table blow shows amino acids which may be substituted for an original amino acid in a protein and which are regarded as conservative amino acid substitutions.

| Original Residue | Conservative Substitution |
| --- | --- |
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

A "deletion" refers to a change in the amino add or nucleotide sequence that results in the absence of one or more amino acid residues or nucleotides.

The term "derivative" refers to a chemically modified polynucleotide or polypeptide. Chemical modifications of a polynucleotide can include, for example, replacement of hydrogen by an alkyl, acyl, hydroxyl, or amino group. A derivative polynucleotide encodes a polypeptide which retains at least one biological or immunological function of the natural molecule. A derivative polypeptide is one modified by glycosylation, pegylation or any similar process that retains at least one biological or immunological function of the polypeptide from which it was derived.

A "detectable label" refers to a reporter molecule or enzyme that is capable of generating a measurable signal and is covalently or noncovalently joined to a polynucleotide or polypeptide.

A "fragment" is a unique portion of LME or the polynucleotide encoding LYE which is identical in sequence to but shorter in length than the parent sequence. A fragment may comprise up to the entire length of the defined sequence, minus one nucleotide/amino acid residue. For example, a fragment may comprise from 5 to 1000 contiguous nucleotides or amino acid residues. A fragment used as a probe, primer, antigen, therapeutic molecule, or for other purposes, may be at least 5, 10, 15, 16, 20, 25, 30, 40, 50, 60, 75, 100, 150, 250 or at least 500 contiguous nucleotides or amino acid residues in length. Fragments may be preferentially selected from certain regions of a molecule. For example, a polypeptide fragment may comprise a certain length of contiguous amino acids selected from the first 250 or 500 amino acids (or first 25% or 50%) of a polypeptide as shown in a certain defined sequence. Clearly these lengths are exemplary, and any length that is supported by the specification, including the Sequence Listing, tables, and figures, may be encompassed by the present embodiments.

A fragment of SEQ ID NO:7-12 comprises a region of unique polynucleotide sequence that specifically identifies SEQ ID NO:7-12, for example, as distinct from any other sequence in the genome from which the fragment was obtained. A fragment of SEQ ID NO:7-12 is useful, for example, in hybridization and amplification technologies and in analogous methods that distinguish SEQ ID NO:7-12 from related polynucleotide sequences. The precise length of a fragment of SEQ ID NO:7-12 and the region of SEQ ID NO:7-12 to which the fragment corresponds are routinely determinable by one of ordinary skill in the art based on the intended purpose for the fragment.

A fragment of SEQ ID NO:1-6 is encoded by a fragment of SEQ ID NO:7-12, A fragment of SEQ ID NO:1-6 comprises a region of unique amino acid sequence that specifically identifies SEQ ID NO:1-6. For example, a fragment of SEQ ID NO:1-6 is useful as an immunogenic peptide for the development of antibodies that specifically recognize SEQ ID NO:1-6. The precise length of a fragment of SEQ ID NO; 1-6 and the region of SEQ ID NO:1-6 to which the fragment corresponds are routinely determinable by one of ordinary skill in the at based on the intended purpose for the fragment.

A "full length" polynucleotide sequence is one containing at least a translation initiation codon (e.g., methionine) followed by an open reading frame and a translation termination codon. A "full length" polynucleotide sequence encodes a "full length" polypeptide sequence.

"Homology" refers to sequence similarity or, interchangeably, sequence identity, between two or more polynucleotide sequences or two or more polypeptide sequences.

The terms "percent identity" and "% identity," as applied to polynucleotide sequences, refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences.

Percent identity between polynucleotide sequences may be determined using the default parameters of the CLUSTAL V algorithm as incorporated into the MEGALIGN version 3.12e sequence alignment program. This program is part of the LASERGENE software package, a suite of molecular biological analysis programs (DNASTAR, Madison Wis.). CLUSTAL V is described in Higgins, D. G. and P. M. Sharp (1989) CABIOS 5:151-153 and in Higgins, D. G. et al. (1992) CABIOS 8:189-191. For pairwise alignments of polynucleotide sequences, the default parameters are set as follows: Ktuple=2, gap penalty=5, window=4, and "diagonals saved"=4. The "weighted" residue weight table is selected as the default. Percent identity is reported by CLUSTAL V as the "percent similarity" between aligned polynucleotide sequences.

Alernatively, a suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 2 15:403-4 10), which is available from several sources, including the NCBI, Bethesda, Md., and on the Internet. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively on the internet. The "BLAST 2 Sequences" tool can be used for both blastn and blastp (discussed below). BLAST programs are commonly used with gap and other parameters set to default settings. For example, to compare two nucleotide sequences, one may use blastn with the "BLAST 2 Sequences" tool Version 2.0.12 (Apr. 21, 2000) set at default parameters. Such default parameters may be, for example:

Matrix: BLOSUM62
Reward for match: 1
Penalty for mismatch: −2
Open Gap: 5 and Extension Gap: 2 penalties
Gap x drop-off: 50
Expect 10
Word Size: 11
Filter: on Percent identity may be measured over the length of an entire defined sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

Nucleic acid sequences that do not show a high degree of identity may nevertheless encode similar amino acid sequences due to the degeneracy of ale genetic code. It is understood that changes in a nucleic acid sequence can be made using this degeneracy to produce multiple nucleic acid sequences that all encode substantially the same protein.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (and therefore function) of the polypeptide.

Percent identity between polypeptide sequences may be determined using the default parameters of the CLUSTAL V algorithm as incorporated into the MEGALIGN version 3.12e sequence alignment program (described and referenced above). For pairwise alignments of polypeptide sequences using CLUSTAL V, the default parameters are set as follows: Ktuple=1, gap penalty=3, window=5, and "diagonals saved"=5. The PAM250 matrix is selected as the default residue weight table. As with polynucleotide alignments, the percent identity is reported by CLUSTAL V as the "percent similarity" between aligned polypeptide sequence pairs.

Alternatively the NCBI BLAST software suite may be used. For example, for a pairwise comparison of two polypeptide sequences, one may use the "BLAST 2 Sequences" tool Version 2.0.12 (Apr. 21, 2000) with blastp set at default parameters. Such default parameters may be, for example:

Matrix: BLOSUM62
Open Gap: 11 and Extension Gap: 1 penalties
Gap x drop-off: 50
Expect: 10
Word Size: 3
Filter: on Percent identity may be measured over the length of an entire defied polypeptide sequence, for example, as defined by a particular SEQ ID number, or may be measured over a shorter length, for example, over the length of a fragment taken from a larger, defied polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

"Human artificial chromosomes" (HACs) are linear microchromosomes which may contain DNA sequences of about 6 kb to 10 Mb in size and which contain all of the elements required for chromosome replication, segregation and maintenance.

The term "humanized antibody" refers to an antibody molecule in which the amino acid sequence in the non-antigen binding regions has been altered so that the antibody more closely resembles a human antibody, and shill retains its original binding ability.

"Hybridization" refers to the process by which a polynucleotide strand anneals with a complementary strand through base pairing under defined hybridization conditions. Specific hybridization is an indication that two nucleic acid sequences share a high degree of complementarity. Specific hybridization complexes form under permissive annealing conditions and remain hybridized after the "washing" step(s). The washing step(s) is particularly important in determining the stringency of the hybridization process, with more stringent conditions allowing less non-specific binding, i.e., binding between pairs of nucleic acid stands that are not perfectly matched. Permissive conditions for annealing of nucleic acid sequences are routinely determinable by one of ordinary skill in the art and may be consistent among hybridization experiments, whereas wash conditions may be varied among experiments to achieve the desired stringency, and therefore hybridization specificity. Permissive annealing conditions occur, for example, at 68° C. in the presence of about 6×SSC, about 1% (w/v) SDS, and about 100 μg/ml sheared, denatured salmon sperm DNA.

Generally, stringency of hybridization is expressed, in part, with reference to the temperature under which the wash step is carried out. Such wash temperatures are typically selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. An equation for calculating $T_m$ and conditions for nucleic acid hybridization are well known and can be found in Sambrook, J. et al. (1989) *Molecular Cloning: A Laboratory Manual*, $2^{nd}$ ed., vol. 1-3, Cold Spring Harbor Press, Plainview N.Y.; specifically see volume 2, chapter 9.

High stringency conditions for hybridization between polynucleotides of the present invention include wash conditions of 68° C. in the presence of about 0.2×SSC and about 0.1% SDS, for 1 hour. Alternatively, temperatures of about 65° C., 60° C., 55° C., or 42° C. may be used SSC concentration may be varied from about 0.1 to 2×SSC, with SDS being present at about 0.1%. Typically, blocking reagents are used to block non-specific hybridization. Such blocking reagents include, for instance, sheared and denatured salmon sperm DNA at about 100-200 μg/ml. Organic solvent, such as formamide at a concentration of about 35-50% v/v, may also be used under particular circumstances, such as for RNA:DNA hybridizations. Useful variations on these wash conditions mill be readily apparent to those of ordinary skill in the art. Hybridization, particularly under high stringency conditions, may be suggestive of evolutionary similarity between the nucleotides. Such similarity is strongly indicative of a similar role for the nucleotides and their encoded polypeptides.

The term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes filters, chips, pins or glass slides, or any other appropriate substrate to which cells or their nucleic acids have been fixed).

The words "insertion" and "addition" refer to changes in an amino acid or nucleotide sequence resulting in the addition of one or more amino acid residues or nucleotides, respectively.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

An "immunogenic fragment" is a polypeptide or oligopeptide fragment of LME which is capable of eliciting an immune response when introduced into a living organism, for example, a mammal. The term "immunogenic fragment" also includes any polypeptide or oligopeptide fragment of LME which is useful in any of the antibody production methods disclosed herein or known in the art.

The term "microarray" refers to an arrangement of a plurality of polynucleotides, polypeptides, or other chemical compounds on a substrate.

The terms "element" and "array element" refer to a polynucleotide, polypeptide, or other chemical compound having a unique and defined position on a microarray.

The term "modulate" refers to a change in the activity of LME. For example, modulation may cause an increase or a decrease in protein activity, binding characteristics, or any other biological, functional, or immunological properties of LME.

The phrases "nucleic acid" and "nucleic acid sequence" refer to a nucleotide, oligonucleotide, polynucleotide, or any fragment thereof. These phrases also refer to DNA or RNA of genomic or synthetic origin which may be single-stranded or double-stranded and may represent the sense or the antisense stand, to peptide nucleic acid (PNA), or to any DNA-like or RNA-like material.

"Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame.

"Peptide nucleic acid" (PNA) refers to an antisense molecule or anti-gene agent which comprises an oligonucleotide of at least about 5 nucleotides in length linked to a peptide backbone of amino acid residues ending in lysine. The terminal lysine confers solubility to the composition PNAs preferentially bind complementary single stranded DNA or RNA and stop transcript elongation, and may be pegylated to extend their lifespan in the cell.

"Post-translational modification" of an LME may involve lipidation, glycosylation, phosphorylation, acetylation, racemization, proteolytic cleavage, and other modifications known in the art. These processes may occur synthetically or biochemically. Biochemical modifications will vary by cell type depending on the enzymatic milieu of LME.

"Probe" refers to nucleic acid sequences encoding LME, their complements, or fragments thereof, which are used to detect identical, allelic or related nucleic acid sequences. Probes are isolated oligonucleotides or polynucleotides attached to a detectable label or reporter molecule. Typical labels include radioactive isotopes, ligands, chemiluminescent agents, and enzymes. "Primers" are short nucleic acids, usually DNA oligonucleotides, which may be annealed to a target polynucleotide by complementary base-pairing. The primer may then be extended along the target DNA strand by a DNA polymerase enzyme. Primer pairs can be used for amplification (and identification) of a nucleic acid sequence, e.g., by the polymerase chain reaction (PCR).

Probes and primers as used in the present invention typically comprise at least 15 contiguous nucleotides of a known sequence. In order to enhance specificity, longer probes and primers may also be employed such as probes and primers that comprise at least 20, 25, 30, 40, 50, 60, 70, 80, 90, 100, or at least 150 consecutive nucleotides of the disclosed nucleic acid sequences. Probes and primers may be considerably longer than these examples, and it is understood that any length supported by the specification, including the tables, figures, and Sequence Listing, may be used.

Methods for preparing and using probes and primers are described in the references, for example Sambrook, J. et al. (1989) *Molecular Cloning: A Laboratory Manual*, 2$^{nd}$ ed., vol. 1-3, Cold Spring Harbor Press, Plainview N.Y.; Ausubel, F. M. et al. (1987) *Current Protocols in Molecular Biology*, Greene Publ. Assoc. & Wiley-Intersciences, New York N.Y.; Innis, M. et al. (1990) *PCR Protocols, A Guide to Methods and Applications*, Academic Press, San Diego Calif. PCR primer pairs can be derived from a known sequence for example, by using computer programs intended for that purpose such as Primer (Version 0.5, 1991, Whitehead Institute for Biomedical Research, Cambridge Mass.).

Oligonucleotides for use as primers are selected using software known in the art for such purpose. For example, OLIGO 4.06 software is useful for the selection of PCR primer pairs of up to 100 nucleotides each, and for the analysis of oligonucleotides and larger polynucleotides of up to 5,000 nucleotides from an input polynucleotide sequence of up to 32 kilobases. Similar primer selection programs have incorporated additional features for expanded capabilities. For example, the PrimOU primer selection program (available to the public from the Genome Center at University of Texas South West Medical Center, Dallas Tex.) is capable of choosing specific primers from megabase sequences and is thus useful for designing primers on a genome-wide scope. The Primer3 primer selection program (available to the public from the Whitehead Institute/MIT Center for Genome Research, Cambridge Mass.) allows the user to input a "mispriming library," in which sequences to avoid as primer binding sites are user-specified. Primer3 is useful, in particular, for the selection of oligonucleotides for microarrays. (The source code for the latter two primer selection programs may also be obtained from their respective sources and modified to meet the user's specific needs.) The PrimeGen program (available to the public from the UK Human Genome Mapping Project Resource Centre, Cambridge UK) designs primers based on multiple sequence alignments, thereby allowing selection of primers that hybridize to either the most conserved or least conserved regions of aligned nucleic acid sequences. Hence, this program is useful for identification of both unique and conserved oligonucleotides and polynucleotide fragments. The oligonucleotides and polynucleotide fragments identified by any of the above selection methods are useful in hybridization technologies, for example, as PCR or sequencing primers, microarray elements, or specific probes to identify fully or partially complementary polynucleotides in a sample of nucleic acids. Methods of oligonucleotide selection are not limited to those described above.

A "recombinant nucleic acid" is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques such as those described in Sambrook, supra. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

Alternatively, such recombinant nucleic acids may be part of a viral vector e.g., based on a vaccinia virus, that could be use to vaccinate a mammal wherein the recombinant nucleic acid is expressed, inducing a protective immunological response in the mammal.

A "regulatory element" refers to a nucleic acid sequence usually derived from untranslated regions of a gene and includes enhancers, promoters, introns, and 5' and 3', untranslated regions (UTRs). Regulatory elements interact with host or viral proteins which control transcription, translation, or RNA stability.

"Reporter molecules" are chemical or biochemical moieties used for labeling a nucleic acid, amino acid, or antibody. Reporter molecules include radionuclides; enzymes; fluorescent, chemiluminescent, or chromogenic agents; substrates; cofactors; inhibitors; magnetic particles; and other moieties known in the art.

An "RNA equivalent," in reference to a DNA sequence, is composed of the same linear sequence of nucleotides as the reference DNA sequence with the exception that all occurrences of the nitrogenous base thymine are replaced with uracil and the sugar backbone is composed of ribose instead of deoxyribose.

The term "sample" is used in its broadest sense. A sample suspected of containing LME, nucleic acids encoding LME, or fragments thereof may comprise a bodily fluid; an extract from a cell, chromosome, organelle, or membrane isolated from a cell; a cell; genomic DNA, RNA, or cDNA, in solution or bound to a substrate; a tissue; a tissue print; etc.

The terms "specific binding" and "specifically binding" refer to that interaction between a protein or peptide and an agonist, an antibody, an antagonist, a small molecule, or any natural or synthetic binding composition. The interaction is dependent upon the presence of a particular structure of the protein, e.g., the antigenic determinant or epitope, recognized by the binding molecule. For example, if an antibody is specific for epitope "A," the presence of a polypeptide comprising the epitope A, or the presence of free unlabeled A, in a reaction containing free labeled A and the antibody will reduce the amount of labeled A that binds to the antibody.

The term "substantially purified" refers to nucleic acid or amino acid sequences that are removed from their natural environment and are isolated or separated, and are at least 60% free, preferably at least 75% free, and most preferably at least 90% free from other components with which they are naturally associated.

A "substitution" refers to the replacement of one or more amino acid residues or nucleotides by different amino acid residues or nucleotides, respectively.

"Substrate" refers to any suitable rigid or semi-rigid support including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which polynucleotides or polypeptides are bound.

A "transcript image" refers to the collective pattern of gene expression by a particular cell type or tissue under given conditions at a given time.

"Transformation" describes a process by which exogenous DNA is introduced into a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, bacteriophage or viral infection, electroporation, heat shock, lipofection, and particle bombardment. The term "transformed cells" includes stably transformed cells in which the inserted DNA is capable of replication either as an autonomously replicating plasmid or as part of the host chromosome, as well as transiently transformed cells which express the inserted DNA or RNA for limited periods of time.

A "transgenic organism," as used herein, is any organism, including but not limited to animals and plants, in which one or more of the cells of the organism contains heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. The transgenic organisms contemplated in accordance with the present invention include bacteria, cyanobacteria, fungi, plants and animals. The isolated DNA of the present invention can be introduced into the host by methods known in the art, for example infection, transfection, transformation or transconjugation. Techniques for transferring the DNA of the present invention into such organisms are widely known and provided in references such as Sambrook et al. (1989), supra.

A "variant" of a particular nucleic acid sequence is defined as a nucleic acid sequence having at least 40% sequence identity to the particular nucleic acid sequence over a certain length of one of the nucleic acid sequences using blastn with the "BLAST 2 Sequences" tool Version 2.0.9 (May 7, 1999) set at default parameters. Such a pair of nucleic acids may show, for example, at least 50%, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length. A variant may be described as, for example, an "allelic" (as defined above), "splice," "species," or "polymorphic" variant A splice variant may have significant identity to a reference molecule, but will generally have a greater or lesser number of polynucleotides due to alternative splicing of exons during mRNA processing. The corresponding polypeptide may possess additional functional domains or lack domains that are present in the reference molecule. Species variants are polynucleotide sequences that vary from one species to another. The resulting polypeptides will generally have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one nucleotide base. The presence of SNPs may be indicative of, for example, a certain population, a disease state, or a propensity for a disease state.

A "variant" of a particular polypeptide sequence is defined as a polypeptide sequence having at least 40% sequence identity to the particular polypeptide sequence over a certain length of one of the polypeptide sequences using blastp with the "BLAST 2 Sequences" tool Version 2.0.9 (May 7, 1999) set at default parameters. Such a pair of polypeptides may show, for example, at least 50%, at least 60%, at least 70%, at least 80%, at least 90%, at least 91%, at least 92%, at least 93%, at least 94%, at least 95%, at least 96%, at least 97%, at least 98%, or at least 99% or greater sequence identity over a certain defined length of one of the polypeptides.

The Invention

The invention is based on the discovery of new human lipid metabolism enzymes (LME), the polynucleotides encoding LME, and the use of these compositions for the diagnosis, treatment, or prevention of cancer, neurological disorders, autoimmune/inflammatory disorders, gastrointestinal disorders, and cardiovascular disorders.

Table 1 summarizes the nomenclature for the full length polynucleotide and polypeptide sequences of the invention. Each polynucleotide and its corresponding polypeptide are correlated to a single Incyte project identification number (Incyte Project ID). Each polypeptide sequence is denoted by both a polypeptide sequence identification number (Polypeptide SEQ ID NO:) and an Incyte polypeptide sequence number (Incyte Polypeptide ID) as shown. Each polynucleotide sequence is denoted by both a polynucleotide sequence identification number (Polynucleotide SEQ ID NO:) and an Incyte polynucleotide consensus sequence number (Incyte Polynucleotide ID) as shown.

Table 2 shows sequences with homology to the polypeptides of the invention as identified by BLAST analysis against the GenBank protein (genpept) database. Columns 1 and 2 show the polypeptide sequence identification number (Polypeptide SEQ ID NO:) and the corresponding Incyte polypeptide sequence number (Incyte Polypeptide ID) for polypeptides of the invention. Column 3 shows the GenBank identification number (Genbank ID NO:) of the nearest GenBank homolog. Column 4 shows the probability score for the match between each polypeptide and its GenBank homolog. Column 5 shows the annotation of the GenBank homolog along with relevant citations where applicable, all of which are expressly incorporated by reference herein.

Table 3 shows various structural features of the polypeptides of the invention. Columns 1 and 2 show the polypeptide sequence identification number (SEQ ID NO:) and the corresponding Incyte polypeptide sequence number (Incyte Polypeptide ID) for each polypeptide of the invention. Column 3 shows the number of amino acid residues in each polypeptide. Column 4 shows potential phosphorylation sites, and column 5 shows potential glycosylation sites, as determined by the MOTIFS program of the GCG sequence analysis software package (Genetics Computer Group, Madison Wis.). Column 6 shows amino acid residues comprising signature sequences, domains, and motifs. Column 7 shows analytical methods for protein structure/function analysis and in some cases, searchable databases to which the analytical methods were applied.

Together, Tables 2 and 3 summarize the properties of polypeptides of the invention, and these properties establish that the claimed polypeptides are lipid metabolism enzymes. For example, SEQ ID NO:1 is 50% identical, from residue N63 to residue H300, to a *C. elegans* protein having similarity to human enoyl-CoA hydratase (GenBank ID g3876901) as determined by the Basic Local Alignment Search Tool (BLAST). (See Table 2.) The BLAST probability score is 2.50E-56, which indicates the probability of obtaining the observed polypeptide sequence alignment by chance. SEQ ID NO:1 also contains an enoyl-CoA hydratase/isomerase family domain as determined by searching for statistically significant matches in the hidden Markov model (HMM)-based PFAM database of conserved protein family domains. (See Table 3.) Data from BLIMPS and PROFILESCAN analyses provide further corroborative evidence that SEQ ID NO:1 is an enoyl-CoA hydratase. SEQ ID NO:2, SEQ ID NO:3, SEQ ID NO:4, SEQ ID NO:5, and SEQ ID NO:6 were analyzed and annotated in a similar manner. The algorithms and parameters for the analysis of SEQ ID NO:1-6 are described in Table 7.

As shown in Table 4, the full length polynucleotide sequences of the present invention were assembled using cDNA sequences or coding (exon) sequences derived from genomic DNA, or any combination of these two types of sequences. Columns 1 and 2 list the polynucleotide sequence identification number (Polynucleotide SEQ ID NO:) and the corresponding Incyte polynucleotide consensus sequence number (Incyte Polynucleotide ID) for each polynucleotide of the invention. Column 3 shows the length of each polynucleotide sequence in basepairs. Column 4 lists fragments of the polynucleotide sequences which are useful, for example, in hybridization or amplification technologies that identify SEQ ID NO:7-12 or that distinguish between SEQ ID NO:7-12 and related polynucleotide sequences. Column 5 shows identification numbers corresponding to cDNA sequences, coding sequences (exons) predicted from genomic DNA, and/or sequence assemblages comprised of both cDNA and genomic DNA. These sequences were used to assemble the full length polynucleotide sequences of the invention. Columns 6 and 7 of Table 4 show the nucleotide start (5') and stop (3') positions of the cDNA sequences in column 5 relative to their respective full length sequences.

The identification numbers in Column 5 of Table 4 may refer specifically, for example, to Incyte cDNAs along with their corresponding cDNA libraries. For example, 6827519J1 is the identification number of an Incyte cDNA sequence, and SINTNOR01 is the cDNA library from which it is derived. Incyte cDNAs for which cDNA libraries are not indicated were derived from pooled cDNA libraries (e.g., 71530085V1). Alternatively, the identification numbers in column 5 may refer to GenBank cDNAs or ESTs which contributed to the assembly of the full length polynucleotide sequences. Alternatively, the identification numbers in column 5 may refer to coding regions predicted by Genscan analysis of genomic DNA. The Genscan-predicted coding sequences may have been edited prior to assembly. (See Example IV.) Alternatively, the identification numbers in column 5 may refer to assemblages of both cDNA and Genscan-predicted exons brought together by an "exon stitching" algorithm. (See Example V.) Alternatively, the identification numbers in column 5 may refer to assemblages of both cDNA and Genscan-predicted exons brought together by an "exon-stretching" algorithm. (See Example V.) In some cases, Incyte cDNA coverage redundant with the sequence coverage shown in column 5 was obtained to confirm the final consensus polynucleotide sequence, but the relevant Incyte cDNA identification numbers are not shown.

Table 5 shows the representative cDNA libraries for those full length polynucleotide sequences which were assembled using Incyte cDNA sequences. The representative cDNA library is the Incyte cDNA library which is most frequently represented by the Incyte cDNA sequences which were used to assemble and confirm the above polynucleotide sequences. The tissues and vectors which were used to construct the cDNA libraries shown in Table 5 are described in Table 6.

The invention also encompasses LME variants. A preferred LME variant is one which has at least about 80%, or alternatively at least about 90%, or even at least about 95% amino acid sequence identity to the LME amino acid sequence, and which contains at least one functional or structural characteristic of LME.

The invention also encompasses polynucleotides which encode LME. In a particular embodiment, the invention encompasses a polynucleotide sequence comprising a sequence selected from the group consisting of SEQ ID NO:7-12, which encodes LME. The polynucleotide sequences of SEQ ID NO:7-12, as presented in the Sequence Listing, embrace the equivalent RNA sequences, wherein occurrences of the nitrogenous base thymine are replaced with uracil, and the sugar backbone is composed of ribose instead of deoxyribose.

The invention also encompasses a variant of a polynucleotide sequence encoding LME. In particular, such a variant polynucleotide sequence will have at least about 70%, or alternatively at least about 85%, or even at least about 95% polynucleotide sequence identity to the polynucleotide sequence encoding LME. A particular aspect of the invention encompasses a variant of a polynucleotide sequence comprising a sequence selected from the group consisting of SEQ ID NO:7-12 which has at least about 70%, or alternatively at least about 85%, or even at least about 95% polynucleotide sequence identity to a nucleic acid sequence selected from the group consisting of SEQ ID NO:7-12. Any one of the polynucleotide variants described above can encode an amino acid sequence which contains at least one functional or structural characteristic of LME.

It will be appreciated by those skilled in the art that as a result of the degeneracy of the genetic code, a multitude or polynucleotide sequences encoding LME, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring LME, and all such variations are to be considered as being specifically disclosed.

Although nucleotide sequences which encode LME and its variants are generally capable of hybridizing to the nucleotide sequence of the naturally occurring LME under appropriately selected conditions of stringency, it may be advantageous to produce nucleotide sequences encoding LME or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Otter reasons for substantially altering the nucleotide sequence encoding LME and its derivatives without altering the encoded amino acid sequences include the production of RNA transcripts having more desirable properties, such as a greater half-life, than transcripts produced from the naturally occurring sequence.

The invention also encompasses production of DNA sequences which encode LME and LME derivatives, or fragments thereof, entirely by synthetic chemistry. After production, the synthetic sequence may be inserted into any of the many available expression vectors and all systems using reagents well known in the art. Moreover, synthetic chemistry may be used to introduce mutations into a sequence encoding LME or any fragment thereof.

Also encompassed by the invention are polynucleotide sequences that are capable of hybridizing to the claimed polynucleotide sequences, and, in particular, to those shown in SEQ ID NO:7-12 and fragments thereof under various conditions of stringency. (See, e.g., Wahl, G. M. and S. L. Berger (1987) Methods Enzymol. 152:399-407; Kimmel, A. R. (1987) Methods Enzymol. 152:507-511.) Hybridization conditions, including annealing and wash conditions, are described in "Definitions."

Methods for DNA sequencing are well known in the art and may be used to practice any of the embodiments of the invention. The methods may employ such enzymes as the Klenow fragment of DNA polymerase I, SEQUENASE (US Biochemical, Cleveland Ohio), Taq polymerase (Applied Biosystems), thermostable T7 polymerase (Amersham Pharmacia Biotech, Piscataway N.J.), or combinations of polymerases and proofreading exonucleases such as those found in the ELONGASE amplification system (Life Technologies, Gaithersburg Md.). Preferably, sequence preparation is automated with machines such as the MICROLAB 2200 liquid transfer system (Hamilton, Reno Nev.), PTC200 thermal cycler (MJ Research, Watertown Mass.) and ABI CATALYST 800 thermal cycler (Applied Biosystems). Sequencing is then carried out using either the ABI 373 or 377 DNA sequencing system (Applied Biosystems), the MEGABACE 1000 DNA sequencing system (Molecular Dynamics, Sunnyvale Calif.), or other systems known in the art. The resulting sequences are analyzed using a variety of algorithms which are well known in the art. (See, e.g., Ausubel, F. M. (1997) Short Protocols in Molecular Biology, John Wiley & Sons, New York N.Y., unit 7.7; Meyers, R. A. (1995) Molecular Biology and Biotechnology, Wiley VCH, New York N.Y., pp. 856-853.)

The nucleic acid sequences encoding LME may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318-322.) Another method, inverse PCR, uses primers that extended in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method capture PCR, involves PCR amplification of DNA fragments adjacent to known sequences in human and yeast artificial chromosome DNA. (See, e.g., Lagerstrom, M. et al. (1991) PCR Methods Applic. 1:111-119.) In this method, multiple restriction enzyme digestions and ligations may be used to insert an engineered double-stranded sequence into a region of unknown sequence before performing PCR. Other methods which may be used to retrieve unknown sequences are known in the art (See, e.g., Parker, J. D. et al. (1991) Nucleic Acids Res. 19:3055-3060). Additionally, one may use PCR, nested primers, and PROMOTERFINDER libraries (Clontech, Palo Alto Calif.) to walk genomic DNA. This procedure avoids the need to screen libraries and is useful in finding intron/exon junctions. For all PCR-based methods, primers may be designed using commercially available software, such as OLIGO 4.06 primer analysis software (National Biosciences, Plymouth Minn.) or another appropriate program, to be about 22 to 30 nucleotides in length, to have a GC content of about 50% or more, and to anneal to the template at temperatures of about 68° C. to 72° C.

When screening for full length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide specific, laser-stimulated fluorescent dyes, and a charge coupled device camera for detection of the emitted wavelengths. Output/light intensity may be converted to electrical signal using appropriate software (e.g., GENOTYPER and SEQUENCE NAVIGATOR, Applied Biosystems), and the entire process from loading of samples to computer analysis and electronic data display may be computer controlled.

Capillary electophoresis is especially preferable for sequencing small DNA fragments which may be present in limited amounts in a particular sample.

In another embodiment of the invention, polynucleotide sequences or fragments thereof which encode LME may be cloned in recombinant DNA molecules that direct expression of LME, or fragments or functional equivalents thereof, in appropriate host cells. Due to tee inherent degeneracy of the genetic code, other DNA sequences which encode substantially the same or a functionally equivalent amino acid sequence may be produced and used to express LME.

The nucleotide sequences of the present invention can be engineered using methods generally known in the art in order to alter LME-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide mediated site-directed mutagenesis may be used to introduce mutations that create new restriction sites, alter glycosylation patterns, change codon preference, produce splice variants, and so forth.

The nucleotides of the present invention may be subjected to DNA shuffling techniques such as MOLECULAR-BREEDING (Maxygen Inc., Santa Clara Calif.; described in U.S. Pat. No. 5,837,458; Chang, C.-C. et al. (1999) Nat. Biotechnol. 17:793-797; Christians, F. C. et al. (1999) Nat. Biotechnol. 17:259-264; and Crameri, A. et al. (1996) Nat. Biotechnol. 14:315-319) to alter or improve the biological properties of LME, such as its biological or enzymatic activity or its ability to bind to other molecules or compounds. DNA shuffling is a process by which a library of gene variants is produced using PCR-mediated recombination of gene fragments. The library is then subjected to selection or screening procedures that identify those gene variants with the desired properties. These preferred variants may then be pooled and further subjected to recursive rounds of DNA shuffling and selection/screening. Thus, genetic diversity is created through "artificial" breeding and rapid molecular evolution. For example, fragments of a single gene containing random point mutations may be recombined, screened, and then reshuffled until the desired properties are optimized. Alternatively, fragments of a given gene may be recombined with fragments of homologous genes in the same gene family, either from the same or different species, thereby maximizing the genetic diversity of multiple naturally occurring genes in a directed and controllable manner.

In another embodiment, sequences encoding LME may be synthesized, in whole or in part, using chemical methods well known in the art. (See, e.g., Caruthers, M. H. et al. (1980) Nucleic Acids Symp. Ser. 7:215-223; and Horn, T. et al. (1980) Nucleic Acids Symp. Ser. 7:225-232.) Alternatively, LME itself or a fragment thereof may be synthesized using chemical methods. For example, peptide synthesis can be performed using various solution-phase or solid-phase techniques. (See, e.g., Creighton, T. (1984) *Proteins, Structures and Molecular Properties*, WH Freeman, New York N.Y., pp. 55-60; and Roberge, J. Y. et al. (1995) Science 269:202-204.) Automated synthesis may be achieved using the ABI 431A peptide synthesizer (Applied Biosystems). Additionally, the amino acid sequence of LME, or any part thereof may be altered during direct synthesis and/or combined with sequences from other proteins, or any part thereof, to produce a variant polypeptide or a polypeptide having a sequence of a naturally occurring polypeptide.

The peptide may be substantially purified by preparative high performance liquid chromatography. (See, e.g., Chiez, R. M. and F. Z. Regnier (1990) Methods Enzymol. 182:392-421.) The composition of the synthetic peptides may be confirmed by amino acid analysis or by sequencing. (See, e.g., Creighton, supra, pp. 28-53.)

In order to express a biologically active LME, the nucleotide sequences encoding LME or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding LME. Such elements may vary in their strength and specificity. Specific initiation signals may also be used to achieve more efficient translation of sequences encoding LME. Such signals include the ATG initiation codon and adjacent sequences, e.g. the Kozak sequence. In cases where sequences encoding LME and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125-162.)

Methods which are well known to those skilled in the art may be used to construct expression vectors containing sequences encoding LME and appropriate transcriptional and translational control elements. These methods include in vitro recombinant DNA techniques, synthetic techniques, and in vivo genetic recombination (See e.g., Sambrook, J. et al. (1989) *Molecular Cloning, A Laboratory Manual*, Cold Spring Harbor Press, Plainview N.Y., ch. 4, 8, and 16-17; Ausubel, F. M. et al. (1995) *Current Protocols in Molecular Biology*, John Wiley & Sons, New York N.Y., ch. 9, 13, and 16.)

A variety of expression vector/host systems may be utilized to contain and express sequences encoding LME. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus, CaMV, or tobacco mosaic virus, TMV) or with bacterial expression vectors (e.g., Ti or pBR322 plasmids); or animal cell systems. (See, e.g., Sambrook, supra; Ausubel, supra; Van Heeke, G. and S. M. Schuster (1989) J. Biol. Chem. 264:5503-5509; Engelhard, E. K. et al. (1994) Proc. Natl. Acad. Sci. USA 91:3224-3227; Sandig, V. et al. (1996) Hum. Gene Ther. 7:1937-1945; Takamatsu, N. (1987) EMBO J. 6:307-311; *The McGraw Hill Yearbook of Science and Technology* (1992) McGraw Hill, New York N.Y., pp. 191-196; Logan, J, and T. Shenk (1984) Proc. Natl. Acad. Sci. USA 81:3655-3659; and Harrington, J. J. et al. (1997) Nat. Genet. 15:345-355.) Expression vectors derived from retroviruses, adenoviruses, or herpes or vaccinia viruses, or from various bacterial plasmids, may be used for delivery of nucleotide sequences to the targeted organ, tissue, or cell population. (See, e.g., Di Nicola, M. et al. (1998) Cancer Gen. Ther. 5(6):350-356; Yu, M. et al. (1993) Proc. Natl. Acad. Sci. USA 90(13):634-6344; Buller, R. M. et al. (1985) Nature 317(6040):813-815; McGregor, D. P. et al. (1994) Mol. Immunol. 31(3):219-226; and Verma, I. M. and N. Somia (1997) Nature 389:239-242.) The invention is not limited by file host cell employed.

In bacterial systems, a number of cloning and expression vectors may be selected depending upon the use intended for polynucleotide sequences encoding LME. For example, routine cloning, subcloning, and propagation of polynucleotide sequences encoding LME can be achieved using a multifunctional *E. coli* vector such as PBLUESCRIPT (Stratagene, La Jolla Calif.) or PSPORT1 plasmid (Life Technologies). Ligation of sequences encoding LME into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503-5509.) When large quantities of LME are needed e.g. for the production of antibodies, vectors which direct high level expression of LME may be used. For example, vectors containing the strong, inducible SP6 or T7 bacteriophage promoter may be used.

Yeast expression systems may be used for production of LME. A number of vectors containing constitutive or inducible promoters, such as alpha factor, alcohol oxidase, and PGH promoters, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g., Ausubel, 1995, supra; Bitter, G. A. et al. (1987) Methods Enzymol. 153:516-544; and Scorer, C. A. et al. (1994) Bio/Technology 12:181-184.)

Plant systems may also be used for expression of LME. Transcription of sequences encoding LME may be driven by viral promoters, e.g., the 35S and 19S promoters of CaMV used alone or in combination with the omega leader sequence from TMV (Takamatsu, N. (1987) EMBO J. 6:307-311). Alternatively, plant promoters such as the small subunit of RUBISCO or heat shock promoters may be used. (See, e.g. Coruzzi, G. et al. (1984) EMBO J. 3:1671-1680; Broglie, R. et al. (1984) Science 224:838-843; and Winter, J. et al. (1991) Results Probl. Cell Differ. 17:85-105.) These constructs can be introduced into plant cells by direct DNA transformation or pathogen-mediated transfection (See, e.g., *The McGraw Hill Yearbook of Science and Technology* (1992) McGraw Hill, New York N.Y., pp. 191-196.)

In mammalian cells, a number of viral-based expression systems may be utilized. In cases where an adenovirus is used as an expression vector, sequences encoding LME may be ligated into an adenovirus transcription/translation complex consisting of the late promoter and tripartite leader sequence. Insertion in a non-essential E1 or E3 region of the viral genome may be used to obtain infective us which expresses LME in host cells. (See, e.g., Logan, J. and T. Shenk (1984) Proc. Natl. Acad. Sci. USA 81:3655-3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes. (See, e.g., Harrington, J. J. et al. (1997) Nat. Genet. 15:345-355.)

For long term production of recombinant proteins in mammalian systems, stable expression of LME in cell lines is preferred. For example, sequences encoding LME can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purse of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymine kinase and adenine phosphoribosyltransferase genes, for use in $tk^-$ and $apr^-$ cells, respectively. (See, e.g., Wigler, M. et al. (1977) Cell 11:223-232; Lowy, I. et al. (1980) Cell 22:817-823.) Also, antimetabolite, antibiotic, or herbicide resistance can be used as the basis for selection. For example, dhfr confers resistance to methotrexate; neo confers resistance to the aminoglycosides neomycin and G418; and als and pat confer resistance to chlorsulfuron and phosphinotricin acetyltransferase, respectively. (See, e.g., Wigler, M. et al. (1980) Proc. Natl. Acad. Sci. USA 77:3567-3570; Colbere-Garapin, F. et al. (1981) J. Mol. Biol. 150:1-14.) Addition selectable genes have been described, e.g., trpB and hisD, which alter cellular requirements for metabolites. (See, e.g., Hartman, S. C. and R. C. Mulligan (1988) Proc. Natl. Acad. Sci. USA 85:8047-8051.) Visible markers, e.g., anthocyanins, green fluorescent proteins (GFP; Clontech), β glucuronidase and its substrate β-glucuronide, or luciferase and its substrate luciferin may be used. These markers can be used not only to identify transformants, but also to quantify the amount of transient or stable protein expression attributable to a specific vector system. (See, e.g., Rhodes, C. A. (1995) Methods Mol. Biol. 55:121-131.)

Although the presence/absence of marker gene expression suggests that the gene of interest is also present, the presence and expression of the gene may need to be confirmed. For example, if the sequence encoding LME is inserted within a marker gene sequence, transformed cells containing sequences encoding LME can be identified by the absence of marker gene function. Alternatively, a marker gene can be placed in tandem with a sequence encoding LME under the control of a single promoter. Expression of the marker gene in response to induction or selection usually indicates expression of the tandem gene as well.

In general, host cells that contain the nucleic acid sequence encoding LME and that express LME may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of LME using either specific polyclonal or monoclonal antibodies are known in the art. Examples of such techniques include enzyme-biked immunosorbent assays (ELISAs), radioimmunoassays (RIAs), and fluorescence activated cell sort (FACS). A two-site, monoclonal-based immunoassay utilizing monoclonal antibodies reactive to two non-interfering epitopes on LME is preferred, but a competitive binding assay may be employed. These and other assays are well known in the art. (See, e.g., Hampton, R. et al. (1990) *Serological Methods, a Laboratory Manual*, APS Press, St. Paul Minn., Sect. IV; Coligan, J. E. et al. (1997) *Current Protocols in Immunology*, Greene Pub. Associates and Wiley-Interscience, New York N.Y.; and Pound, J. D. (1998) *Immunochemical Protocols*, Humana Press, Totowa N.J.)

A wide variety of labels and conjugation techniques are known by those skilled in the art and may be used in various nucleic acid and amino acid assays. Means for producing labeled hybridization or PCR probes for detecting sequences related to polynucleotides encoding LME include oligolabeling, nick translation, end-labeling, or PCR amplification using a labeled nucleotide. Alternatively, the sequences encoding LME, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Amersham Pharmacia Biotech, Promega (Madison Wis.), and US Biochemical. Suitable reporter molecules or labels which may be used for ease of detecting include radionuclides, enzymes, fluorescent, chemiluminescent, or chromogenic agents, as well as substrates, cofactors, inhibitors, magnetic particles, and the like.

Host cells transformed with nucleotide sequences encoding LME may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode LME may be designed to contain signal sequences which direct secretion of LME through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation lipidation, and acylation. Post-translational processing which cleaves a "prepro" or "pro" form of the protein may also be used to specify protein targeting, folding, and/or activity. Different host cells which have specific cellular machinery and characteristic mechanisms for post-translational activities (e.g., CHO, HeLa, MDCK, HEK293, and WI38) are available from the American Type Culture Collection (ATCC, Manassas Va.) and may be chosen to ensure the correct modification and processing of the foreign protein.

In another embodiment of the invention, natural, modified, or recombinant nucleic acid sequences encoding LME may be ligated to a heterologous sequence resulting in translation of a fusion protein in any of the aforementioned host systems. For example, a chimeric LME protein containing a heterologous moiety that can be recognized by a commercially available antibody may facilitate the screening of peptide libraries for inhibitors of LME activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the LME encoding sequence and the heterologous protein sequence, so that LME may be cleaved away from the heterologous moiety following purification. Methods for fusion protein expression and purification are discussed in Ausubel (1995, supra, ch. 10). A variety of commercially available kits may also be used to facilitate expression and purification of fusion proteins.

In a further embodiment of the invention, synthesis of radiolabeled LME may be achieved in vitro using the TNT rabbit reticulocyte lysate or wheat germ extract system (Promega). These systems couple transcription and translation of protein-coding sequences operably associated with the T7, T3, or SP6 promoters. Translation takes place in the presence of a radiolabeled amino acid precursor, for example, $^{35}$S-methionine.

LME of the present invention or fragments thereof may be used to screen for compounds that specifically bind to LME. At least one and up to a plurality of test compounds may be screened for specific binding to LME. Examples of test compounds include antibodies, oligonucleotides, proteins (e.g., receptors), or small molecules.

In one embodiment, the compound thus identified is closely related to the natural ligand of LME, e.g., a g, and or fragment thereof a natural substrate, a structural or functional mimetic, or a natural binding partner, (See, e.g., Coligan, J. E. et al. (1991) *Current Protocols in Immunology* 1(2): Chapter 5.) Similarly, the compound can be closely related to the natural receptor to which LME binds, or to at least a fragment of the receptor, e.g., the ligand binding site. In either case, the compound can be rationally designed using known techniques. In one embodiment, screening for these compounds involves producing appropriate cells which express LME, either as a secreted protein or on the cell membrane. Preferred cells include cells from mammals, yeast, *Drosophila*, or *E. coli*. Cells expressing LME or cell membrane fractions which contain LME are then contacted with a test compound and binding, stimulation, or inhibition of activity of either LME or the compound is analyzed.

An assay may simply test binding of a test compound to the polypeptide, wherein binding is detected by a fluorophore, radioisotope, enzyme conjugate, or other detectable label. For example, the assay may comprise the steps of combining at least one test compound with LME, either in solution or affixed to a solid support, and detecting the binding of LME to the compound. Alternatively, the assay may detect or measure binding of a test compound in the presence of a labeled competitor. Additionally, the assay may be carried out using cell-free preparations, chemical libraries, or natural product mixtures, and the test compound(s) may be free in solution or affixed to a solid support.

LME of the present invention or fragments thereof may be used to screen for compounds that modulate the activity of LME. Such compounds may include agonists, antagonists, or partial or inverse agonists. In one embodiment, an assay is performed under conditions permissive for LME activity, wherein LME is combined with at least one test compound, and the activity of LME in the presence of a test compound is compared with the activity of LME in the absence of the test compound. A change in the activity of LME in the presence of the test compound is indicative of a compound that modulates the activity of LME. Alternatively, a test compound is combined with an in vitro or cell-free system comprising LME under conditions suitable for LME activity, and the assay is performed. In either of these assays, a test compound which modulates the activity of LME may do so indirectly and need not come in direct contact with the test compound. At least one and up to a plurality of test compounds may be screened.

In another embodiment, polynucleotides encoding LME or their mammalian homologs may be "knocked out" in an animal model system using homologous recombination in embryonic stem (ES) cells. Such techniques are well known in the art and are useful for the generation of animal models of human disease. (See, e.g., U.S. Pat. No. 5,175,383 and U.S. Pat. No. 5,767,337.) For example, mouse ES cells, such as the mouse 129/SvJ cell line, are derived from the early mouse embryo and grown in culture. The ES cells are transformed with a vector containing the gene of interest disrupted by a marker gene, e.g., the neomycinphosphotransferase gene (neo; Capecchi, M. R. (1989) Science 244:1288-1292). The vector integrates into the corresponding region of the host genome by homologous recombination. Alternatively, homologous recombination takes place using the Cre-loxP system to knockout a gene of interest in a tissue- or developmental stage-specific manner (Marth, J. D. (1996) Clin. Invest. 97:1999-2002; Wagner, K. U. et al. (1997) Nucleic Acids Res. 25:4323-4330). Transformed ES cells are identified and microinjected into mouse cell blastocysts such as those from the C57BL/6 mouse strain. The blastocysts are surgically transferred to pseudopregnant dams, and the resulting chimeric progeny are genotyped and bred to produce heterozygous or homozygous strains. Transgenic animals thus generated may be tested with potential therapeutic or toxic agents.

Polynucleotides encoding LME may also be manipulated in vitro in ES cells derived from human blastocysts. Human ES cells have the potential to differentiate into at least eight separate cell lineages including endoderm, mesoderm, and ectodermal cell types. These cell lineages differentiate into, for example, neural cells, hematopoietic lineages, and cardiomyocytes (Thomson, J. A. et al. (1998) Science 282: 1145-1147).

Polynucleotides encoding LME can also be used to create "knockin" humanized animals (pigs) or transgenic animals (mice or rats) to model human disease. With knockin technology, a region of a polynucleotide encoding LME is injected into animal ES cells, and the injected sequence integrates into the animal cell genome. Transformed cells are injected into blastulae, and the blastulae are implanted as described above. Transgenic progeny or inbred lines are studied and treated with potential pharmaceutical agents to obtain information on treatment of a human disease. Alternatively, a mammal inbred to overexpress LME, e.g., by secreting LME in its milk, may also serve as a convenient source of that protein (Janne, J. et al. (1998) Biotechnol. Annu. Rev. 4:55-74).

Therapeutics

Chemical and structural similarity, e.g., in the context of sequences and motifs, exists between regions of LME and lipid metabolism enzymes. In addition, the expression of LME is closely associated with reproductive tissues, reproductive disorders, cancer, and the representative libraries listed in Table 6. Therefore, LME appears to play a role in cancer, neurological disorders, autoimmune/inflammatory disorders, gastrointestinal disorders, and cardiovascular disorders. In the treatment of disorders associated with increased LME expression or activity, it is desirable to decrease the expression or activity of LME. In the treatment of disorders associated with decreased LME expression or activity, it is desirable to increase the expression or activity of LME.

Therefore, in one, embodiment, LME or a fragment or derivative thereof may be administered to a subject to treat or prevent a disorder associated with decreased expression or activity of LME. Examples of such disorders include, but are not limited to, a cancer, such as adenocarcinoma, leukemia, lymphoma, melanoma, myeloma, sarcoma, teratocarcinoma, and, in particular, cancers of the adrenal gland, bladder, bone, bone marrow, brat, breast cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; a neurological disorder such as epilepsy, ischemic cerebrovascular disease, stroke, cerebral neoplasms, Alzheimer's disease, Pick's disease, Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease, prion diseases including kuru, Creutzfeldt-Jakob disease, and Gerstmann-Straussler-Scheinker syndrome, fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorders of the central nervous system including Down syndrome, cerebral palsy, neuroskeletal disorders, autonomic nervous system disorders, cranial nerve disorders, spinal cord diseases, muscular dystrophy and other neuromuscular disorders, peripheral nervous system disorders, dermatomyositis and polymyositis, inherited, metabolic, endocrine, and toxic myopathies, myasthenia gravis, periodic paralysis, mental disorders including mood, anxiety, and schizophrenic disorders, seasonal affective disorder (SAD), akathesia, amnesia, catatonia, diabetic neuropathy, tardive dyskinesia, dystonias, paranoid psychoses, postherpetic neuralgia, Tourette's disorder, progressive supranuclear palsy, corticobasal degeneration, and familial frontotemporal dementia; an autoimmune inflammatory disorder such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, autoimmune polyendocrinopathy-candidiasis-ectodermal dystrophy (APECED), bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; a gastrointestinal disorder such as dysphagia, peptic esophagitis, esophageal spasm, esophageal structure, esophageal carcinoma, dyspepsia, indigestion, gastritis, gastric carcinoma, anorexia, nausea, emesis, gastroparesis, antral or pyloric edema, abdominal angina, pyrosis, gastroenteritis, intestinal obstruction, infections of the intestinal tract, peptic ulcer, cholelithiasis, cholecystitis, cholestasis, pancreatitis, pancreatic carcinoma, biliary tract disease, hepatitis, hyperbilirubinemia, cirrhosis, passive congestion of the liver, hepatoma, infectious colitis, ulcerative colitis, ulcerative proctitis, Crohn's disease, Whipple's disease, Mallory-Weiss syndrome, colonic carcinoma, colonic obstruction, irritable bowel syndrome, short bowel syndrome, diarrhea, constipation, gastrointestinal hemorrhage, acquired immunodeficiency syndrome (AIDS) enteropathy, jaundice, hepatic encephalopathy, hepatorenal syndrome, hepatic steatosis, hemochromatosis, Wilson's disease, alpha$_1$-antitrypsin deficiency, Reye's syndrome, primary sclerosing cholangitis, liver infarction, portal vein obstruction and thrombosis, centrilobular necrosis, peliosis hepatis, hepatic vein thrombosis, veno-occlusive disease, preeclampsia, eclampsia, acute fatty liver of pregnancy, intrahepatic cholestasis of pregnancy, and hepatic tumors including nodular hyperplasias, adenomas, and carcinomas; and a cardiovascular disorder such as arteriovenous fistula, atherosclerosis, hypertension, vasculitis, Raynaud's disease, aneurysms, arterial dissections, varicose veins, thrombophlebitis and phlebothrombosis, vascular tumors, and complications of thrombolysis, balloon angioplasty, vascular replacement, and coronary artery bypass graft surgery, congestive heart failure, ischemic heart disease, angina pectoris, myocardial infarction, hypertensive heart disease, degenerative valvular heart disease, calcific aortic valve stenosis, congenitally bicuspid aortic valve, mitral annular calcification, mitral valve prolapse, rheumatic fever and rheumatic heart disease, infective endocarditis, nonbacterial thrombotic endocarditis, endocarditis of systemic lupus erythematosus, carcinoid heart disease, cardiomyopathy, myocarditis, pericarditis, neoplastic heart disease, congenital heart disease, and complications of cardiac transplantation, congenital lung anomalies, atelectasis, pulmonary congestion and edema, pulmonary embolism, pulmonary hemorrhage, pulmonary infarction, pulmonary hypertension, vascular sclerosis, obstructive pulmonary disease, restrictive pulmonary disease, chronic obstructive pulmonary disease, emphysema, chronic bronchitis, bronchial asthma, bronchiectasis, bacterial pneumonia, viral and mycoplasmal pneumonia, lung abscess, pulmonary tuberculosis, diffuse interstitial diseases, pneumoconioses, sarcoidosis, idiopathic pulmonary fibrosis, desquamative interstitial pneumonitis, hypersensitivity pneumonitis, pulmonary eosinophilia bronchiolitis obliterans-organizing pneumonia, diffuse pulmonary hemorrhage syndromes, Goodpasture's syndromes, idiopathic pulmonary hemosiderosis, pulmonary involvement in collagen-vascular disorders, pulmonary alveolar proteinosis, lung tumors, inflammatory and noninflammatory pleural effusions, pneumothorax, pleural tumors, drug-induced lung disease, radiation-induced lung disease, and complications of lung transplantation.

In another embodiment, a vector capable of expressing LME or a fragment or derivative thereof may be administered to a subject to treat or prevent a disorder associated with decreased expression or activity of LME including, but not limited to, those described above.

In a further embodiment, a composition comprising a substantially purified LME in conjunction with a suitable pharmaceutical carrier may be administered to a subject to treat or prevent a disorder associated with decreased expression or activity of LME including, but not limited to, those provided above.

In still another embodiment, an agonist which modulates the activity of LME may be administered to a subject to treat or prevent a disorder associated with decreased expression or activity of LME including, but not limited to, those listed above.

In a further embodiment, an antagonist of LME may be administered to a subject to treat or prevent a disorder associated with increased expression or activity of LME. Examples of such disorders include, but are not limited to, those cancers, neurological disorders, autoimmune/inflammatory disorders, gastrointestinal disorders, and cardiovascular disorders described above. In one aspect, an antibody which specifically binds LME may be used directly as an antagonist or indirectly as a targeting or delivery mechanism for bringing a pharmaceutical agent to cells or tissues which express LME.

In an additional embodiment, a vector expressing the complement of the polynucleotide encoding LME may be administered to a subject to treat or prevent a disorder associated with increased expression or activity of LME including, but not limited to, those described above.

In other embodiments, any of the proteins, antagonists, antibodies, agonists, complementary sequences, or vectors of ft invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of LME may be produced using methods which are generally known in the art. In particular, purified LME may be used to produce antibodies or to screen libraries of pharmaceutical agents to identify those which specifically bind LME. Antibodies to LME may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are generally preferred for therapeutic use.

For the production of antibodies, various hosts including goats, rabbits, rats, mice, humans, and others may be immunized by injection with LME or with any fragment or oligopeptide hereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (*bacilli* Calmette-Guerin) and *Corynebacterium parvum* are especially preferable.

It is preferred that the oligopeptides, peptides, or fragments used to induce antibodies to LME have an amino acid sequence consisting of at least about 5 amino acids, and generally will consist of at least about 10 amino acids. It is also preferable that these oligopeptides, peptides, or fragments are identical to a portion of the amino acid sequence of the natural protein. Short stretches of LME amino acids may be fused with those of another protein, such as KLH, and antibodies to the chimeric molecule may be produced.

Monoclonal antibodies to LME may be prepared using any technique which provides for the production of antibody molecules by continuous cell lines in culture. These include, but are not limited to, the hybridoma technique, the human B-cell hybridoma technique, and the EBV-hybridoma technique (Sees e.g., Kohler, G. et al. (1975) Nature 256:495-497; Kozbor, D. et al. (1985) J. Immunol. Methods 81:31-42; Cote, R. J. et al. (1983) Proc. Natl. Acad. Sci. USA 80:2026-2030; and Cole, S. P. et al. (1984) Mol. Cell Biol. 62:109-120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. USA 81:6851-6855; Neuberger, M. S. et al. (1984) Nature 312:604-608; and Takeda, S. et al. (1985) Nature 314:452-454.) Alternatively, techniques described for the production of single chain antibodies may be adapted, using methods known in the art, to produce LME-specific single chain antibodies. Antibodies with related specificity, but of distinct idiotypic composition, may be generated by chain shuffling from random combinatorial immunoglobulin libraries. (See, e.g., Burton, D. R. (1991) Proc. Natl. Acad. Sci. USA 88:10134-10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. USA 86:3833-3837; Winter, G. et al. (1991) Nature 349:293-299.)

Antibody fragments which contain specific binding sites for LME may also be generated. For example, such fragments include, but are not limited to, $F(ab')_2$ fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275-1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between LME and its specific antibody. A two-site, monoclonal-based immunoassay utilizing monoclonal antibodies reactive to two non-interfering LME epitopes is generally used, but a competitive binding assay may also be employed (Pound, supra).

Various methods such as Scatchard analysis in conjunction with radioimmunoassay techniques may be used to assess the affinity of antibodies for LME. Affinity is expressed as an association constant, $K_a$, which is defined as the molar concentration of LME-antibody complex divided by the molar concentrations of free antigen and free antibody under equilibrium conditions. The $K_a$ determined for a preparation of polyclonal antibodies, which are heterogeneous in their affinities for multiple LME epitopes, represents the average affinity, or avidity, of the antibodies for LME. The $K_a$ determined for a preparation of monoclonal antibodies, which are monospecific for a particular LME epitope, represents a true measure of affinity. High-affinity antibody preparations with $K_a$ ranging from about $10^9$ to $10^{12}$ L/mole are preferred for use in immunoassays in which the LME-antibody complex must withstand rigorous manipulations. Low-affinity antibody preparations with $K_a$ ranging from about $10^6$ to $10^7$ L/mole are preferred for use in immunopurification and similar procedures which ultimately require dissociation of LME, preferably in active form, from the antibody (Catty, D. (1988) *Antibodies, Volume I: A Practical Approach*, IRL Press, Washington D.C.; Liddell, J. E. and A. Cryer (1991) *A Practical Guide to Monoclonal Antibodies*, John Wiley & Sons, New York N.Y.).

The titer and avidity of polyclonal antibody preparations may be further evaluated to determine the quality and suitability of such preparations for certain downstream applications. For example, a polyclonal antibody preparation containing at least 1-2 mg specific antibody/ml, preferably 5-10 mg specific antibody/n, is generally employed in procedures requiring precipitation of LME-antibody complexes. Procedures for evaluating antibody specificity, titer, and avidity, and guidelines for antibody quality and usage in various applications, are generally available. (See, e.g., Catty, supra, and Coligan et al. supra.)

In another embodiment of the invention, the polynucleotides encoding LME, or any fragment or complement thereof, may be used for therapeutic purposes. In one aspect, modifications of gene expression can be achieved by designing complementary sequences or antisense molecules (DNA, RNA, PNA, or modified oligonucleotides) to the coding or regulatory regions of the gene encoding LME. Such technology is well known in the art, and antisense oligonucleotides or larger fragments can be designed from various locations along the coding or control regions of sequences encoding LME. (See, e.g., Agrawal, S., ed. (1996) *Antisense Therapeutics*, Humana Press Inc., Totawa N.J.)

In therapeutic use, any gene delivery system suitable for introduction of the antisense sequences into appropriate target cells can be used. Antisense sequences can be delivered intracellularly in the form of an expression plasmid which, upon transcription, produces a sequence complementary to at least a portion of the cellular sequence encoding the target protein. (See, e.g., Slater, J. E. et al. (1998) J. Allergy Cli. Immunol. 102(3):469-475; and Scanlon, K. J. et al. (1995) 9(13):1288-1296.) Antisense sequences can also be introduced intracellularly through the use of viral vectors, such as retrovirus and adeno-associated virus vectors. (See, e.g., Miller, A. D. (1990) Blood 76:271; Ausubel, supra; Uckert, W. and W. Walther (1994) Pharmacol. Ther. 63(3): 323-347.) Other gene delivery mechanisms include liposome-derived systems, artificial viral envelopes, and other systems known in the art. (See, e.g., Rossi, J. J. (1995) Br. Med. Bull. 51(1):217-225; Boado, R. J. et al. (1998) J. Pharm. Sci. 87(11):1308-1315; and Morris, M. C. et al. (1997) Nucleic Acids Res. 25(14):2730-2736.)

In another embodiment of the invention, polynucleotides encoding LME may be used for somatic or germline gene therapy. Gene therapy may be performed to (i) correct a genetic deficiency (e.g., in the cases of severe combined immunodeficiency (SCID)-X1 disease characterized by X-linked inheritance (Cavazzana-Calvo, M. et al. (2000) Science 288:669-672), severe combined immunodeficiency syndrome associated with an inherited adenosine deaminase (ADA) deficiency (Blaese, R. M. et al. (1995) Science 270:475-480; Bordignon, C. et al. (1995) Science 270:470-475), cystic fibrosis (Zabner, J. et al. (1993) Cell 75:207-216; Crystal, R. G. et al. (1995) Hum. Gene Therapy 6:643-666; Crystal, R. G. et al. (1995) Hum. Gene Therapy 6:667-703), thalassamias, familial hypercholesterolemia, and hemophilia resulting from Factor VIII or Factor IX deficiencies (Crystal, R. G. (1995) Science 270:404-410; Verma, I. M. and N. Soma (1997) Nature 389:239-242)), (ii) express a conditionally lethal gene product (e.g., in the case of cancers which result from unregulated cell proliferation), or (iii) express a protein which affords protection against intracellular parasites (e.g., against human retroviruses, such as human immunodeficiency virus (HIV) (Baltimore, D. (1988) Nature 335:395-396; Poeschla, E. et al. (1996) Proc. Natl. Acad. Sci. USA. 93:11395-11399), hepatitis B or C virus (HBV, HCV); fungal parasites, such as *Candida albicans* and *Paracoccidioides brasiliensis*; and protozoan parasites such as *Plasmodium falciparum* and *Trypanosoma cruzi*). In the case where a genetic deficiency in LME expression or regulation causes disease the expression of LME from an appropriate population of transduced cells may alleviate the clinical manifestations caused by the genetic deficiency.

In a further embodiment of the invention, diseases or disorders caused by deficiencies in LME are treated by constructing mammalian expression vectors encoding LME and introducing these vectors by mechanical means into LME-deficient cells. Mechanical transfer technologies for use with cells in vivo or ex vitro include (i) direct DNA microinjection into individual cells, (ii) ballistic gold particle delivery, (iii) liposome-mediated transfection, (iv) receptor-mediated gene transfer, and (v) the use of DNA transposons (Morgan, R. A. and W. F. Anderson (1993) Annu. Rev. Biochem. 62:191-217; Ivics, Z. (1997) Cell 91:501-510; Boulay, J-L. and H. Récipon (1998) Curr. Opin. Biotechnol. 9:445-450).

Expression vectors that may be effective for the expression of LME include, but are not limited to, the PCDNA3.1, EPITAG, PRCCMV2, PREP, PVAX vectors (Invitrogen, Carlsbad Calif.), PCMV-SCRIPT, PCMV-TAG, PEGSH/PERV (Stratagene, La Jolla Calif.), and PTET-OFF, PTET-ON, PTRE2, PTRE2-LUC, PTK-HYG (Clontech, Palo Alto Calif.). LME may be expressed using (i) a constitutively active promoter, (e.g., from cytomegalovirus (CMV), Rous sarcoma virus (RSV), SV40 virus, thymidine kinase (TK), or β-actin genes), (ii) an inducible promoter (e.g., the tetracycline-regulated promoter (Gossen, M. and H. Bujard (1992) Proc. Natl. Acad. Sci. USA 89:5547-5551; Gossen, M. et al. (1995) Science 268:1766-1769; Rossi, F. M. V. and H. M. Blau (1998) Curr. Opin. Biotechnol. 9:451-456), commercially available in the T-REX plasmid (Invitrogen); the ecdysone-inducible promoter (available in the plasmids PVGRXR and PIND; Invitrogen); the FK506/rapamycin inducible promoter; or the RU486/mifepristone inducible promoter (Rossi, F. M. V. and Blau, H. M. supra)), or (iii) a tissue-specific promoter or the native promoter of the endogenous gene encoding LME from a normal individual.

Commercially available liposome transformation kits (e.g., the PERFECT LIPID TRANSFECTION KIT, available from Invitrogen) allow one with ordinary skill in the art to deliver polynucleotides to target cells in culture and require minimal effort to optimize experimental parameters. In the alternative, transformation is performed using the calcium phosphate method (Graham, F. L. and A. J. Eb (1973) Virology 52:456-467), or by electroporation (Neumann, E. et al. (1982) EMBO J. 1:841-845). The introduction of DNA to primary cells requires modification of these standardized mammalian transfection protocols.

In another embodiment of the invention, diseases or disorders caused by genetic defects with respect to LME expression are treated by constructing a retrovirus vector consisting of (i) the polynucleotide encoding LME under the control of an independent promoter or the retrovirus long terminal repeat (LTR) promoter, (ii) appropriate RNA packaging signals, and (iii) a Rev-responsive element (RRE) along with additional retrovirus cis-acting RNA sequences and coding sequences required for efficient vector propagation. Retrovirus vectors (e.g., PFB and PFBNEO) are commercially available (Stratagene) and are based on published data (Riviere, I. et al. (1995) Proc. Natl. Acad. Sci, USA 92:6733-6737), incorporated by reference herein. The vector is propagated in an appropriate vector producing cell line (VPCL) that expresses an envelope gene with a tropism for receptors on the target cells or a promiscuous envelope protein such as VSVg (Armentano, D. et al. (1987) J. Virol. 61:1647-1650; Bender, M. A. et al. (1987) J. Virol. 61:1639-1646; Adam, M. A. and A. D. Miller (1988) J. Virol. 62:3802-3806; Dull, T. et al. (1998) J. Virol. 72:8463-8471; Zufferey, R. et al. (1998) J. Virol. 72:9873-9880). U.S. Pat. No. 5,910,434 to Rigg ("Method for obtaining retrovirus packaging cell lines producing high transducing efficiency retroviral supernatant") discloses a method for obtaining retrovirus packaging cell lines and is hereby incorporated by reference. Propagation of retrovirus vectors, transduction of a population of cells (e.g., CD4$^+$ T-cells), and the return of transduced cells to a patient are procedures well known to persons skilled in the art of gene therapy and have been well documented (Ranga, U. et al. (1997) J. Virol. 71:7020-7029; Bauer, G. et al. (1997) Blood 89:2259-2267; Bonyhadi, M. L. (1997) J. Virol. 71:4707-4716; Ranga, U. et al. (1998) Proc. Natl. Acad. Sci. USA 95:1201-1206; SU, L. (1997) Blood 89:2283-2290).

In the alternative, an adenovirus-based gene therapy delivery system is used to deliver polynucleotides encoding LME to cells which have one or more genetic abnormalities with respect to the expression of LME. The construction and packaging of adenovirus-based vectors are well known to those with ordinary skill in the art. Replication defective adenovirus vectors have proven to be versatile for importing genes encoding immunoregulatory proteins into intact islets in the pancreas (Csete, M. E. et al. (1995) Transplantation 27:263-268). Potentially useful adenoviral vectors are described in U.S. Pat. No. 5,707,618 to Armentano ("Adenovirus vectors for gene therapy"), hereby incorporated by reference. For adenoviral vectors, see also Antinozzi, P. A. et al. (1999) Annu. Rev. Nutr. 19:511-544 and Verma, I. M. and N. Somia (1997) Nature 18:389:239-242, both incorporated by reference herein.

In another alternative, a herpes-based, gene therapy delivery system is used to deliver polynucleotides encoding LME to target cells which have one or more genetic abnormalities with respect to the expression of LME. The use of herpes simplex virus (HSV)-based vectors may be especially valuable for introducing LME to cells of the central nervous system, for which HSV has a tropism. The construction and packaging of herpes-based vectors are well blown to those with ordinary skill in the art. A replication-competent herpes simplex virus (HSV) type 1-based vector has been used to deliver a reporter gene to the eyes of primates (Liu, X. et al.

(1999) Exp. Eye Res. 169:385-395). The construction of a HSV-1 virus vector has also been disclosed in detail in U.S. Pat. No. 5,804,413 to DeLuca ("Herpes simplex virus strains for gene transfer"), which is hereby incorporated by reference. U.S. Pat. No. 5,804,413 teaches the use of recombinant HSV d92 which consists of a genome containing at least one exogenous gene to be transferred to a cell under the control of the appropriate promoter for purposes including human gene therapy. Also taught by this patent are the construction and use of recombinant HSV strains deleted for ICP4, ICP27 and ICP22. For HSV vectors, see also Goins, W. F. et alt (1999) J. Virol. 73:519-532 and Xu, H. et al. (1994) Dev. Biol. 163:152-161, hereby incorporated by reference. The manipulation of cloned herpesvirus sequences, the generation of recombinant virus following the transfection of multiple plasmids containing different segments of the large herpesvirus genomes, the growth and propagation of herpesvirus, and the infection of cells with herpesvirus are techniques well known to those of ordinary skill in the art.

In another alternative, an alphavirus (positive, single-stranded RNA virus) vector is used to deliver polynucleotides encoding LME to target cells. The biology of the prototypic alphavirus, Semliki Forest Virus (SFV), has been studied extensively and gene transfer vectors have been based on the SFV genome (Garoff, H. and K.-J. Li (1998) Curr. Opin. Biotechnol. 9:464-469). During alphavirus RNA replication, a subgenomic RNA is generated that normally encodes the viral capsid proteins. This subgenomic RNA replicates to higher levels than the full length genomic RNA, resulting in the overproduction of capsid proteins relative to the viral proteins with enzymatic activity (e.g., protease and polymerase). Similarly, inserting the coding sequence for LME into the alphavirus genome in place of the capsid-coding region results in the production of a large number of LME-coding RNAs and the synthesis of high levels of LME in vector transduced cells. While alphavirus infection is typically associated with cell lysis within a few days, the ability to establish a persistent infection in hamster normal kidney cells (BHK-21) with a variant of Sindbis virus (SIN) indicates that the lytic replication of alphaviruses can be altered to suit the needs of the gene therapy application (Dryga, S. A. et al. (1997) Virology 228:74-83). The wide host range of alphaviruses will allow the introduction of LME into a variety of cell types. The specific transduction of a subset of cells in a population may require the sorting of cells prior to transduction. The methods of manipulating infectious cDNA clones of alphaviruses, performing alphavirus cDNA and RNA transfections, and performing alphavirus infections, are well known to those with ordinary skill in the art.

Oligonucleotides derived from the transcription initiation site, e.g., between about positions −10 and +10 from the start site, may also be employed to inhibit gene expression. Similarly, inhibition can be achieved using triple helix base-pairing methodology. Triple helix palling is useful because it causes inhibition of the ability of the double helix to open sufficiently for the binding of polymerases, transcription factors, a regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing. Mt. Kisco N.Y., pp. 163-177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding LME.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding LME. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limed to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio, and similarly modified forms of adenine, cytidine, guanine, thymine, and uridine which are not as easily recognized by endogenous endonucleases.

An additional embodiment of the invention encompasses a method for screening for a compound which is effective in altering expression of a polynucleotide encoding LME. Compounds which may be effective in altering expression of a specific polynucleotide may include, but are not limited to, oligonucleotides, antisense oligonucleotides, triple helix-forming oligonucleotides, transcription factors and other polypeptide transcriptional regulators, and non-macromolecular chemical entities which are capable of interacting with specific polynucleotide sequences. Effective compounds may alter polynucleotide expression by acting as either inhibitors or promoters of polynucleotide expression. Thus, in the treatment of disorders associated with increased LME expression or activity, a compound which specifically inhibits expression of the polynucleotide encoding LME may be therapeutically useful and in the treatment of disorders associated with decreased LME expression or activity, a compound which specifically promotes expression of the polynucleotide encoding LME may be therapeutically useful.

At least one, and up to a plurality, of test compounds may be screened for effectiveness in altering expression of a specific polynucleotide. A test compound may be obtained by any method commonly known in the art, including chemical modification of a compound known to be effective in altering polynucleotide expression; selection from an existing, commercially-available or proprietary library of naturally-occurring or non-natural chemical compounds; rational design of a compound based on chemical and/or structural properties of the target polynucleotide; and selection from a library of chemical compounds created combinatorially or randomly. A sample comprising a polynucleotide encoding LME is exposed to at least one test compound thus obtained. The sample may comprise, for example, an intact or permeabilized cell, or an in vitro cell-free or reconstituted biochemical system. Alterations in the expression of a polynucleotide encoding LME are assayed by any method commonly known in the art. Typically, the expression of a specific nucleotide is detected by hybridization with a probe having a nucleotide sequence complementary to the sequence of the polynucleotide encoding LME. The amount of hybridization may be quantified, thus forming the basis for a comparison son of the expression of the polynucleotide both with and without exposure to one or more test compounds. Detection of a change in the expression of a polynucleotide exposed to a test compound indicates that the test compound is effective in altering the expression of the polynucleotide. A screen for a compound effective in altering expression of a specific polynucleotide can be carried out, for example, using a *Schizosaccharomyces pombe* gene expression system (Atkins, D. et al. (1999) U.S. Pat. No. 5,932,435; Arndt, G. M. et al. (2000) Nucleic Acids Res. 28:E15) or a human cell line such as HeLa cell (Clarke, M. L. et al. (2000) Biochem. Biophys. Res. Commun. 268:8-13). A particular embodiment of the present invention involves screening a combinatorial library of oligonucleotides (such as deoxyribonucleotides, ribonucleotides, peptide nucleic acids, and modified-oligonucleotides) for antisense activity against a specific polynucleotide sequence (Bruice, T. W. et al. (1997) U.S. Pat. No. 5,686,242; Bruice, T. W. et al. (2000) U.S. Pat. No. 6,022,691).

Many methods for introducing vectors into cells or tissues are available and equally suitable for use in vivo, in vitro, and ex viva. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g. Goldman, C. K. et al. (1997) Nat. Biotechnol. 15:462-466.)

Any of the therapeutic methods described above may be applied to any subject in need of such therapy, including, for example, mammals such as humans, dogs, cats, cows, horses, rabbits, and monkeys.

An additional embodiment of the invention relates to the administration of a composition which generally comprises an active ingredient formulated with a pharmaceutically acceptable excipient. Excipients may include, for example, sugars, starches, celluloses, gums, and proteins. Various formulations are commonly known and are thoroughly discussed in the latest edition of *Remington's Pharmaceutical Sciences* (Maack Publishing, Easton Pa.). Such compositions may consist of LME, antibodies to LME, and mimetics, agonists, antagonists, or inhibitors of LME.

The compositions utilized in this invention may be administered by any number of routes including, but not limited to, oral, intravenous, intramuscular, intra-arterial, intramedullary, intrathecal, intraventricular, pulmonary, transdermal, subcutaneous, intraperitoneal, intranasal, enteral, topical, sublingual, or rectal means.

Compositions for pulmonary administration may be prepared in liquid a dry powder form. These compositions are generally aerosolized immediately prior to inhalation by the patient. In the case of small molecules (e.g. traditional low molecular weight organic drugs), aerosol delivery of fast-acting formulations is well-known in the art. In the case of macromolecules (e.g. larger peptides and proteins), recent developments in the field of pulmonary delivery via the alveolar region of the lung have enabled the practical delivery of drugs such as insulin to blood circulation (see, e.g., Patton, J. S. et al., U.S. Pat. No. 5,997,848). Pulmonary delivery has the advantage of administration without needle injection, and obviates the need for potentially toxic penetration enhancers.

Compositions suitable for use in the invention include compositions wherein the active ingredients are contained in an effective amount to achieve the intended purpose. The determination of an effective dose is well within the capability of those skilled in the art.

Specialized forms of compositions may be prepared for direct intracelluar delivery of macromolecules comprising LME or fragments thereof. For example, liposome preparations containing a cell-impermeable macromolecule may promote cell fusion and intracellular delivery of the macromolecule. Alternatively, LME or a fragment thereof may be joined to a short cationic N-terminal portion from the HIV Tat-1 protein. Fusion proteins thus generated have been found to transduce into the cells of all tissues, including the brain, in a mouse model system (Schwarze, S. R. et al. (1999) Science 285:1569-1572).

For any compound, the therapeutically effective dose can be estimated initially either in cell culture assays, e.g., of neoplastic cells, or in animal models such as mice, rats, rabbits, dogs, monkeys, or pigs. An animal model may also be used to determine the appropriate concentration range and route of administration. Such information can then be used to determine useful doses and routes for administration in humans.

A therapeutically effective dose refers to that amount of active ingredient, for example LME or fragments thereof, antibodies of LME, and agonists, antagonists or inhibitors of LME, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of toxic to therapeutic effects is the therapeutic index, which can be expressed as the $LD_{50}/ED_{50}$ ratio. Compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage win be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting compositions may be administered every 3 to 4 days, every week, or biweekly depending on the half-life and clearance rate of the particular formulation.

Normal dosage amounts may vary from about 0.1 μg to 100,000 μg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind LME may be used for the diagnosis of disorders characterized by expression of LME, or in assays to monitor patients being treated with LME or agonists, antagonists, or inhibitors of LME. Antibodies useful for diagnostic purposes may be prepared in the same manner as described above for therapeutics. Diagnostic assays for LME include methods which utilize the antibody and a label to detect LME in human body fluids or in exacts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring LME, including ELISAs, RIAs, and FACS, are known in the art and provide a basis for diagnosing altered or abnormal levels of LME expression. Normal or standard values for LME expression are established by combining body fluids or cell extracts taken from normal mammalian subjects, for example, human subjects, with antibodies to LME under conditions suitable for complex formation. The amount of standard complex formation may be quantitated by various methods, such as photometric means. Quantities of LME expressed in subject, control, and disease samples from biopsied tissues are compared with the standard values. Deviation between standard and subject values establishes the parameters for diagnosing disease.

In another embodiment of the invention, the polynucleotides encoding LME may be used for diagnostic purposes. The polynucleotides which may be used include oligonucleotide sequences, complementary RNA and DNA molecules, and PNAs. The polynucleotides may be used to detect and quantify gene expression in biopsied tissues in which expression of LME may be correlated with disease. The diagnostic assay may be used to determine absence, presence, and excess expression of LME, and to monitor regulation of LME levels during therapeutic intervention.

In one aspect, hybridization with PCR probes which are capable of detecting polynucleotide sequences, including genomic sequences, encoding LME or closely related molecules may be used to identify nucleic acid sequences which encode LME. The specificity of the probe, whether it is made from a highly specific region, e.g., the 5' regulatory region, or from a less specific region, e.g., a conserved motif and the stringency of the hybridization or amplification will determine whether the probe identifies only naturally occurring sequences encoding LME, allelic variants, or related sequences.

Probes may also be used for the detection of related sequences, and may have at least 50% sequence identity to any of the LME encoding sequences. The hybridization probes of the subject invention may be DNA or RNA and may be derived from the sequence of SEQ ID NO:7-12 or from genomic sequences including promoters, enhancers, and introns of the LME gene.

Means for producing specific hybridization probes for DNAs encoding LME include the cloning of polynucleotide, sequences encoding LME or LME derivatives into vectors for the production of mRNA probes. Such vectors are known in the art, are commercially available, and may be used in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding LME may be used for the diagnosis of disorders associated with expression of LME. Examples of such disorders include, but are not limited to, cancer, such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; a neurological disorder such as epilepsy, ischemic cerebrovascular disease, stroke, cerebral neoplasms, Alzheimer's disease, Pick's disease, Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease, prion diseases including kuru, Creutzfeldt-Jakob disease, and Gerstmann-Straussler-Scheinker syndrome, fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorders of the central nervous system including Down syndrome, cerebral palsy, neuroskeletal disorders, autonomic nervous system disorders, cranial nerve disorders, spinal cord diseases, muscular dystrophy and other neuromuscular disorders, peripheral nervous system disorders, dermatomyositis and polymyositis, inherited, metabolic, endocrine, and toxic myopathies, myasthenia gravis, periodic paralysis, mental disorders including mood, anxiety, and schizophrenic disorders, seasonal affective disorder (SAD), akathesia, amnesia, catatonia, diabetic neuropathy, tardive dyskinesia, dystonias, paranoid psychoses, postherpetic neuralgia, Tourette's disorder, progressive supranuclear palsy, corticobasal degeneration, and familial frontotemporal dementia; an autoimmune/inflammatory disorder such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, autoimmune polyendocrinopathy-candidiasis-ectodermal dystrophy (APECED), bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma a gastrointestinal disorder such as dysphagia, peptic esophagitis, esophageal spasm, esophageal structure, esophageal carcinoma, dyspepsia, indigestion, gastritis, gastric carcinoma, anorexia, nausea, emesis, gastroparesis, antral or pyloric edema, abdominal angina, pyrosis, gastroenteritis, intestinal obstruction, infections of the intestinal tract, peptic ulcer, cholelithiasis, cholecystitis, cholestasis, pancreatitis, pancreatic carcinoma, biliary tract disease, hepatitis, hyperbilirubinemia, cirrhosis, passive congestion of the liver, hepatoma, infectious colitis, ulcerative colitis, ulcerative proctitis, Crohn's disease, Whipple's disease, Mallory-Weiss syndrome, colonic carcinoma, colonic obstruction, irritable bowel syndrome, short bowel syndrome, diarrhea, constipation, gastrointestinal hemorrhage, acquired immunodeficiency syndrome (AIDS) enteropathy, jaundice, hepatic encephalopathy, hepatorenal syndrome, hepatic steatosis, hemochromatosis, Wilson's disease, alpha$_1$-antitrypsin deficiency, Reye's syndrome, primary sclerosing cholangitis, liver infarction, portal vein obstruction and thrombosis, centrilobular necrosis, peliosis hepatis, hepatic vein thrombosis, veno-occlusive disease, preeclampsia, eclampsia, acute fatty liver of pregnancy, intrahepatic cholestasis of pregnancy, and hepatic tumors including nodular hyperplasias, adenomas, and carcinomas; and a cardiovascular disorder such as arteriovenous fistula, atherosclerosis, hypertension, vasculitis, Raynaud's disease, aneurysms, arterial dissections, varicose veins, thrombophlebitis and phlebothrombosis, vascular tumors, and complications of thrombolysis, balloon angioplasty, vascular replacement, and coronary artery bypass graft surgery, congestive heart failure, ischemic heart disease, angina pectoris, myocardial infarction, hypertensive heart disease, degenerative valvular heart disease, calcific aortic valve stenosis, congenitally bicuspid aortic valve, mitral annular calcification, mitral valve prolapse, rheumatic fever and rheumatic heart disease, infective endocarditis, nonbacterial thrombotic endocarditis, endocarditis of systemic lupus erythematosus, carcinoid heart disease, cardiomyopathy, myocarditis, pericarditis, neoplastic heart disease, congenital heart disease, and complications of cardiac transplantation, congenital lung anomalies, atelectasis, pulmonary congestion and edema, pulmonary embolism, pulmonary hemorrhage, pulmonary infarction, pulmonary hypertension, vascular sclerosis, obstructive pulmonary disease, restrictive pulmonary disease, chronic obstructive pulmonary disease, emphysema, chronic bronchitis, bronchial asthma, bronchiectasis, bacterial pneumonia, viral and mycoplasmal pneumonia, lung abscess, pulmonary tuberculosis, diffuse interstitial diseases, pneumoconioses, sarcoidosis, idiopathic pulmonary fibrosis, desquamative interstitial pneumonitis, hypersensitivity pneumonitis, pulmonary eosinophilia bronchiolitis obliterans-organizing pneumonia, diffuse pulmonary hemorrhage syndromes, Goodpasture's syndromes, idiopathic pulmonary hemosiderosis, pulmonary involvement in collagen-vascular disorders, pulmonary alveolar proteinosis, lung tumors, inflammatory and noninflammatory pleural effusions, pneumothorax, pleural tumors, drug-induced lung disease, radiation-induced lung disease, and complications of lung transplantation. The polynucleotide sequences encoding LME may be used in Southern or northern analysis, dot blot, or other membrane-based technologies; in PCR technologies; in dipstick, pin, and multiformat ELISA-like assays; and in microarrays utilizing fluids or tissues from patients to detect altered LME expression. Such qualitative or quantitative methods are well known in the art.

In a particular aspect, the nucleotide sequences encoding LME may be useful in assays that detect the presence of associated disorders, particularly those mentioned above. The nucleotide sequences encoding LME may be labeled by standard methods and added to a fluid or tissue sample from a patient under conditions suitable for the formation of hybridization complexes. After a suitable incubation period, the sample is washed and the signal is quantified and compared with a standard value. If the amount of signal in the patient sample is significantly altered in comparison to a control sample then the presence of altered levels of nucleotide sequences encoding LAW in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of LME, a normal or standard profile for expression is established. This may be accomplished by combining body fluids or cell extracts taken from normal subjects, either animal or human, with a sequence, or a fragment thereof, encoding LME, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of an abnormal amount of transcript (either under- or overexpressed) in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding LME may involve the use of PCR. These oligomers may be chemically synthesized, generated enzymatically, or produced in vitro. Oligomers will preferably contain a fragment of a polynucleotide encoding LME, or a fragment of a polynucleotide complementary to the polynucleotide encoding LME, and will be employed under optimized conditions for identification of a specific gem or condition. Oligomers may also be employed under less stringent conditions for detection or quantification of closely related DNA or RNA sequences.

In a particular aspect, oligonucleotide primers derived from the polynucleotide sequences encoding LME may be used to detect single nucleotide polymorphisms (SNPs). SNPs are substitutions, insertions and deletions that are a frequent cause of inherited or acquired genetic disease in humans. Methods of SNP detection include, but are not limited to, single-stranded conformation polymorphism (SSCP) and fluorescent SSCP (fSSCP) methods. In SSCP, oligonucleotide primers derived from the polynucleotide sequences encoding LME are used to amplify DNA using the polymerase chain reaction (PCR). The DNA may be derived, for example, from diseased or normal tissue, biopsy samples, bodily fluids, and the like. SNPs in the DNA cause differences in the secondary and tertiary structures of PCR products in single-stranded form and these differences are detectable using gel electrophoresis in non-denaturing gels. In fSCCP, the oligonucleotide primers are fluorescently labeled, which allows detection of the amplimers in high-throughput equipment such as DNA sequencing machines. Additionally, sequence database analysis methods, termed in silico SNP (is SNP), are capable of identifying polymorphisms by comparing the sequence of individual overlapping DNA fragments which assemble into a common consensus sequence. These computer-based methods filter out sequence variations due to laboratory preparation of DNA and sequencing errors using statistical models and automated analyses of DNA sequence chromatograms. In the alternative, SNPs may be detected and characterized by mass spectrometry using, for example, the high throughput MASSARRAY system (Sequenom, Inc., San Diego Calif.).

Methods which may also be used to quantify the expression of LME include radiolabeling or biotinylating nucleotides, coamplification of a control nucleic acid, and interpolating results from standard curves. (See, e.g., Melby, P. C. et al. (1993) J. Immunol. Methods 159:235-244; Duplaa, C. et al. (1993) Anal. Biochem. 212:229-236.) The speed of quantitation of multiple samples may be accelerated by running the assay in a high-throughput format where the oligomer or polynucleotide of interest is presented in various dilutions and a spectrophotometric or colorimetric response gives rapid quantitation.

In further embodiments, oligonucleotides or longer fragments derived from any of the polynucleotide sequences described herein may be used as elements on a microarray. The microarray can be used in transcript imaging techniques which monitor the relative expression levels of large numbers of genes simultaneously as described below. The microarray may also be used to identify genetic variants, mutations, and polymorphisms. This information may be used to determine gene function, to understand the genetic basis of a disorder, to diagnose a disorder, to monitor progression/regression of disease as a function of gene expression, and to develop and monitor the activities of therapeutic agents in the treatment of disease. In particular, this information may be used to develop a pharmacogenomic profile of a patient in order to select the most appropriate and effective treatment regimen for that patient. For example, therapeutic agents which are highly effective and display the fewest side effects may be selected for a patient based on his/her pharmacogenomic profile.

In another embodiment, LME, fragments of LME, or antibodies specific for LME may be used as elements on a microarray. The microarray may be used to monitor or measure protein-protein interactions, drug-target interactions, and gene expression profiles, as described above.

A particular embodiment relates to the use of the polynucleotides of the present invention to generate a transcript image of a tissue or cell type A transcript image represents the global pattern of gene expression by a particular tissue or cell type. Global gene expression patterns are analyzed by quantifying the number of expressed genes and their relative abundance under given conditions and at a given time. (See Seilhamer et al., "Comparative Gene Transcript Analysis," U.S. Pat. No. 5,840,484, expressly incorporated by reference herein.) Thus a transcript image may be generated by hybridizing the polynucleotides of the present invention or their complements to the totality of transcripts or reverse transcripts of a particular tissue or cell type. In one embodiment, the hybridization takes place in high-throughput format, wherein the polynucleotides of the present invention or their complements comprise a subset of a plurality of elements on a microarray. The resultant transcript image would provide a profile of gene activity.

Transcript images may be generated using transcripts isolated from tissues, cell lines, biopsies, or other biological samples. The transcript image may thus reflect gene expression in vivo, as in the case of a tissue or biopsy sample, or in vitro, as in the case of a cell line.

Transcript images which profile the expression of the polynucleotides of the present invention may also be used in conjunction with in vitro model systems and preclinical evaluation of pharmaceuticals, as well as toxicological testing of industrial and naturally-occurring environmental compounds. All compounds induce characteristic gene expression patterns, frequently termed molecular fingerprints or toxicant signatures, which are indicative of mechanisms of action and toxicity (Nuwaysir, E. F. et al. (1999) Mol. Carcinog. 24:153-159; Steiner, S. and N. L. Anderson (2000) Toxicol. Lett. 112-113:467-471, expressly incorporated by reference herein). If a test compound has a signature similar to that of a compound with known toxicity, it is likely to share those toxic properties. These fingerprints or signatures are most useful and refined when they contain expression information from a large number of genes and gene families. Ideally, a genome-wide measurement of expression provides the highest quality signature. Even genes whose expression is not altered by any tested compounds are important as well, as the levels of expression of these genes are used to normalize the rest of the expression data: The normalization procedure is useful for comparison of expression data after treatment with different compounds. While the assignment of gene function to elements of a toxicant signature aids in interpretation of toxicity mechanisms, knowledge of gene function is not necessary for the statistical matching of signatures which leads to prediction of toxicity. (See, for example, Press Release 00-02 from the National Institute of Environmental Health Sciences, released Feb. 29, 2000, available from the internet.) Therefore, it is important and desirable in toxicological screening using toxicant signatures to include all expressed gene sequences.

In one embodiment, the toxicity of a test compound is assessed by treating a biological sample containing nucleic acids with the test compound. Nucleic acids that are expressed in the treated biological sample are hybridized with one or more probes specific to the polynucleotides of the present invention, so that transcript levels corresponding to the polynucleotides of the present invention may be quantified. The transcript levels in the treated biological sample are compared with levels in an untreated biological sample. Differences in the transcript levels between the two samples are indicative of a toxic response caused by the test compound in the treated sample.

Another particular embodiment relates to the use of the polypeptide sequences of the present invention to analyze the proteome of a tissue or cell type. The term proteome refers to the global pattern of protein expression in a particular tissue or cell type. Each protein component of a proteome can be subjected individually to further analysis. Proteome expression patterns, or profiles, are analyzed by quantifying the number of expressed proteins and their relative abundance under given conditions and at a given time. A profile of a cell's proteome may thus be generated by separating and analyzing the polypeptides of a particular tissue or cell type. In one embodiment, the separation is achieved using two-dimensional gel electrophoresis, in which proteins from a sample are separated by isoelectric focusing in the first dimension, and then according to molecular weight by sodium dodecyl sulfate slab gel electophoresis in the second dimension (Steiner and Anderson, supra). The proteins are visualized in the gel as discrete and uniquely positioned spots, typically by staining the gel with an agent such as Coomassie Blue or silver or fluorescent stains. The optical density of each protein spot is generally proportional to the level of the protein in the sample. The optical densities of equivalently positioned protein spots from different samples, for example, from biological samples either treated or untreated with a test compound or therapeutic agent, are compared to identify any changes in protein spot density related to the treatment. The proteins in the spots are partially sequenced using, for example, standard methods employing chemical or enzymatic cleavage followed by mass spectrometry. The identity of the protein in a spot may be determined by comparing its partial sequence, preferably of at least 5 contiguous amino acid residues, to the polypeptide sequences of the present invention. In some cases, further sequence data may be obtained for definitive protein identification.

A proteomic profile may also be generated using antibodies specific for LME to quantify the levels of LME expression. In one embodiment, the antibodies are used as elements on a microarray, and protein expression levels are quantified by exposing the microarray to the sample and detecting the levels of protein bound to each array element (Lueking, A. et al. (1999) Anal. Biochem. 270:103-111; Mendoze, L. G. et al. (1999) Biotechniques 27:778-788). Detection may be performed by a variety of methods known in the art, for example, by reacting the proteins in the sample with a thiol- or amino-reactive fluorescent compound and detecting the amount of fluorescence bound at each array element.

Toxicant signatures at the proteome level are also useful for toxicological screening, and should be analyzed in parallel with toxicant signatures at the transcript level. There is a poor correlation between transcript and protein abundances for some proteins in some tissues (Anderson, N. L. and J. Seilhamer (1997) Electophoresis 18:533-537), so proteome toxicant signatures may be useful in the analysis of compounds which do not significantly affect the transcript image, but which alter the proteomic profile. In addition, the analysis of transcripts in body fluids is difficult, due to rapid degradation of mRNA, so proteomic profiling may be more reliable and informative in such cases.

In another embodiment the toxicity of a test compound is assessed by treating a biological sample containing proteins with the test compound. Proteins that are expressed in the treated biological sample are separated so that the amount of each protein can be quantified. The amount of each protein is compared to the amount of the corresponding protein in an untreated biological sample. A difference in the amount of protein between the two samples is indicative of a toxic response to the test compound in the treated sample. Individual proteins are identified by sequencing the amino acid residues of the individual proteins and comparing these partial sequences to the polypeptides of the present invention.

In another embodiment, the toxicity of a test compound is assessed by treating a biological sample containing proteins with the test compound. Proteins from the biological sample are incubated with antibodies specific to the polypeptides of the present invention. The amount of protein recognized by the antibodies is quantified. The amount of protein in the treated biological sample is compared with the amount in an untreated biological sample. A difference in the amount of protein between the two samples is indicative of a toxic response to the test compound in the treated sample.

Microarrays may be prepared, used, and analyzed using methods known in ft art. (See, e.g., Brennan, T. M. et al. (1995) U.S. Pat. No. 5,474,796; Schena, M. et al. (1996) Proc. Natl. Acad. Sci. USA 93:10614-10619; Baldeschweiler et al. (1995) PCT application WO95/251116; Shalon, D. et al. (1995) PCT application WO95/35505; Heller, R. A. et al. (1997) Proc. Natl. Acad. Sci. USA 94:2150-2155; and Heller, M. J. et al. (1997) U.S. Pat. No. 5,605,662.) Various types of microarrays are well known and thoroughly described in *DNA Microarrays: A Practical Approach*, M. Schena, ed. (1999) Oxford University Press, London, hereby expressly incorporated by reference.

In another embodiment of the invention, nucleic acid sequences encoding LME may be used to generate hybridization probes useful in mapping the naturally occurring genomic sequence. Either coding or noncoding sequences may be used, and in some, instances, noncoding sequences may be preferable over coding sequences. For example, conservation of a coding sequence among members of a multi-gene family may potentially cause undesired cross hybridization during chromosomal mapping. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Harrington, J. J. et al. (1997) Nat. Genet 15:345-355; Price, C. M. (1993) Blood Rev. 7:127-134; and Trask, B. J. (1991) Trends Genet. 7:149-154.) Once mapped, the nucleic acid sequences of the invention may be used to develop genetic linkage maps, for example, which correlate the inheritance of a disease state with the inheritance of a particular chromosome region or restriction fragment length polymorphism (RFLP). (See, for example, Lander, E. S. and D. Botstein (1986) Proc. Natl. Acad. Sci. USA 83:7353-7357.)

Fluorescent in situ hybridization (FISH) may be correlated with other physical and genetic map data. (See, e.g., Heinz-Ulrich, et al. (1995) in Meyers, supra, pp. 965-968.) Examples of genetic map data can be found in various scientific journals or at the Online Mendelian Inheritance in Man (OMIM) World Wide Web site. Correlation between the location of the gem encoding LME on a physical map and a specific disorder, or a predisposition to a specific disorder, may help define the region of DNA associated with that disorder and thus may further positional cloning efforts.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the exact chromosomal locus is not known. This information is valuable to investigators searching for disease genes using positional cloning or other gene discovery techniques. Once the gene or genes responsible for a disease or syndrome have been crudely localized by genetic linkage to a particular genomic region, e.g., ataxia-telangiectasia to 11q22-23, any sequences mapping to that area may represent associated or regulatory genes for further investigation, (See, e.g., Gatti, R. A et alt (1988) Nature 336:577-580.) The nucleotide sequence of the instant invention may also be used to detect differences in the chromosomal location due to translocation, inversions etc., among normal, carrier, or affected individuals.

In another embodiment of the invention, LME, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between LME and the agent being tested may be measured.

Another technique for drug screening provides for high throughput screening of compounds having suitable binding affinity to the protein of interest. (See, e.g., Geyser et al. (1984) PCT application WO84/03564.) In this method, large numbers of different small test compounds are synthesized on a solid substrate. The test compounds are reacted with LME, or fragments thereof and washed. Bound LME is then detected by methods well known in the art. Purified LME can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding LME specifically compete with a test compound for binding LME. In this manner, antibodies can be used to detect the presence of any peptide which shares one or more antigenic determinants with LME.

In additional embodiments, the nucleotide sequences which encode LME may be used in any molecular biology techniques that have yet to be developed, provided the new techniques rely on properties of nucleotide sequences that are currently known, including, but not limited to, such properties as the triplet genetic code and specific base pair interactions.

Without further elaboration, it is believed that one skilled in the art can, using the preceding description, utilize the present invention to its fullest extent. The following embodiments are, therefore, to be construed as merely illustrative, and not limitative of the remainder of the disclosure in any way whatsoever.

The disclosures of all patents, applications and publications, mentioned above and below, including U.S. Ser. No. 60/186,480, U.S. Ser. No. 60/190,415, and U.S. Ser. No. 60/198,437, are expressly incorporated by reference herein.

EXAMPLES

I. Construction of cDNA Libraries

Incyte cDNAs were dived from cDNA libraries described in the LIFESEQ GOLD database (Incyte Genomics, Palo Alto Calif.) and shown in Table 4, column 5. Some tissues were homogenized and lysed in guanidinium isothiocyanate, while others were homogenized and lysed in phenol or in a suitable mixture of denaturants, such as TRIZOL (Life Technologies), a monophasic solution of phenol and guanidine isothiocyanate. The resulting lysates were centrifuged over CsCl cushions or extracted with chloroform. RNA was precipitated from the lysates with either isopropanol or sodium acetate and ethanol, or by other routine methods.

Phenol extraction and precipitation of RNA were repeated as necessary to increase RNA purity. In some cases, RNA was treated with DNase. For most libraries, poly(A)+ RNA was isolated using oligo d(T)-coupled paramagnetic particles (Promega), OLIGOTEX latex particles (QIAGEN, Chatsworth Calif.), or an OLIGOTEX mRNA purification kit (QIAGEN). Alternatively, RNA was isolated directly from tissue lysates using other RNA isolation kits, e.g., the POLY(A)PURE mRNA purification kit (Ambion, Austin Tex.).

In some cases, Stratagene was provided with RNA and constructed the corresponding cDNA libraries. Otherwise, cDNA was synthesized and cDNA libraries were constructed with the UNIZAP vector system (Stratagene) or SUPERSCRIPT plasmid system (Life Technologies), using the recommended procedures or similar methods known in the art. (See e.g., Ansubel, 1997, supra, units 5.1-6.6.) Reverse transcription was initiated using oligo d(T) or random primers. Synthetic oligonucleotide adapters were ligated to double stranded cDNA, and the cDNA was digested with the appropriate restriction enzyme or enzymes. For most libraries, the cDNA was size-selected (300-1000 bp) using SEPHACRYL S1000, SEPHAROSE CL2B, or SEPHAROSE CL4B column chromatography (Amersham Pharmacia Biotech) or preparative agarose gel electrophoresis. cDNAs were ligated into compatible restriction enzyme sites of the polylinker of a suitable plasmid, e.g., PBLUESCRIPT plasmid (Stratagene), PSPORT1 plasmid (Life Technologies), PCDNA2.1 plasmid (Invitrogen, Carlsbad Calif.), PBK-CMV plasmid (Stratagene), or pINCY (Incyte Genomics, Palo Alto Calif.), or derivatives thereof. Recombinant plasmids were transformed into competent *E. coli* cells including XL1-Blue, XL1-BlueMRF, or SOLR from Stratagene or DH5α, DH10B, or ElectroMAX DH10B from Life Technologies.

II. Isolation of cDNA Clones

Plasmids obtained as described in Example I were recovered from host cells by in vivo excision using the UNIZAP vector system (Stratagene) or by cell lysis. Plasmids were purified using at least one of the following: a Magic or WIZARD Minipreps DNA purification system (Promega); an AGTC Miniprep purification kit (Edge Biosystems, Gaithersburg Md.); and QIAWELL 8 Plasmid, QIAWELL 8 Plus Plasmid, QIAWELL 8 Ultra Plasmid purification systems or the R.E.A.L. PREP 96 plasmid purification kit from QIAGEN. Following precipitation, plasmids were resuspended in 0.1 ml of distilled water and stored, with or without lyophilization, at 4° C.

Alternatively, plasmid DNA was amplified from host cell lysates using direct link PCR in a high-throughput format (Rao, V. B. (1994) Anal. Biochem. 216:1-14). Host cell lysis and thermal cycling steps were carried out in a single reaction mixture. Samples were processed and stored in 384-well plates, and the concentration of amplified plasmid DNA was quantified fluorometrically using PICOGREEN dye (Molecular Probes, Eugene Oreg.) and a FLUOROSKAN II fluorescence scanner (Labsystems Oy, Helsinki, Finland).

III. Sequencing and Analysis

Incyte cDNA recovered in plasmids as described in Example II were sequenced as follows. Sequencing reactions were processed using standard methods or high-throughput instrumentation such as the ABI CATALYST 800 (Applied Biosystems) thermal cycler or the PTC-200 thermal cycler (MJ Research) in conjunction with the HYDRA microdispenser (Robbins Scientific) or the MICROLAB 2200 (Hamilton) liquid transfer system. cDNA sequencing reactions were prepared using reagents provided by Amersham Pharmacia Biotech or supplied in ABI sequencing kits such as the ABI PRISM BIGDYE Terminator cycle sequencing ready reaction kit (Applied Biosystems). Electrophoretic separation of cDNA sequencing reactions and detection of labeled polynucleotides were carried out using the MEGABACE 1000 DNA sequencing system (Molecular Dynamics); the ABI PRISM 373 or 377 sequencing system (Applied Biosystems) in conjunction with standard ABI protocols and base calling software; or other sequence analysis systems known in the art. Reading frames within the cDNA sequences were identified using standard methods (reviewed in Ausubel, 1997, supra, unit 7.7). Some of the cDNA sequences were selected for extension using the techniques disclosed in Example VIII.

The polynucleotide sequences derived from Incyte cDNAs were validated by removing vector, linker, and poly(A) sequences and by masking ambiguous bases, using algorithms and programs based on BLAST, dynamic programming, and dinucleotide nearest neighbor analysis. The Incyte cDNA sequences or translations thereof were then queried against a selection of public databases such as the GenBank primate, rodent, mammalian, vertebrate, and eukaryote databases, and BLOCKS, PRINTS, DOMO, PRODOM, and hidden Markov model (HMM)-based protein family databases such as PFAM. (HMM is a probabilistic approach which analyzes consensus primary structures of gene families. See, for example, Eddy, S. R. (1996) Curr. Opin. Struct. Biol. 6:361-365.) The queries were performed using programs based on BLAST, FASTA, BLIPS, and HMMER. The Incyte cDNA sequences were assembled to produce full length polynucleotide sequences. Alternatively, GenBank cDNAs, GenBank ESTs, stitched sequences, stretched sequences or Genscan-predicted coding sequences (see Examples IV and V) were used to extend Incyte cDNA assemblages to full length. Assembly was performed using programs based on Phred, Phrap, and Consed, and cDNA assemblages were screened for open reading frames using programs based on GeneMark, BLAST, and PASTA. The full length polynucleotide sequences were translated to derive the corresponding toll length polypeptide sequences. Alternatively, a polypeptide of the invention may begin at any of the methionine residues of the full length translated polypeptide. Full length polypeptide sequences were subsequently analyzed by querying against databases such as the GenBank protein databases (genpept), SwissProt, BLOCKS, PRINTS, DOMO, PRODOM, Prosite, and hidden Markov model (HMM-based protein family databases such as PFAM. Full length polynucleotide sequences are also analyzed using MACDNASIS PRO software (Hitachi Software Engineering, South San Francisco Calif.) and LASERGENE software (DNASTAR). Polynucleotide and polypeptide sequence alignments are generated using default parameters specified by the CLUSTAL algorithm as incorporated into the MEGALIGN multisequence alignment program (DNASTAR), which also calculates the percent identity between aligned sequences.

Table 7 summarizes the tools, programs, and algorithms used for the analysts and assembly of Incyte cDNA and full length sequences and provides applicable descriptions, references, and threshold parameters. The first column of Table 7 shows the tools, programs, and algorithms used, the second column provides brief descriptions thereof, the third column presents appropriate references, all of which are incorporated by reference herein in their entirety, and the fourth column presents, where applicable, the scores, probability values, and other parameters used to evaluate the strength of a match between two sequences (the higher the score or the lower the probability value, the greater the identity between two sequences).

The programs described above for the assembly and analysis of full length polynucleotide and polypeptide sequences were also used to identify polynucleotide sequence fragments from SEQ ID NO:7-12. Fragments from about 20 to about 4000 nucleotides which are useful in hybridization and amplification technologies are described in Table 4, column 4.

IV. Identification and Editing of Coding Sequences from Genomic DNA

Putative lipid metabolism enzymes were initially identified by run the Genscan gene identification program against public genomic sequence databases (e.g. gbpri and gbhtg). Genscan is a general-purpose gene identification program which analyzes genomic DNA sequences from a variety of organisms (See Burge, C. and S. Karlin (1997) J. Mol. Biol. 268:78-94, and Burge, C and S. Karlin (1998) Curr. Opin. Struct. Biol. 8:346-354). The program concatenates predicted exons to form an assembled cDNA sequence extending from a methionine to a stop codon. The output of Genscan is a FASTA database of polynucleotide and polypeptide sequences. The maximum range of sequence for Genscan to analyze at once was set to 30 kb. To determine which of these Genscan predicted cDNA sequences encode lipid metabolism enzymes, the encoded polypeptides were analyzed by querying against PFAM models for lipid metabolism enzymes. Potential lipid metabolism enzymes were also identified by homology to Incyte cDNA sequences that had been annotated as lipid metabolism enzymes. These selected Genscan-predicted sequences were then compared by BLAST analysis to the genpept and gbpri public databases. The necessary, the Genscan-predicted sequences were then edited by comparison to the top BLAST hit from genpept to correct errors in the sequence predicted by Genscan, such as extra or omitted exons. BLAST analysis was also used to find any Incyte cDNA or public cDNA coverage of the Genscan-predicted sequences, thus providing evidence for transcription. When Incyte cDNA coverage was available, this information was used to correct or confirm the Genscan predicted sequence. Full length polynucleotide sequences were obtained by assembling Genscan-predicted coding sequences with Incyte cDNA sequences and/or public cDNA sequences using the assembly process described in Example III. Alternatively, full length polynucleotide sequences were derived entirely from edited a unedited Genscan-predicted coding sequences.

V. Assembly of Genomic Sequence Data with cDNA Sequence Data

"Stitched" Sequences

Partial cDNA sequences were extended with exons predicted by the Genscan gene identification program described in Example IV. Partial cDNAs assembled as described in Example III were mapped to genomic DNA and parsed into clusters containing related cDNAs and Genscan exon predictions from one or more genomic sequences. Each cluster was analyzed using an algorithm based on graph theory and dynamic programming to integrate cDNA and genomic information, generating possible splice variants that were subsequently confirmed, edited, or extended to create a full length sequence. Sequence intervals in which the entire length of the interval was present on more than one sequence in the cluster were identified, and intervals thus identified were considered to be equivalent by transitivity. For example, if an interval was present on a cDNA and two genomic sequences, then all three intervals were considered to be equivalent. This process allows unrelated but consecutive genomic sequences to be brought together, bridged by cDNA sequence. Intervals thus identified were then "stitched" together by the stitching algorithm in the order that they appear along their parent sequences to generate the longest possible sequence, as well as sequence variants. Linkages between intervals which proceed along one type of parent sequence (cDNA to cDNA or genomic sequence to genomic sequence) were given preference over linkages which change parent type (cDNA to genomic sequence). The resultant stitched sequences were translated and compared by BLAST analysis to the genpept and gbpri public databases. Incorrect exons predicted by Genscan wore corrected by comparison to the top BLAST hit from genpept. Sequences were further extended with additional cDNA sequences, or by inspection of genomic DNA, when necessary.

"Stretched" Sequences

Partial DNA sequences were extended to full length with an algorithm based on BLAST analysis. First, partial cDNAs assembled as described in Example III were queried against public databases such as the GenBank primate, rodent, mammalian, vertebrate, and eukaryote databases using the BLAST program. The nearest GenBank protein homolog was then compared by BLAST analysis to either Incyte cDNA sequences or GenScan exon predicted sequences described in Example IV. A chimeric protein was generated by using the resultant high-scoring segment pains (HSPs) to map the translated sequences onto the GenBank protein homolog. Insertions or deletions may occur in the chimeric protein with respect to the original GenBank protein homolog. The GenBank protein homolog, the chimeric protein, or both were used as probes to search for homologous genomic sequences from the public human genome databases. Partial DNA sequences were therefore "stretched" or extended by the addition of homologous genomic sequences. The resultant stretched sequences were examined to determine whether it contained a complete gem.

VI. Chromosomal Mapping of LME Encoding Polynucleotides

The sequences which were used to assemble SEQ ID NO:7-12 were compared with sequences from the Incyte LIFESEQ database and public domain databases using BLAST and other implementations of the Smith-Waterman algorithm. Sequences from these databases that matched SEQ ID NO:7-12 were assembled into clusters of contiguous and overlapping sequences using assembly algorithms such as Phrap (Table 7). Radiation hybrid and genetic mapping data available from public resources such as the Stored Human Genome Center (SHGC), Whitehead Institute for Genome Research (WIGR), and Généthon were used to determine if any of the clustered sequences had been previously mapped. Inclusion of a mapped sequence in a cluster resulted in the assignment of all sequences of that cluster, including its particular SEQ ID NO:, to that map location.

Map locations are represented by ranges, or intervals, or human chromosomes. The map position of an interval, in centiMorgans, is measured relative to the terminus of the chromosome's p-arm. (The centiMorgan (cM) is a unit of measurement based on recombination frequencies between chromosomal markers. On average, 1 cM is roughly equivalent to 1 megabase (Mb) of DNA in humans, although this can vary widely due to hot and cold spots of recombination.) The cM distances are based on genetic markers mapped by Genethon which provide boundaries for radiation hybrid markers whose sequences were included in each of the clusters. Human genome maps and other resources available to the public, such as the NCBI "GeneMap'99" on the internet, can be employed to determine if previously identified disease genes map within or in proximity to the intervals indicated above.

VII. Analysis of Polynucleotide Expression

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; Ausubel (1995) supra, ch. 4 and 16.)

Analogous computer techniques applying BLAST were used to search for identical or related molecules in cDNA databases such as GenBank or LIFESEQ (Incyte Genomics). This analysis is much faster than multiple membrane-based hybridizations. In addition, the sensitivity of the computer search can be modified to determine whether any particular match is categorized as exact or similar. The basis of the search is the product score, which is defined as:

$$\frac{\text{BLAST Score} \times \text{Percent Identity}}{5 \times \text{minimum\{length}(Seq.\ 1), \text{length}(Seq.\ 2)\}}$$

The product score takes into account both the degree of similarity between two sequences and the length of the sequence match. The product score is a normalized value between 0 and 100, and is calculated as follows: the BLAST score is multiplied by the percent nucleotide identity and the product is divided by (5 times the length of the shorter of the two sequences). The BLAST score is calculated by assigning a score of +5 for every base that matches in a high-scoring segment pair (HSP), and -4 for every mismatch. Two sequences may share more than one HSP (separated by gaps). If there is more than one HSP, ten the pair with the highest BLAST score is used to calculate the product score. The product score represents a balance between fractional overlap and quality in a BLAST alignment. For example, a product score of 100 is produced only for 100% identity over the entire length of the shorter of the two sequences being compared. A product score of 70 is produced either by 100% identity and 70% overlap at one end, or by 88% identity and 100% overlap at the other. A product score of 50 is produced either by 100% to identity and 50% overlap at one end, or 79% identity and 100% overlap.

Alternatively, polynucleotide sequences encoding LME are analyzed with respect to the tissue sources from which they were derived. For example, some full length sequences are assembled, at least in part, with overlapping Incyte cDNA sequences (see Example III). Each cDNA sequence is derived from a cDNA library constructed from a human tissue. Each human tissue is classified into one of the following organ/tissue categories: cardiovascular system; connective tissue; digestive system; embryonic structures; endocrine system exocrine glands; genitalia, female; genitalia, male; germ cells; hemic and immune system, liver; musculoskeletal system; nervous system; pancreas; respiratory system; sense organs; skin; stomatognathic system; unclassified/mixed; or urinary tract. The number of libraries in each category is counted and divided by the total number of libraries across all categories. Similarly, each human tissue is classified into one of the following disease/condition categories: cancer, cell line, developmental, inflammation, neurological, trauma, cardiovascular, pooled, and other, and the number of libraries in each category is counted and divided by the total number of libraries across all categories. The resulting percentages reflect the tissue- and disease-specific expression of cDNA encoding LME. cDNA sequences and cDNA library/tissue information are found in the LIFESEQ GOLD database (Incyte Genomics, Palo Alto Calif.).

VIII. Extension of LME Encoding Polynucleotides

Full length polynucleotide sequences were also produced by extension of an appropriate fragment of the full length molecule using oligonucleotide primers designed from this fragment. One primer was synthesized to initiate 5 extension of the known fragment, and the other primer was synthesized to initiate 3' extension of the known fragment. The initial primers were designed using OLIGO 4.06 software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries were used to extend the sequence. If more than one extension was necessary or desired, additional or nested sets of primers were designed.

High fidelity amplification was obtained by PCR using methods well known in the art. PCR was performed in 96-well plates using the PTC-200 thermal cycler (MJ Research, Inc.). The reaction mix contained DNA template, 200 nmol of each primer, reaction buffer containing $Mg^{2+}$, $(NH_4)_2SO_4$, and 2-mercaptoethanol, Taq DNA polymerase (Amersham Pharmacia Biotech), ELONGASE enzyme (Life Technologies), and Pfu DNA polymerase (Stratagene), with the following parameters for primer pair PCI A and PCI B: Step 1: 94° C., 3 min; Step 2: 94° C., 15 sec; Step 3: 60° C., 1 min; Step 4: 68° C., 2 min; Step 5: Steps 2, 3, and 4 repeated 20 times; Step 6: 68° C., 5 min; Step 7: storage at 4° C. In the alternative, the parameters for primer pair T7 and SK+ were as follows: Step 1: 94° C., 3 min; Step 2: 94° C., 15 sec; Step 3: 57° C., 1 min; Step 4: 68° C., 2 min; Step 5: Steps 2, 3, and 4 repeated 20 times; Step 6: 68° C., 5 min; Step 7: storage at 4° C.

The concentration of DNA in each well was determined by dispensing 100 μl PICOGREEN quantitation reagent (0.25% (v/v) PICOGREEN; Molecular Probes, Eugene Oreg.) dissolved in 1×TE and 0.5 μl of undiluted PCR product into each well of an opaque fluorimeter plate (Corning Costar, Acton Mass.), allowing the DNA to bind to the reagent. The plate was scanned in a Fluoroskan II (Labsystems Oy, Helsinki, Finland) to measure the fluorescence of the sample and to quantify the concentration of DNA. A 5 μl to 10 μl aliquot of the reaction mixture was analyzed by electrophoresis on a 1% agarose gel to determine which reactions were successful in extending the sequence.

The extended nucleotides were desalted and concentrated, transferred to 384-well plates, digested with CviJI cholera virus endonuclease (Molecular Biology Research, Madison Wis.), and sonicated or sheared prior to religation into pUC 18 vector (Amersham Pharmacia Biotech). For shotgun sequencing, the digested nucleotides were separated on low concentration (0.6 to 0.8%) agarose gels, fragments were excised, and agar digested with Agar ACE Promega). Extended clones were religated using T4 ligase (New England Biolabs, Beverly Mass.) into pUC 18 vector (Amersham Pharmacia Biotech), treated with Pfu DNA polymerase (Stratagene) to fill-in restriction site overhangs, and transfected into competent *E. coli* cells. Transformed cells were selected on antibiotic-contain media, and individual colonies were picked and cultured overnight at 37° C. in 384-well plates in LB/2× carb liquid media.

The cells were lysed, and DNA was amplified by PCR using Taq DNA polymerase (Amersham Pharmacia Biotech) and Pfu DNA polymerase (Stratagene) with the following parameters: Step 1: 94° C., 3 min; Step 2: 94° C., 15 sec; Step 3: 60° C., 1 min; Step 4: 72° C., 2 min; Step 5: steps 2, 3, and 4 repeated 29 times; Step 6: 72° C., 5 min; Step 7: storage at 4° C. DNA was quantified by PICOGREEN reagent (Molecular Probes) as described above. Samples with low DNA recoveries were reamplified using the same conditions as described above. Samples were diluted with 20% dimethylsulfoxide (1:2, v/v), and sequenced using DYENAMIC energy transfer sequencing primers and the DYENAMIC DIRECT kit (Amersham Pharmacia Biotech) or the ABI PRISM BIGDYE Terminator cycle sequencing ready reaction kit (Applied Biosystems).

In like manner, fall length polynucleotide sequences are verified using the above procedure or are used to obtain 5' regulatory sequences using the above procedure along with oligonucleotides designed for such extension, and an appropriate genomic library.

IX. Labeling and Use of Individual Hybridization Probes

Hybridization probes derived from SEQ ID NO:7-12 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 pmol of each oligomer, 250 μCi of [γ-$^{32}$P] adenosine triphosphate (Amersham Pharmacia Biotech), and T4 polynucleotide kinase DuPont NEN, Boston Mass.). The labeled oligonucleotides are substantially purified using a SEPHADEX G-25 superfine size exclusion dextran bead column (Amersham Pharmacia Biotech). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba I, or Pvu II (DuPont NEN).

The DNA from each digest is fractionated on a 0.7% agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under conditions of up tot for example, 0.1× saline sodium citrate and 0.5% sodium dodecyl sate. Hybridization patterns are visualized using autoradiography or an alternative imaging means and compared.

X. Microarrays

The linkage or synthesis of array elements upon a microarray can be achieved utilizing photolithography, piezoelectric printing (ink-jet printing, See e.g., Baldeschweiler, supra.), mechanical microspotting technologies, and derivatives thereof. The substrate in each of the aforementioned technologies should be uniform and solid with a non-porous surface (Schena (1999), supra). Suggested substrates include silicon, silica, glass slides, glass chips, and silicon wafers. Alternatively, a procedure analogous to a dot or slot blot may also be used to arrange and link elements to the surface of a substrate using thermal, UV, chemical, or mechanical bonding procedures. A typical array may be produced using available methods and machines well known to those of ordinary skill in the art and may contain any appropriate number of elements. (See, e.g., Schena, M. et al. (1995) Science 270:467-470; Shalon, D. et al. (1996) Genome Res. 6:639-645; Marshall, A and J. Hodgson (1998) Nat. Biotechnol. 16:27-31.)

Full length cDNAs, Expressed Sequence Tags (ESTs), or fragments or oligomers thereof may comprise the elements of the microarray. Fragments or oligomers suitable for hybridization can be selected using software well known in the art such as LASERGENE software (DNASTAR). The array elements are hybridized with polynucleotides in a biological sample. The polynucleotides in the biological sample are conjugated to a fluorescent label or other molecular tag for ease of detection. After hybridization, nonhybridized nucleotides from the biological sample are removed, and a fluorescence scanner is used to detect hybridization at each array element. Alternatively, laser desorption and mass spectrometry may be used for detection of hybridization. The degree of complementarity and the relative abundance of each polynucleotide which hybridizes to an element on the microarray may be assessed. In one embodiment, microarray preparation and usage is described in detail below.

Tissue or Cell Sample Preparation

Total RNA is isolated from tissue samples using the guanidinium thiocyanate method and poly(A)$^+$ RNA is purified using the oligo-(dT) cellulose method. Each poly (A)$^+$ RNA sample is reverse transcribed using MMLV reverse-transcriptase, 0.05 pg/µl oligo-(dT) primer (21mer), 1× first strand buffer, 0.03 units/µl RNase inhibitor, 500 µM dATP, 500 µM dGTP, 500 µM dTTP, 40 µM dCTP 40 µM dCTP-Cy3 (BDS) or dCTP-Cy5 (Amersham Pharmacia Biotech). The reverse transcription reaction is performed in a 25 ml volume containing 200 ng poly(A)$^+$ RNA with GEMBRIGHT kits (Incyte). Specific control poly(A)$^+$ RNAs are synthesized by in vitro transcription from non-coding yeast genomic DNA. After incubation at 37° C. for 2 hr, each reaction sample (one with Cy3 and another with Cy5 labeling) is treated with 2.5 ml of 0.5M sodium hydroxide and incubated for 20 minutes at 85° C. to the stop the reaction and degrade the RNA. Samples are purified using two successive CHROMA SPIN 30 gel filtration spin columns (CLONTECH Laboratories, Inc. (CLONTECH), Palo Alto Calif.) and after combining, both reaction samples are ethanol precipitated using 1 ml of glycogen (1 mg/ml), 60 ml sodium acetate, and 300 ml of 100% ethanol. The sample is then dried to completion using a SpeedVAC (Savant Instruments Inc. Holbrook N.Y.) and resuspended in 14 µl 5×SSC/ 0.2% SDS.

Microarray Preparation

Sequences of the present invention are used to generate array elements. Each array element is amplified from bacterial cells containing vectors with cloned cDNA inserts. PCR amplification uses primers complementary to the vector sequences flanking the cDNA insert. Array elements are amplified in thirty cycles of PCR from an initial quantity of 1-2 ng to a final quantity greater than 5 µg. Amplified array elements are then purified using SEPHACRYL-400 (Amersham Pharmacia Biotech).

Purified array elements are immobilized on polymer-coated glass slides. Glass microscope slides (Corning) are cleaned by ultrasound in 0.1% SDS and acetone, with extensive distilled water washes between and after treatments. Glass slides are etched in 4% hydrofluoric acid (VWR Scientific Products Corporation (VWR), West Chester Pa.), washed extensively in distilled water, and coated with 0.05% aminopropyl silane (Sigma) in 95% ethanol. Coated slides are cured in a 110° C. oven.

Array elements are applied to the coated glass substrate using a procedure described in U.S. Pat. No. 5,807,522, incorporated herein by reference. 1 µl of the array element DNA, at an average concentration of 100 ng/µl, is loaded into the open capillary printing element by a high-speed robotic apparatus. The apparatus then deposits about 5 nl of array element sample per slide.

Microarrays are UV-crosslinked using a STRATALINKER UV-crosslinker (Stratagene). Microarrays are washed at room temperature once in 0.2% SDS and three times in distilled water. Non-specific binding sits are blocked by incubation of microarrays in 0.2% casein in phosphate buffered saline (PBS) (Tropix, Inc., Bedford Mass.) for 30 minutes at 60° C. followed by washes in 0.2% SDS and distilled water as before.

Hybridization

Hybridization reactions contain 9 µl of sample mixture consisting of 0.2 µg each of Cy3 and Cy5 labeled cDNA synthesis products in 5×SSC, 0.2% SDS hybridization buffer. The sample mixture is heated to 65° C. for 5 minutes and is aliquoted onto the microarray surface and covered with an 1.8 cm$^2$ coverslip. The arrays are transferred to a waterproof chamber having a cavity just slightly larger than a microscope slide. The chamber is kept at 100% humidity internally by the addition of 140 µl of 5×SSC in a corner of the chamber. The chamber containing the arrays is incubated for about 6.5 hours at 60° C. The arrays are washed for 10 min at 45° C. in a first wash buffer (1×SSC, 0.1% SDS), three times for 10 minutes each at 450 in a second wash buffer (0.1×SSC), and dried.

Detection

Reporter-labeled hybridization complexes are detected with a microscope equipped with an Innova 70 mixed gas 10 W laser (Coherent, Inc., Santa Clara Calif.) capable of generating spectral lines at 488 nm for excitation of Cy3 and at 632 nm for excitation of Cy5. The excitation laser light is focused on the array using a 20× microscope objective (Nikon, Inc., Melville N.Y.). The slide containing the array is placed on a computer-controlled X-Y stage on the microscope and raster-scanned past the objective. The 1.8 cm×1.8 cm array used in the present example is scanned with a resolution of 20 micrometers.

In two separate scans, a mixed gas multiline laser excites the two fluorophores sequentially. Emitted light is split, based on wavelength, into two photomultiplier tube detectors (PMT R1477, Hamamatsu Photonics Systems, Bridgewater N.J.) corresponding to the two fluorophores. Appropriate filters positioned between the array and the photomultiplier tubes are used to filter the signals. The emission maxima of the fluorophores used are 565 nm for Cy3 and 650 nm for Cy5. Each array is typically scanned twice, one scan per fluorophore using the appropriate filters at the laser source, although the apparatus is capable of recording the spectra from both fluorophores simultaneously.

The sensitivity of the scans is typically calibrated using the signal intensity generated by a cDNA control species added to the sample mixture at a known concentration. A specific location on the array contains a complementary DNA sequence, allowing the intensity of the signal at that location to be correlated with a weight ratio of hybridizing species of 1:100,000. When two samples from different sources (e.g., representing test and control cells), each labeled with a different fluorophore, are hybridized to a single array for the purpose of identifying genes that are differentially expressed, the calibration is done by labeling samples of the calibrating cDNA with the two fluorophores and adding identical amounts of each to the hybridization mixture.

The output of the photomultiplier tube is digitized using a 12-bit RTI-835H analog-to-digital (A/D) conversion board (Analog Devices, Inc., Norwood Mass.) installed in an IBM-compatible PC computer. The digitized data are displayed as an image where the signal intensity is mapped using a linear 20-color transformation to a pseudocolor scale ranging from blue (low signal) to red (high signal). The data is also analyzed quantitatively. Where two different fluorophores are excited and measured simultaneously, the data are first corrected for optical crosstalk (due to overlapping emission spectra) between the fluorophores using each fluorophore's emission spectrum.

A grid is superimposed over the fluorescence signal image such that the signal from each spot is centered in each element of the grid. The fluorescence signal win each element is then integrated to obtain a numerical value corresponding to the average intensity of the signal. The software used for signal analysis is the GEMTOOLS gene expression analysis program (Incyte).

XI. Complementary Polynucleotides

Sequences complementary to the LME-encoding sequences, or any parts thereof are used to detect, decrease, or inhibit expression of naturally occurring LME. Although use of oligonucleotides comprising from about 15 to 30 base pairs is described, essentially the same procedure is used with smaller or with larger sequence fragments. Appropriate oligonucleotides are designed using OLIGO 4.06 software (National Biosciences) and the coding sequence of LME. To inhibit transcription, a complementary oligonucleotide is designed from the most unique 5' sequence and used to prevent promoter binding to the coding sequence. To inhibit translation, a complementary oligonucleotide is designed to prevent ribosomal binding to the LME-encoding transcript.

XII. Expression of LME

Expression and purification of LME is achieved using bacterial or virus-based expression systems. For expression of LME in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21(DE3). Antibiotic resistant bacteria express LME upon induction with isopropyl beta-D-thiogalactopyranoside (IPTG). Expression of LME in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus. (See Engelhard, E. K. et al. (1994) Proc. Natl. Acad. Sci. USA 91:3224-3227; Sandig, V. et al. (1996) Hum. Gene Ther. 7:1937-1945.)

In most expression systems, LME is synthesized as a fusion protein with, e.g., glutathione S-transferase (GST) or a peptide epitope tag, such as FLAG or 6-His, permitting rapid, single-step, affinity-based purification of recombinant fusion protein from crude cell lysates. GST, a 26-kilodalton enzyme from *Schistosoma japonicum*, enables the purification of fusion proteins on immobilized glutathione under conditions that maintain protein activity and antigenicity (Amersham Pharmacia Biotech). Following purification, the GST moiety can be proteolytically cleaved from LME at specifically engineered sites. FLAG, an 8-amino acid peptide, enables immunoaffinity purification using commercially available monoclonal and polyclonal anti-FLAG antibodies (Eastman Kodak). 6-His, a stretch of six consecutive histidine residues, enables purification on metal-chelate resins (QIAGEN). Methods for protein expression and purification are discussed in Ausubel (1995, supra, ch. 10 and 16). Purified LME obtained by these methods can be used directly in the assays shown in Examples XVI and XVII, where applicable.

XIII. Functional Assays

LME function is assessed by expressing the sequences encoding LME at physiologically elevated levels in mammalian cell culture systems. cDNA is subcloned into a mammalian expression vector containing a strong promoter that drives nigh levels of cDNA expression. Vectors of choice include PCMV SPORT (Life Technologies) and PCR3.1 (Invitrogen, Carlsbad Calif.), both of which contain the cytomegalovirus promoter. 5-10 µg of recombinant vector are transiently transfected into a human cell line, for example, an endothelial or hematopoietic cell line, using either liposome formulations or electroporation. 1-2 µg of an additional plasmid containing sequences encoding a marker protein are co-transfected. Expression of a marker protein provides a means to distinguish transfected cells from non-transfected cells and is a reliable predictor of cDNA expression from the recombinant vector. Marker proteins of choice include, e.g., Green Fluorescent Protein (GFP; Clontech), CD64, or a CD64-GFP fusion protein. Flow cytometry (FCM), an automated, laser optics-based technique, is used to identify transfected cells expressing GFP or CD64-GFP and to evaluate the apoptotic state of the cells and other cellular properties. FCM detects and quantifies the uptake of +fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) Flow Cytometry, Oxford, New York N.Y.

The influence of LME on gene expression can be assessed using highly purified populations of cells transfected with sequences encoding LME and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success N.Y.). mRNA can be purified from the cells using methods well known by those of skill in the art. Expression of mRNA encoding LME and other genes of interest can be analyzed by northern analysis or microarray techniques.

XIV. Production of LME Specific Antibodies

LME substantially purified using polyacrylamide gel electrophoresis (PAGE; see, e.g., Harrington, M. G. (1990) Methods Enzymol. 182:488-495), or other purification techniques, is used to immunize rabbits and to produce antibodies using standard protocols.

Alternatively, the LME amino add sequence is analyzed using LASERGENE software (DNASTAR) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art (See, e.g., Ausubel, 1995, supra, ch. 11.)

Typically, oligopeptides of about 15 residues in length are synthesized using an ABI 431A peptide synthesizer (Applied Biosystems) using FMOC ch and coupled to KLH (Sigma-Aldrich, St. Louis Mo.) by reaction with N-maleimidobenzoyl-N-hydroxysuccinimide ester (MBS) to increase immunogenicity. (See e.g., Ausubel, 1995, supra.) Rabbits are immunized with the oligopeptide-KLH complex in complete Freund's adjuvant. Resulting antisera are tested for antipeptide and anti-LME activity by, for example, binding the peptide or LME to a substrate, blocking with 1% BSA, reacting with rabbit antisera, washing, and reacting with radio-iodinated goat anti-rabbit IgG.

XV. Purification of Naturally Occurring LME Using Specific Antibodies

Naturally occurring or recombinant LME is substantially purified by immunoaffinity chromatography using antibodies specific for LME. An immunoaffinity column is constructed by covalently coupling anti-LME antibody to an activated chromatographic resin, such as CNBr-activated SEPHAROSE (Amersham Pharmacia Biotech). After the coupling, the resin is blocked and washed according to the manufacturer's instructions.

Media containing LME are passed over the immunoaffinity column and the column is washed under conditions that allow the preferential absorbance of LME (e.g., high ionic strength buffers in the presence of detergent). The column is eluted under conditions that disrupt antibody/LME binding (e.g., a buffer of pH 2 to pH 3, or a high concentration of a chaotrope, such as urea or thiocyanate ion), and LME is collect.

XVI. Identification of Molecules which Interact with LME

LME, or biologically active fragments thereof are labeled with $^{125}$I Bolton-Hunter reagent. (See, e.g., Bolton A. E. and W. M. Hunter (1973) Biochem. J. 133:529-539.) Candidate molecules previously arrayed in the wells of a multi-well plate are incubated with the labeled LME, washed, and any wells with labeled LME complex are assayed. Data obtained using different concentrations of LME are used to calculate values for the number, affinity, and association of LME with the candidate molecules.

Alternatively, molecules interacting with LME are analyzed using the yeast two-hybrid system as described in Fields, S. and O. Song (1989) Nature 340:245-246, or using commercially available kits based on the two-hybrid system, such as the MATCHMAKER system (Clontech).

LME may also be used in the PATHCALLING process (CuraGen Corp., New Haven Conn.) which employs the yeast two-hybrid system in a high-throughput manner to determine all interactions between the proteins encoded by two large libraries of genes (Nandabalan, K. et al. (2000) U.S. Pat. No. 6,057,101).

XVII. Demonstration of LME Activity

LME activity can be demonstrated by an in vitro hydrolysis assay with vesicles containing 1-palmitoyl-2-[1-$^{14}$C] oleoyl phosphatidylcholine (Sigma-Aldrich). LME triglyceride lipase activity and phospholipase $A_2$ activity are demonstrated by analysis of the cleavage products isolated from the hydrolysis reaction mixture.

Vesicles containing 1-palmitoyl-2-[1-$^{14}$C]oleoyl phosphatidylcholine (Amersham Pharmacia Biotech.) are prepared by mixing 2.0 µCi of the radiolabeled phospholipid with 12.5 mg of unlabeled 1-palmitoyl-2-oleoyl phosphatidylcholine and drying the mixture under $N_2$. 2.5 ml of 150 mM Tris-HCl, pH 7.5, is added, and the mixture is sonicated and centrifuged. The supernatant may be stored at 4° C. The final reaction mixture is contain 0.25 ml of Hanks buffered salt solution supplemented with 2.0 mM taurchenodeoxycholate, 1.0% bovine serum albumin, 1.0 mM $CaCl_2$, pH 7.4, 150 µg of 1-palmitoyl-2-[1-$^{14}$C]oleoyl phosphatidylcholine vesicles, and various amounts of LME diluted in PBS. After incubation for 30 min at 37° C., 20 µg each of lyso-phosphatidylcholine and oleic acid are added as carriers and each sample is extracted for total lipids. The lipids are separated by thin layer chromatography using a two solvent system of choroform:methanol:acetic acid:water (65:35:8:4) until the solvent front is halfway up the plate. The process is then continued with hexane:ether:acetic acid (86:16:1) until the solvent front is at the top of the plate. The lipid-containing areas are visualized with $I_2$ vapor; the spots are scraped, and their radioactivity is determined by scintillation counting. The amount of radioactivity released as fatty acids will increase as a greater amount of LME is added to the assay mixture while the amount of radioactivity released as lyso-phosphatidylcholine will remain low. This demonstrates that LME cleaves at the sn-2 and not the sn-1 position, as is characteristic of phospholipase $A_2$ activity.

Alternatively, LME phospholipase activity is measured by the hydrolysis of a fatty acyl residue at the sn-1 position of phosphatidylserine. LME is combined with the Tritium [$^3$H] labeled substrate phosphatidylserine at stoichiometric quantities in a suitable buffer. Following an appropriate incubation time, the hydrolyzed reaction products are separated from the substrates by chromatographic methods. The amount of acylglycerophosphoserine produced is measured by counting tritiated product with the help of a scintillation counter. Various control groups are set up to account for background noise and unincorporated substrate. The final counts represent the tritiated enzyme product [$^3$H]-acylglycerophosphoserine, which is directly proportional to the activity of LME in biological samples.

LME lipoxygenase activity can be measured by chromatographic methods. Extracted LME lipoxygenase protein is incubated with 100 μM [1-$^{14}$C] arachidonic acid or other unlabeled fatty acids at 37° C. for 30 min. After the incubation, stop solution (acetonitrile:methanol:water, 350:150:1) is added. The samples are extracted and analyzed by reverse-phase HPLC by using a solvent system of methanol/water/acetic acid, 85:15:0.01 (vol/vol) at a flow rate of 1 ml/min. The effluent is monitored at 235 nm and analyzed for the presence of the major arachidonic metabolite such as 12-HPETE (catalyzed by 12-LOX). The fractions are also subjected to liquid scintillation counting. The final counts represent the products, which is directly proportional to de activity of LME in biological samples. For stereochemical analysis, the metabolites of arachidonic acid are analyzed her by chiral phase-HPLC and by mass spectrometry (Sun, D. et al. (1998) J. Biol. Chem. 273:33540-33547).

Various modifications and variations of the described methods and systems of the invention will be apparent to those skilled in the art without departing from the scope and spirit of the invention. Although the invention has been described in connection with certain embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

TABLE 1

| Incyte Project ID | Incyte Polypeptide SEQ ID NO: | Incyte Polypeptide ID | Polynucleotide SEQ ID NO: | Incyte Polynucleotide ID |
|---|---|---|---|---|
| 2372651 | 1 | 2372651CD1 | 7 | 2372651CB1 |
| 2470792 | 2 | 2470792CD1 | 8 | 2470792CB1 |
| 1506182 | 3 | 1506182CD1 | 9 | 1506182CB1 |
| 2690842 | 4 | 2690842CD1 | 10 | 2690842CB1 |
| 5027764 | 5 | 5027764CD1 | 11 | 5027764CB1 |
| 2488174 | 6 | 2488174CD1 | 12 | 2488174CB1 |

TABLE 2

| Polypeptide SEQ ID NO: | Incyte Polypeptide ID | GenBank ID NO: | Probability Score | GenBank Homolog |
|---|---|---|---|---|
| 1 | 2372651CD1 | g3876901 | 2.50E−56 | Similarity to Human enoyl-CoA hydratase (SW: ECHM_HUMAN) [Caenorhabditis elegans] ((1998) Science 282: 2012-2018) |
| 2 | 2470792CD1 | g7024433 | 0 | Male sterility protein 2-like protein [Torpedo marmorata] |
| 3 | 1506182CD1 | g11245478 | 1.00E−162 | Nicotinamide mononucleotide adenylyl transferase [Homo sapiens] |
| 4 | 2690842CD1 | g6503307 | 3.20E−18 | Phospholipid biosynthetic acyltransferase family member [Arabidopsis thaliana] (Neuwald, A. F. (1997) Curr. Biol. 7: R465-466) |
| 5 | 5027764CD1 | g4090960 | 1.40E−64 | Phosphatidylserine-specific phospholipase A1 [Homo sapiens] (Nagai, Y. et al. (1999) J. Biol. Chem. 274: 1153-11059) |
| 6 | 2488174CD1 | g7274380 | 1.00E−151 | Group III secreted phospholipase A2 [Homo sapiens] (Valentin, E. et al. (2000) J. Biol. Chem. 275: 7492-7496) |

TABLE 3

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| 1 | 2372651CD1 | 303 | S49 S167 T233 S43 T69 S105 S210 | | Enoyl-CoA hydratase/isomerase signature: F125-L181 | ProfileScan |
| | | | | | Enoyl-CoA hydratase/isomerase family: R57-P225 | HMMER-PFAM |
| | | | | | Enoyl-CoA hydratase/isomerase: BL00166A: G55-K66 BL00166B: V93-E114 BL00166C: V140-A166 BL00166D: L190-P225 BL00166E: A289-R294 | BLIMPS-BLOCKS |
| | | | | | Enoyl CoA hydratase isomerase: PD000432: I59-P225 | BLAST-PRODOM |
| | | | | | Enoyl-CoA hydratase/isomerase: DM00366|P30084|34-285: I59-K295 | BLAST-DOMO |
| 2 | 2470792CD1 | 515 | T33 S94 T235 S389 S414 T114 T120 T193 T257 S356 T371 T512 Y168 Y404 | N128 N341 N396 | ATP/GTP-binding site motif A (P-loop): A5-K11 | MOTIFS |
| | | | | | Male sterility protein 2: PD018334: W200-L445 | BLAST-PRODOM |
| 3 | 1506182CD1 | 279 | T130 S109 S256 S4 T38 S95 S136 | N36 | Signal cleavage: M1-N22 | SPScan |
| | | | | | Lipopolysaccharide core | BLIMPS- |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | S223 S235 | | biosynthesis protein signature: PR01020A: V9-L27 PR01020C: H65-Q89 | PRINTS |
| | | | | | Protein F26H9.4: PD023338: V9-L106 | BLAST-PRODOM |
| | | | | | Membrane protein YLR328W: DM07979\|P53204\|1-394: M1-L106 | BLAST-DOMO |
| 4 | 2690842CD1 | 432 | S35 S74 S76 T84 S176 S178 S203 T208 S287 S333 T353 T370 T394 S398 S80 T110 T117 S254 Y253 | N111 | Phospholipid biosynthetic acyltransferase: R18-S203 | HMMER-PFAM |
| 5 | 5027764CD1 | 451 | T72 S14 S16 S97 S144 T175 S206 S258 S272 S287 T320 T47 T68 S121 T124 T348 | N50 N58 N66 N357 | Vespid venom allergen PLA1 signature PR00825A: P188-H205, L211-P231 | BLIMPS-PRINTS |
| | | | | | Lipase precursor, signal, hydrolase, lipid degradation, glycoprotein PD001492: N64-I335 | BLAST-PRODOM |
| | | | | | Triacylglycerol lipase: DM00344\|A49488\|25-326: L39-V333 | BLAST-DOMO |
| | | | | | Signal peptide: M1-A18 | HMMER |
| | | | | | Signal cleavage: M1-A18 | SPScan |
| | | | | | Lipase: H31-D319 | HMMER-PFAM |
| | | | | | Lipases, serine proteins BL00120: N102-I116, D146-S160, Y223-C233 | BLIMPS-BLOCKS |
| | | | | | Triacylglycerol lipase family signature PR00821: S59-F78, V104-H119, D147-E165, C246-E261, P325-K340 | BLIMPS-PRINTS |
| 6 | 2488174CD1 | 312 | S125 S57 S190 S212 S87 S96 S121 S138 S166 T201 S253 | N15 N83 N128 N199 N242 | Phospholipase A2 histidine active site (PDOC00109): C28-C35 | MOTIFS |
| | | | | | Phospholipase A2 isozymes: PD033132: M1-R66 | BLAST-PRODOM |
| | | | | | A2, phospholipase, histidine: DM05541\|P80003\|1-141: M1-R66 DM05541\|B56338\|1-136: P2-R66 | BLAST-DOMO |

TABLE 4

| Polynucleotide SEQ ID NO: | Incyte Polynucleotide ID | Sequence Length | Selected Fragments | Sequence Fragments | 5' Position | 3' Position |
|---|---|---|---|---|---|---|
| 7 | 2372651CB1 | 1667 | 1-177 | 6827519J1 (SINTNOR01) | 235 | 827 |
| | | | | 7001351H1 (HEALDIR01) | 531 | 1136 |
| | | | | 5601906H1 (UTRENON03) | 1339 | 1652 |
| | | | | 6515361H1 (THYMDIT01) | 1116 | 1650 |
| | | | | 5602106H1 (UTRENON03) | 1340 | 1653 |
| | | | | 3574443H1 (BRONNOT01) | 1 | 297 |
| 8 | 2470792CB1 | 2124 | 1-863, 2075-2124 | 70774783V1 | 1678 | 2066 |
| | | | | 70780150V1 | 682 | 1195 |
| | | | | 70067901V1 | 1548 | 2065 |
| | | | | 70067625V1 | 1209 | 1685 |
| | | | | 6830177J1 (SINTNOR01) | 1 | 688 |
| | | | | 70781158V1 | 633 | 1157 |
| | | | | 70778451V1 | 946 | 1600 |
| | | | | 622417H1 (PGANNOT01) | 1871 | 2124 |
| 9 | 1506182CB1 | 2955 | 1-52, 550-587, 2567-2955, 1065-2018 | 1433938R1 (BEPINON01) | 1718 | 2183 |
| | | | | 70047889V1 | 1439 | 1983 |
| | | | | 1257710F6 (MENITUT03) | 2437 | 2955 |
| | | | | 6884818J1 (BRAHTDR03) | 1947 | 2605 |
| | | | | 3284318F6 (HEAONOT05) | 10 | 617 |
| | | | | 662677R6 (BRAINOT03) | 275 | 841 |
| | | | | 1308778H1 (COLNFET02) | 1 | 261 |
| | | | | 6969331U1 | 742 | 1505 |
| | | | | 662677T6 (BRAINOT03) | 1050 | 1640 |
| 10 | 2690842CB1 | 1579 | 1-313 | 2690842H1 (LUNGNOT23) | 969 | 1210 |
| | | | | 7362670H1 (LUNLTUE02) | 1 | 615 |

TABLE 4-continued

| Polynucleotide SEQ ID NO: | Incyte Polynucleotide ID | Sequence Length | Selected Fragments | Sequence Fragments | 5' Position | 3' Position |
|---|---|---|---|---|---|---|
|  |  |  |  | 7261254H1 (UTRETMC01) | 1010 | 1579 |
|  |  |  |  | 6913602H1 (PITUDIR01) | 587 | 1043 |
| 11 | 5027764CB1 | 3170 | 2450-2737, 507-1843 | 841054T6 (PROSTUT05) | 2557 | 3170 |
|  |  |  |  | 3224086R6 (COLNNON03) | 2477 | 3021 |
|  |  |  |  | 70705531V1 | 1621 | 2291 |
|  |  |  |  | 4438670H1 (SINTNOT22) | 1 | 272 |
|  |  |  |  | 6933434H1 (SINTTMR02) | 14 | 652 |
|  |  |  |  | 70635824V1 | 2273 | 2892 |
|  |  |  |  | 70750908V1 | 1723 | 2330 |
|  |  |  |  | 70743692V1 | 999 | 1595 |
|  |  |  |  | 71051604V1 | 470 | 1054 |
|  |  |  |  | 71246013V1 | 1078 | 1692 |
| 12 | 2488174CB1 | 1900 | 1-1772 | 70906023V1 | 1368 | 1889 |
|  |  |  |  | 71530085V1 | 497 | 1187 |
|  |  |  |  | 71531355V1 | 566 | 1284 |
|  |  |  |  | 70905361V1 | 1263 | 1888 |
|  |  |  |  | 2488174F6 (LUNGNOT22) | 1 | 532 |
|  |  |  |  | 71527244V1 | 1426 | 1899 |

TABLE 5

| Polynucleotide SEQ ID NO: | Incyte Project ID | Representative Library |
|---|---|---|
| 7 | 2372651CB1 | PROSNOT18 |
| 8 | 2470792CB1 | EOSIHET02 |
| 9 | 1506182CB1 | BRAITUT02 |
| 10 | 2690842CB1 | UTRETMC01 |
| 11 | 5027764CB1 | PROSTUT05 |
| 12 | 2488174CB1 | LUNGNOT22 |

TABLE 6

| Library | Vector | Library Description |
|---|---|---|
| BRAITUT02 | PSPORT1 | Library was constructed using RNA isolated from brain tumor tissue removed from the frontal lobe of a 58-year-old Caucasian male during excision of a cerebral meningeal lesion. Pathology indicated a grade 2 metastatic hypernephroma. Patient history included a grade 2 renal cell carcinoma, insomnia, and chronic airway obstruction. Family history included a malignant neoplasm of the kidney. |
| EOSIHET02 | PBLUESCRIPT | Library was constructed using RNA isolated from peripheral blood cells apheresed from a 48-year-old Caucasian male. Patient history included hypereosinophilia. The cell population was determined to be greater than 77% eosinophils by Wright's staining. |
| LUNGNOT22 | pINCY | Library was constructed using RNA isolated from lung tissue removed from a 58-year-old Caucasian female. The tissue sample used to construct this library was found to have tumor contaminant upon microscopic examination. Pathology for the associated tumor tissue indicated a caseating granuloma. Family history included congestive heart failure, breast cancer, secondary bone cancer, acute myocardial infarction and atherosclerotic coronary artery disease. |
| PROSNOT18 | pINCY | Library was constructed using RNA isolated from diseased prostate tissue removed from a 58-year-old Caucasian male during a radical cystectomy, radical prostatectomy, and gastrostomy. Pathology indicated adenofibromatous hyperplasia; this tissue was associated with a grade 3 transitional cell carcinoma. Patient history included angina and emphysema. Family history included acute myocardial infarction, atherosclerotic coronary artery disease, and type II diabetes. |
| PROSTUT05 | PSPORT1 | Library was constructed using RNA isolated from prostate tumor tissue removed from a 69-year-old Caucasian male during a radical prostatectomy. Pathology indicated adenocarcinoma (Gleason grade 3 + 4). Adenofibromatous hyperplasia was also present. Family history included congestive heart failure, multiple myeloma, hyperlipidemia, and rheumatoid arthritis. |
| UTRETMC01 | pINCY | This large size-fractionated library was constructed using pooled cDNA from two different donors. cDNA was generated using mRNA isolated from endometrial tissue removed from a 32-year-old Caucasian female (donor A) during total abdominal hysterectomy, bilateral salpingo-oophorectomy, and cystocele repair; and from endometrial tissue removed from a 48-year-old Caucasian female (donor B) during a vaginal hysterectomy, rectocele repair, and bilateral salpingo-oophorectomy. |

TABLE 6-continued

| Library | Vector | Library Description |
|---|---|---|
| | | Pathology for donor A indicated the endometrium was in the proliferative phase. The right ovary showed a corpus luteal cyst. For donor B, pathology indicated chronic cervicitis and the endometrium was weakly proliferative. The right ovary and specimen from the peritoneum indicated endometriosis focally involving the surface of the right ovary and the peritoneum. Pathology for the matched tumor tissue indicated a single submucosal leiomyoma, which exhibited extensive hyalin change with hyalin-type necrosis. The left ovary contained a corpus luteum cyst. Donor A presented with abdominal pain, stress incontinence, and dysmenorrhea. Patient history included hemorrhagic ovarian cysts, uterine endometriosis, normal delivery, and cesarean deliveries. Donor B presented with metrorrhagia, extrinsic asthma, depressive disorder, and anxiety state. Patient history included alcohol abuse, hyperlipidemia, a normal delivery, tobacco abuse in remission, and meningitis. Patient medications (B) included Prozac, Trazodone, Clorazepate. and Medrol. |

TABLE 7

| Program | Description | Reference | Parameter Threshold |
|---|---|---|---|
| ABI FACTURA | A program that removes vector sequences and masks ambiguous bases in nucleic acid sequences. | Applied Biosystems, Foster City, CA. | |
| ABI/ PARACEL FDF | A Fast Data Finder useful in comparing and annotating amino acid or nucleic acid sequences. | Applied Biosystems, Foster City, CA; Paracel Inc., Pasadena, CA. | Mismatch <50% |
| ABI AutoAssembler | A program that assembles nucleic acid sequences. | Applied Biosystems, Foster City, CA. | |
| BLAST | A Basic Local Alignment Search Tool useful in sequence similarity search for amino acid and nucleic acid sequences. BLAST includes five functions: blastp, blastn, blastx, tblastn, and tblastx. | Altschul, S. F. et al. (1990) J. Mol. Biol. 215: 403-410; Altschul, S. F. et al. (1997) Nucleic Acids Res. 25: 3389-3402. | ESTs: Probability value = 1.0E−8 or less Full Length sequences: Probability value = 1.0E−10 or less |
| FASTA | A Pearson and Lipman algorithm that searches for similarity between a query sequence and a group of sequences of the same type. FASTA comprises as least five functions: fasta, tfasta, fastx, tfastx, and ssearch. | Pearson, W. R. and D. J. Lipman (1988) Proc. Natl. Acad Sci. USA 85: 2444-2448; Pearson, W. R. (1990) Methods Enzymol. 183: 63-98; and Smith, T. F. and M. S. Waterman (1981) Adv. Appl. Math. 2: 482-489. | ESTs: fasta E value = 1.06E−6 Assembled ESTs: fasta Identity = 95% or greater and Match length = 200 bases or greater; fastx E value = 1.0E−8 or less Full Length sequences: fastx score = 100 or greater |
| BLIMPS | A BLocks IMProved Searcher that matches a sequence against those in BLOCKS, PRINTS, DOMO, PRODOM, and PFAM databases to search for gene families, sequence homology, and structural fingerprint regions. | Henikoff, S. and J. G. Henikoff (1991) Nucleic Acids Res. 19: 6565-6572; Henikoff, J. G. and S. Henikoff (1996) Methods Enzymol. 266: 88-105; and Attwood, T. K. et al. (1997) J. Chem. Inf. Comput. Sci. 37: 417-424. | Probability value = 1.0E−3 or less |
| HMMER | An algorithm for searching a query sequence against hidden Markov model (HMM)-based databases of protein family consensus sequences, such as PFAM. | Krogh, A. et al. (1994) J. Mol. Biol. 235: 1501-1531; Sonnhammer, E. L. L. et al. (1988) Nucleic Acids Res. 26: 320-322; Durbin, R. et al. (1998) Our World View, in a Nutshell, Cambridge Univ. Press, pp. 1-350. | PFAM hits: Probability value = 1.0E−3 or less Signal peptide hits: Score = 0 or greater |
| ProfileScan | An algorithm that searches for structural and sequence motifs in protein sequences that match sequence patterns defined in Prosite. | Gribskov, M. et al. (1988) CABIOS 4: 61-66; Gribskov, M. et al. (1989) Methods Enzymol. 183: 146-159; Bairoch, A. et al. (1997) Nucleic Acids Res. 25: 217-221. | Normalized quality score ≧ GCG-specified "HIGH" value for that particular Prosite motif. Generally, score = 1.4-2.1. |
| Phred | A base-calling algorithm that examines automated sequencer traces with high sensitivity and probability. | Ewing, B. et al. (1998) Genome Res. 8: 175-185; Ewing, B. and P. Green (1998) Genome Res. 8: 186-194. | |
| Phrap | A Phils Revised Assembly Program including SWAT and CrossMatch, programs based on efficient implementation of the Smith-Waterman algorithm, useful in searching sequence homology and assembling DNA sequences. | Smith, T. F. and M. S. Waterman (1981) Adv. Appl. Math. 2: 482-489; Smith, T. F. and M. S. Waterman (1981) J. Mol. Biol. 147: 195-197; and Green, P., University of Washington, Seattle, WA. | Score = 120 or greater; Match length = 56 or greater |
| Consed | A graphical tool for viewing and editing Phrap assemblies. | Gordon, D. et al. (1998) Genome Res. 8: 195-202. | |
| SPScan | A weight matrix analysis program that scans protein sequences for the presence of secretory signal peptides. | Nielson, H. et al. (1997) Protein Engineering 10: 1-6; Claverie, J. M. and S. Audic (1997) CABIOS 12: 431-439. | Score = 3.5 or greater |
| TMAP | A program that uses weight matrices to delineate transmembrane segments on protein sequences and determine orientation. | Persson, B. and P. Argos (1994) J. Mol. Biol. 237: 182-192; Persson, B. and P. Argos (1996) Protein Sci. 5: 363-371. | |

TABLE 7-continued

| Program | Description | Reference | Parameter Threshold |
|---|---|---|---|
| TMHMMER | A program that uses a hidden Markov model (HMM) to delineate transmembrane segments on protein sequences and determine orientation. | Sonnhammer, E. L. et al. (1998) Proc. Sixth Intl. Conf. on Intelligent Systems for Mol. Biol., Glasgow et al., eds., The Am. Assoc. for Artificial Intelligence Press, Menlo Park, CA, pp. 175-182. | |
| Motifs | A program that searches amino acid sequences for patterns that matched those defined in Prosite. | Bairoch, A. et al. (1997) Nucleic Acids Res. 25: 217-221; Wisconsin Package Program Manual, version 9, page M51-59, Genetics Computer Group, Madison, WI. | |

What is claimed is:

1. An isolated polynucleotide encoding a polypeptide comprising the amino acid of SEQ ID NO: 5, wherein:
   a) the polynucleotide comprises the sequence of SEQ ID NO: 11; and
   b) the polypeptide has phosphatidylserine-specific phospholipase A 1 activity.

2. A recombinant polynucleotide comprising a promoter sequence operably linked to the polynucleotide of claim 1.

3. An isolated cell transformed with the recombinant polynucleotide of claim 2.

4. A method of producing an isolated polypeptide that is encoded by the polynucleotide of claim 1 and that has phosphotidylserine-specific phospholipase A1 activity, the method comprising:
   a) culturing a cell under conditions suitable for expression of the polypeptide, wherein said cell is transformed with a recombinant polynucleotide, and said recombinant polynucleotide comprise a promoter sequence operably linked to the polynucleotide of claim 1, and
   b) recovering the polypeptide so expressed.

5. An isolated polynucleotide comprising a polynucleotide sequence selected from the group consisting of:
   a) a polynucleotide sequence having at least about 95% sequence identity to the polynucleotide sequence of SEQ ID NO: 11, wherein the polynucleotide encodes a polypeptide having phosphatidylserine-specific phospholipase A 1 activity; and b) a polynucleotide sequence complementary to the polynucleotide sequence of a.

* * * * *